(12) United States Patent
Parrag et al.

(10) Patent No.: US 10,945,958 B2
(45) Date of Patent: *Mar. 16, 2021

(54) DEXAMETHASONE PRODRUG COMPOSITIONS AND USES THEREOF

(71) Applicant: Ripple Therapeutics Corporation, Toronto (CA)

(72) Inventors: Ian Charles Parrag, Mississauga (CA); Matthew Alexander John Statham, Milton (CA); Kyle Battiston, Toronto (CA); Dimitra Louka, Toronto (CA); Hans Christian Fischer, Toronto (CA); J. Paul Santerre, Toronto (CA); Wendy Alison Naimark, Toronto (CA)

(73) Assignee: RIPPLE THERAPEUTICS CORPORATION, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/699,305

(22) Filed: Nov. 29, 2019

(65) Prior Publication Data

US 2020/0113834 A1    Apr. 16, 2020

Related U.S. Application Data

(63) Continuation of application No. 16/698,372, filed on Nov. 27, 2019, which is a continuation of application No. 16/396,400, filed on Apr. 26, 2019, now Pat. No. 10,588,862, which is a continuation of application No. PCT/CA2019/050136, filed on Feb. 1, 2019.

(60) Provisional application No. 62/758,234, filed on Nov. 9, 2018, provisional application No. 62/627,608, filed on Feb. 7, 2018, provisional application No. 62/625,460, filed on Feb. 2, 2018.

(51) Int. Cl.

| A61K 9/50 | (2006.01) |
|---|---|
| A61K 9/51 | (2006.01) |
| A61K 47/55 | (2017.01) |
| A61P 29/00 | (2006.01) |
| A61K 9/16 | (2006.01) |
| A61K 9/70 | (2006.01) |
| A61K 9/00 | (2006.01) |
| A61K 31/573 | (2006.01) |
| A61K 47/69 | (2017.01) |

(52) U.S. Cl.
CPC .......... *A61K 9/167* (2013.01); *A61K 9/0048* (2013.01); *A61K 9/0051* (2013.01); *A61K 9/0092* (2013.01); *A61K 9/1682* (2013.01); *A61K 9/50* (2013.01); *A61K 9/5089* (2013.01); *A61K 9/51* (2013.01); *A61K 9/5192* (2013.01); *A61K 9/7007* (2013.01); *A61K 31/573* (2013.01); *A61K 47/55* (2017.08); *A61K 47/6921* (2017.08); *A61K 47/6953* (2017.08); *A61P 29/00* (2018.01)

(58) Field of Classification Search
None
See application file for complete search history.

(56) References Cited

U.S. PATENT DOCUMENTS

| 3,591,612 | A | | 7/1971 | Allais et al. |
|---|---|---|---|---|
| 3,663,579 | A | * | 5/1972 | Stache et al. .......... A61K 47/50 552/509 |
| 4,024,871 | A | | 5/1977 | Stephenson |
| 4,532,316 | A | | 7/1985 | Henn |
| 4,833,215 | A | | 5/1989 | Jedlinski et al. |
| 4,916,193 | A | | 4/1990 | Tang et al. |
| 5,013,841 | A | | 5/1991 | Matsumoto et al. |
| 5,217,493 | A | | 6/1993 | Raad et al. |
| 5,250,524 | A | | 10/1993 | Kramer et al. |
| 5,321,099 | A | | 6/1994 | Goldwasser et al. |
| 5,387,598 | A | | 2/1995 | Rossignol |
| 5,512,558 | A | | 4/1996 | Enhsen et al. |
| 5,578,621 | A | | 11/1996 | Rossignol |
| 5,798,115 | A | | 8/1998 | Santerre et al. |
| 5,856,348 | A | | 1/1999 | Rossignol |
| 5,859,038 | A | | 1/1999 | Rossignol |
| 5,886,013 | A | | 3/1999 | Rossignol |
| 5,965,590 | A | | 10/1999 | Rossignol |
| 5,968,961 | A | | 10/1999 | Rossignol |
| 6,020,353 | A | | 2/2000 | Rossignol |
| 6,051,576 | A | | 4/2000 | Ashton et al. |
| 6,096,525 | A | | 8/2000 | Patnaik |
| 6,117,894 | A | | 9/2000 | Rossignol |
| 6,127,507 | A | | 10/2000 | Santerre |
| 6,299,604 | B1 | | 10/2001 | Ragheb et al. |
| 6,344,035 | B1 | | 2/2002 | Chudzik et al. |

(Continued)

FOREIGN PATENT DOCUMENTS

| CA | 2461099 A1 | 4/2003 |
|---|---|---|
| CA | 2467321 A1 | 11/2005 |

(Continued)

OTHER PUBLICATIONS

Bach et al., "Retention of antibacterial activity and bacterial colonization of antiseptic-bonded central venous catheters," J Antimicrob Chemother. 37:315-22 (1996).

(Continued)

*Primary Examiner* — Alton N Pryor
(74) *Attorney, Agent, or Firm* — Wilson Sonsini Goodrich & Rosati

(57) ABSTRACT

The disclosure features dexamethasone prodrug dimers of dexamethasone and pharmaceutical compositions thereof useful for, e.g., the extended release of a drug and for the treatment of a disease or condition.

19 Claims, 33 Drawing Sheets

(56) References Cited

U.S. PATENT DOCUMENTS

| | | | |
|---|---|---|---|
| 6,429,300 | B1 | 8/2002 | Kurz et al. |
| 6,602,915 | B2 | 8/2003 | Uhrich |
| 6,689,350 | B2 | 2/2004 | Uhrich |
| 6,703,037 | B1 | 3/2004 | Hubbell et al. |
| 6,770,725 | B2 | 8/2004 | Santerre |
| 8,349,309 | B2 | 1/2013 | Santerre et al. |
| 8,968,626 | B2 | 3/2015 | Pham et al. |
| 9,056,048 | B2 | 6/2015 | Diamond et al. |
| 1,058,886 | A1 | 3/2020 | Parrag et al. |
| 2003/0035787 | A1 | 2/2003 | Uhrich |
| 2003/0039689 | A1 | 2/2003 | Chen et al. |
| 2003/0118528 | A1 | 6/2003 | Walters et al. |
| 2003/0158598 | A1 | 8/2003 | Ashton et al. |
| 2003/0203030 | A1 | 10/2003 | Ashton et al. |
| 2004/0087664 | A1 | 5/2004 | Marcus et al. |
| 2004/0180036 | A1 | 9/2004 | Ashton et al. |
| 2005/0008695 | A1 | 1/2005 | Ashton et al. |
| 2005/0031577 | A1 | 2/2005 | Uhrich |
| 2005/0070470 | A1 | 3/2005 | Coy et al. |
| 2005/0159609 | A1 | 7/2005 | King et al. |
| 2005/0164994 | A1 | 7/2005 | Ashton et al. |
| 2005/0220839 | A1 | 10/2005 | DeWitt et al. |
| 2005/0255079 | A1 | 11/2005 | Santerre et al. |
| 2010/0062974 | A1 | 3/2010 | LaRonde et al. |
| 2013/0289223 | A1 | 10/2013 | Santerre et al. |
| 2014/0256696 | A1 | 9/2014 | Sinha et al. |
| 2016/0038651 | A1 | 2/2016 | Santerre et al. |
| 2019/0247311 | A1 | 8/2019 | Parrag et al. |
| 2019/0275167 | A1 | 9/2019 | Parrag et al. |
| 2020/0113833 | A1 | 4/2020 | Parrag et al. |

FOREIGN PATENT DOCUMENTS

| | | | | |
|---|---|---|---|---|
| CA | 2571320 | A1 | 11/2005 | |
| CA | 2906238 | A1 | 9/2014 | |
| CH | 592687 | A5 * | 11/1977 | ............. A61K 47/50 |
| CN | 1968715 | B | 12/2010 | |
| FR | 2007815 | A5 * | 1/1970 | |
| JP | H07501470 | A | 2/1995 | |
| JP | H0924093 | A | 1/1997 | |
| JP | 2000-501318 | A | 2/2000 | |
| JP | 2007-537168 | A | 12/2007 | |
| WO | WO-95/11907 | A1 | 5/1995 | |
| WO | WO-95/20567 | A1 | 8/1995 | |
| WO | WO-95/28393 | A1 | 10/1995 | |
| WO | WO-97/29778 | A2 | 8/1997 | |
| WO | WO-98/07458 | A1 | 2/1998 | |
| WO | WO-98/50035 | A1 | 11/1998 | |
| WO | WO-99/06430 | A1 | 2/1999 | |
| WO | WO-99/12990 | A1 | 3/1999 | |
| WO | WO-02/09768 | A2 | 2/2002 | |
| WO | WO-03/028527 | A2 | 4/2003 | |
| WO | WO-03/040104 | A1 | 5/2003 | |
| WO | WO-03043657 | A1 | 5/2003 | |
| WO | WO-2004/016214 | A2 | 2/2004 | |
| WO | WO-2005/110485 | A1 | 11/2005 | |
| WO | WO-2011/120044 | A1 | 9/2011 | |
| WO | WO-2014/139033 | A1 | 9/2014 | |
| WO | WO-2017/083794 | A1 | 5/2017 | |
| WO | WO-2019148291 | A1 | 8/2019 | |
| WO | WO-2019148293 | A1 | 8/2019 | |
| WO | WO-2019148294 | A1 | 8/2019 | |
| WO | WO-2020154815 | A1 | 8/2020 | |

OTHER PUBLICATIONS

Blondeau, "Fluoroquinolones: mechanism of action, classification, and development of resistance," Surv Ophthalmol. 49(Suppl. 2):S73-8 (2004).

Burger, Isosterism and bioisosterism in drug design. *Progress in Drug Research*, vol. 37. Ernst Jucker (ed.), 287-328 (1991) (43 pages).

Cheng et al., "Intravitreal sustained-release dexamethasone device in the treatment of experimental uveitis," Invest Ophthalmol Vis Sci. 36(2):442-53 (1995).

Chirife et al., "In vitro antibacterial activity of concentrated polyethylene glycol 400 solutions," Antimicrob Agents Chemother. 24(3):409-12 (1983).

Coessens et al., "Synthesis and in vitro stability of macromolecular prodrugs of norfloxacin," J Cont Release. 47:283-91 (1997).

DiTizio et al., "A liposomal hydrogel for the prevention of bacterial adhesion to catheters," Biomaterials. 19(20):1877-84 (1998).

Extended European Search Report for European Application No. 17206101.2, dated Jun. 6, 2018 (8 pages).

Extended European Search Report for European Patent Application No. 14764271.4, dated Oct. 24, 2016 (7 pages).

Final Rejection for Japanese Application No. 2015-561873, dated May 8, 2018 (8 pages).

First Office Action for Chinese Patent Application No. 201480027630.6, dated Mar. 14, 2017 (15 pages) (English language translation provided).

Ghosh, "Studies directed towards polymeric quinolone antibiotics—synthesis of potential monomers from nalidixic acid," *Polymeric Mat Sci Engin*. 59:790-3 (1988).

Ghosh, Monomers and Polymers from Nalidixic Acid—Synthesis, Characterization, and Hydrolysis Study. *Progress in Biomedical Polymers*. C.G. Gebelein and R.L. Dunn (eds.), Plenum Press, 335-45 (1990).

International Patent Application No. PCT/CA2019/050133. Interface Biologics, Inc., "Ocular Insert," filed Feb. 1, 2019 (116 pages).

International Patent Application No. PCT/CA2019/050135. Interface Biologics, Inc., "Glass Formulations and Uses Thereof," filed Feb. 1, 2019 (181 pages).

International Patent Application No. PCT/CA2019/050136. Interface Biologics, Inc., "Dexamethsone Prodrug Compositions and Uses Thereof," filed Feb. 1, 2019 (87 pages).

International Preliminary Report on Patentability for International Application No. PCT/CA2014/050284, dated Sep. 15, 2015 (8 pages).

International Search Report and Written Opinion for International Application No. PCT/CA2019/050133, dated Apr. 29, 2019 (16 pages).

International Search Report and Written Opinion for International Application No. PCT/CA2019/050135, dated Apr. 29, 2019 (12 pages).

International Search Report and Written Opinion for International Application No. PCT/CA2019/050136, dated Apr. 29, 2019 (11 pages).

International Search Report and Written Opinion for International Patent Application No. PCT/CA2014/050284, dated Jun. 2, 2014 (13 pages).

Kanra et al., "The short-term efficacy and safety of dexamethasone implant in a difficult-to-treat patient population with persistent diabetic macular edema," Ret Vit. 26(3):221-7 (2017) (8 pages).

Kerns et al., "Piperazinyl-linked fluoroquinolone dimers possessing potent antibacterial activity against drug-resistant strains of *Staphylococcus aureus*," Bioorg Med Chem Lett. 13(10):1745-9 (2003).

Li et al., "Dimeric and Oligomeric Steroids," Chem Rev. 97(1):283-304 (1997).

Michael et al., "Enhanced RNA binding of dimerized aminoglycosides," Bioorg Med Chem. 7(7):1361-71 (1999).

Modak et al., "A New Method for the Direct Incorporation of Antibiotic in Prosthetic Vascular Grafts," Surg Gynecol Obstet. 164:143-147 (1987).

Nathan et al., "Copolymers of Lysine and Polyethylene Glycol: A New Family of Functionalized Drug Carriers," Bioconjug Chem. 4:54-62 (1993).

Nishida et al., "Studies on synthesis of antibacterial agent (NM441). I. Kinetics and mechanism of the reaction of 4-(bromomethyl)-5-methyl-1,3-dioxol-2-one with 1-substituted piperazine (NM394)," Bull Chem Soc Jpn. 67:1419-26 (1994).

Nosova et al., "Synthesis of new fluorinated derivatives of quinolinecarboxylic acids," Chem Heterocycl Compd. 38(8):922-8 (2002).

(56) References Cited

OTHER PUBLICATIONS

Notice of Reasons for Rejection for Japanese Patent Application No. 2015-561873, dated Sep. 19, 2017 (7 Pages) (English language translation provided).
Odian, Introduction. *Principles of Polymerization; Fourth Edition*. Wiley-Interscience, 6-9 (2004) (7 pages).
Office Action for U.S. Appl. No. 16/396,135, dated Jul. 3, 2019 (14 pages).
Paryzek et al., "A new approach to steroid dimers and macrocycles by the reaction of 3-chlorocarbonyl derivatives of bile acids with O,O-, N,N-, and S,S-dinucleophiles," Tetrahedron Lett. 53(46):6212-5 (2012).
Patani et al., "Bioisosterism: A Rational Approach in Drug Design," Chem Rev. 96(8):3147-76 (1996).
Ren et al., "Macromolecular prodrug of dexamethasone prevents particle-induced peri-implant osteolysis with reduced systemic side effects," available in PMC Feb. 10, 2015, published in final edited form as: J Control Release. 175:1-9 (2014) (24 pages).
Response to Non-Final Office Action for U.S. Appl. No. 16/396,400, dated Sep. 24, 2019 (9 pages).
Roseeuw et al., "Polymeric prodrugs of antibiotics with improved efficiency," J Mater Sci Mater Med. 10:743-6 (1999).
*The Merck Index: An Encyclopedia of Chemicals, Drugs and Biologicals, 14th Edition*. O'Neil et al. (eds.), Merck & Co., Inc.: Whitehouse Station, NJ, 1306-7 (2006).
Woo et al., "Biological characterization of a novel biodegradable antimicrobial polymer synthesized with fluoroquinolones," J Biomed Mater Res. 59(1):35-45 (2002).
Woo et al., "Synthesis and characterization of a novel biodegradable antimicrobial polymer," Biomaterials. 21(12):1235-46 (2000).
Xue et al., "New dimeric cholesteryl-based A(LS)2 gelators with remarkable gelling abilities: organogel formation at room temperature," J Colloid Interface Sci. 361(2):556-64 (2011).
Yang, et al., "Utilization of quinolone drugs as monomers: characterization of the synthesis reaction products for poly(norfloxacin diisocyanatododecane polycaprolactone)," Biomacromolecules. 2(1):134-41 (2001).

PCT/CA2020/050117 International Search Report and Written Opinion dated Apr. 15, 2020.
Step-growth Polymerization. http://en.wikipedia.org/wiki/Step-growth_polymerization, retrieved on Jan. 12, 2012 (11 pages).
Berge et al. Pharmaceutical Salts. Journal of Pharmaceutical Sciences 66(1):1-19 (Jan. 1977).
Gaudana et al. Ocular drug delivery. AAPS J. 12(3):348-360 (2010).
Gower et al. Drug discovery in ophthalmology: past success, present challenges, and future opportunities. BMC Ophthalmology 16:11 (Jan. 16, 2016).
U.S. Appl. No. 16/396,135 Office Action dated Jul. 3, 2019.
U.S. Appl. No. 16/396,400 Office Action dated Jun. 24, 2019.
U.S. Appl. No. 16/396,400 Office Action dated Oct. 15, 2019.
U.S. Appl. No. 16/698,372 Office Action dated Jan. 21, 2020.
Chanphai et al. Conjugation of steroids with PAMAM nanoparticles. Colloids and Surfaces B: Biointerfaces 136:1035-1041 (2015).
Janout et al., Bioconjugate-Based Molecular Umbrellas. Bioconjugate Chemistry, 20(2):183-192 (E-Pub Nov. 20, 2008).
Janout et al. Molecular umbrella-amphotercin B conjugates. Bioconjugate Chemistry 25:1408-1411 (2014).
Nahar et al. A review on steroid dimers: 2011-2019. Steroids 164:108736 (2020).
Nahar et al. A review on synthetic and natural steroid dimers: 1997-2006. Current Medicinal Chemistry 14:1349-1370 (2007).
PCT/IB2020/000620 International Search Report and Written Opinion dated Oct. 30, 2020.
Sarker et al. Chapter 6: Applications of Steroid Dimers. in Steroid Dimer: Chemistry and Applications in Drug Design and Delivery, John Wiley & Sons Ltd. pp. 379-407 (2012).
Svobodova et al. Recent advances in steroidal supramolecular gels. RSC Advances 2:4985-5007 (2012).
Howard-Sparks et al. A novel Chemical Delivery System Comprising an Ocular Sustained Re-lease Formulation of a 3a-17a-21-trihydroxy-5B-pregnan-20-one-BIS-5-Fluorouracil Coding. Drug Dev Ind Pharm 33:677-682 (2007).
PCT/IB2020/000663 International Search Report and Written Opinion dated Dec. 1, 2020.

* cited by examiner

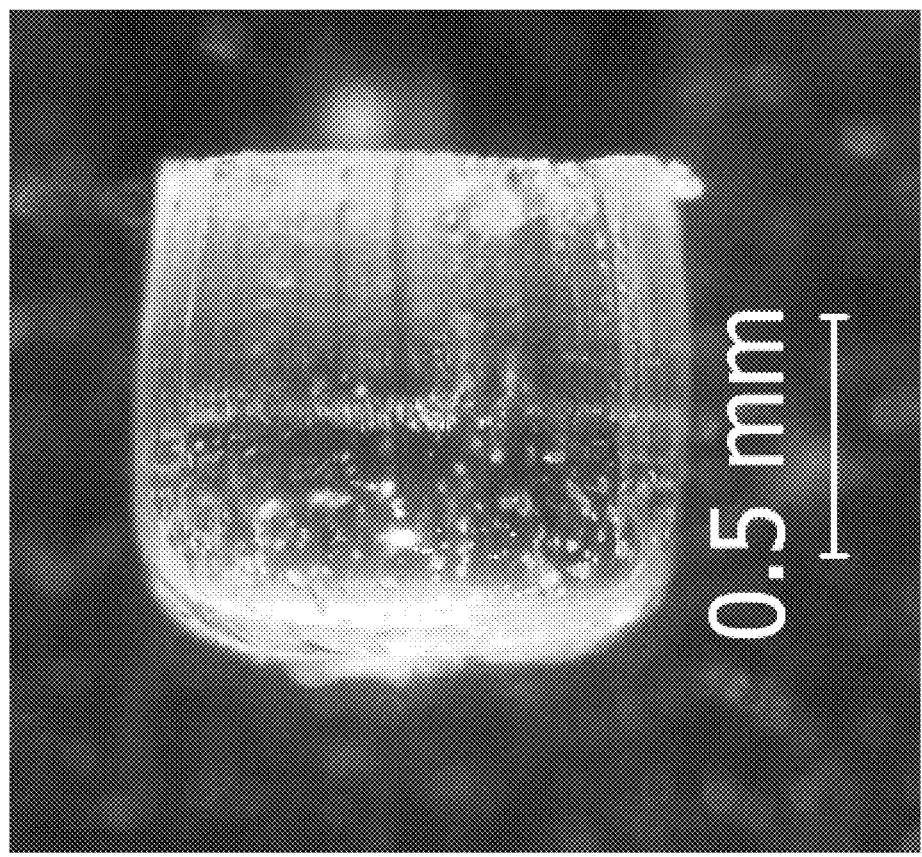

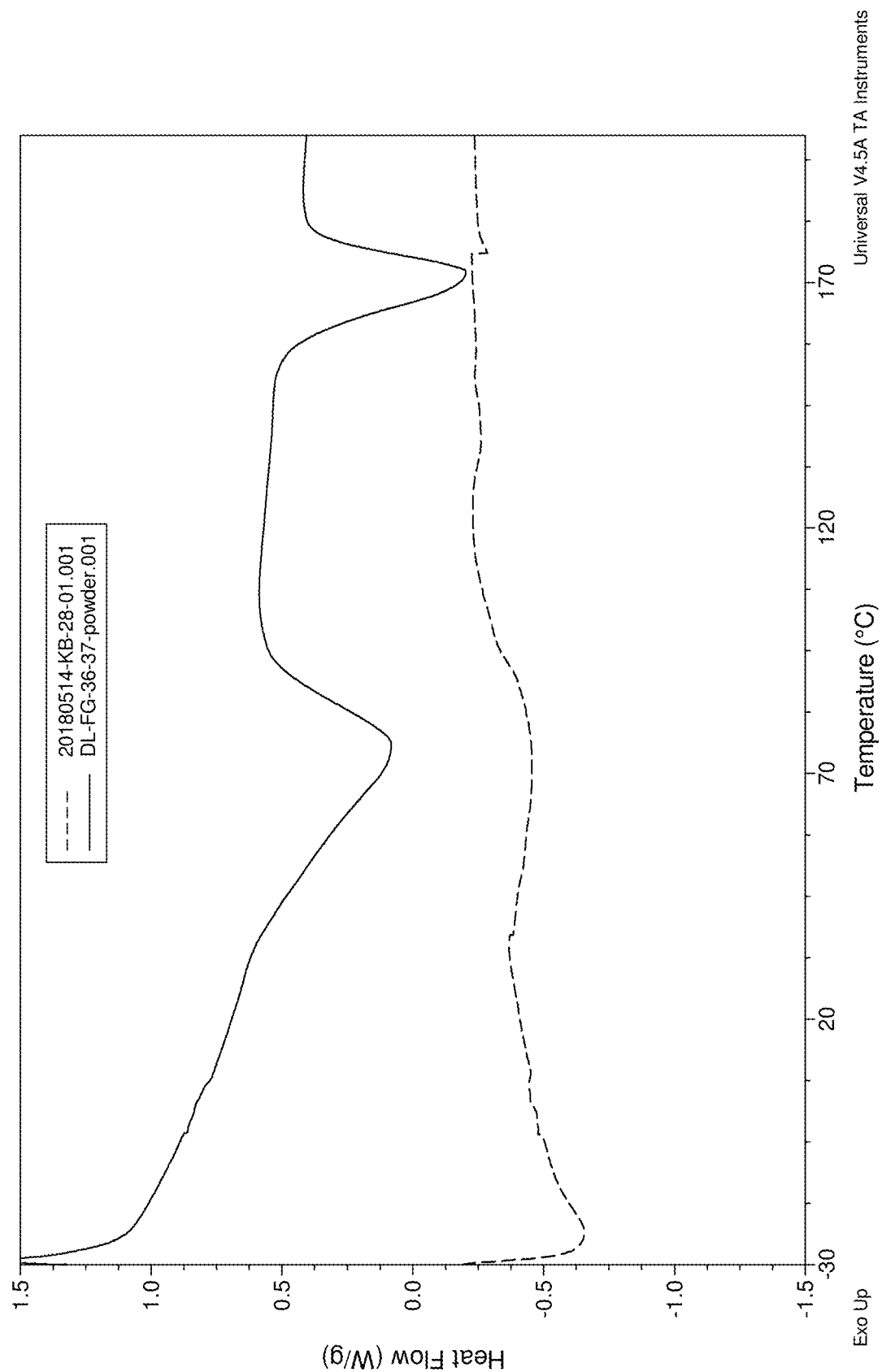

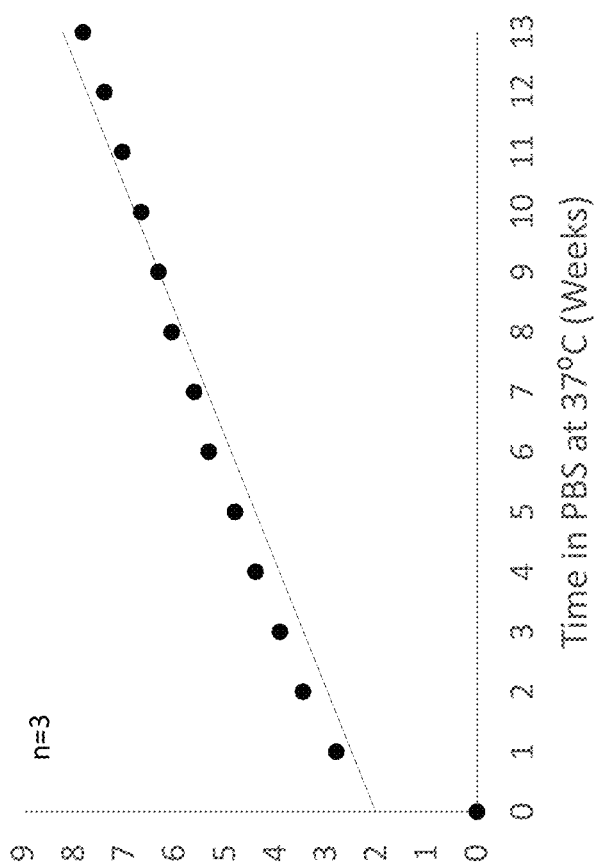
FIG. 8B
FIG. 8C
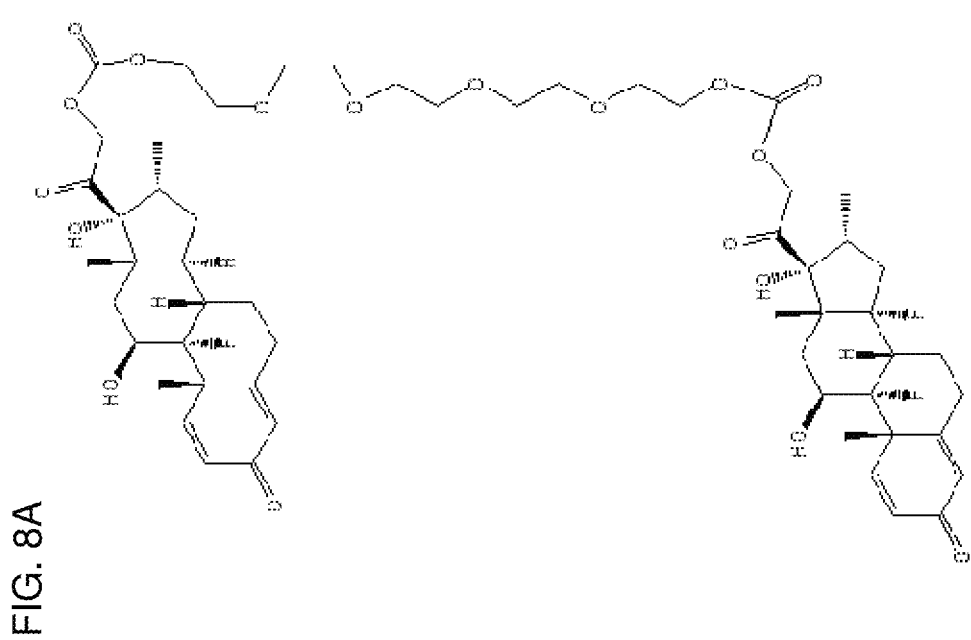
FIG. 8A

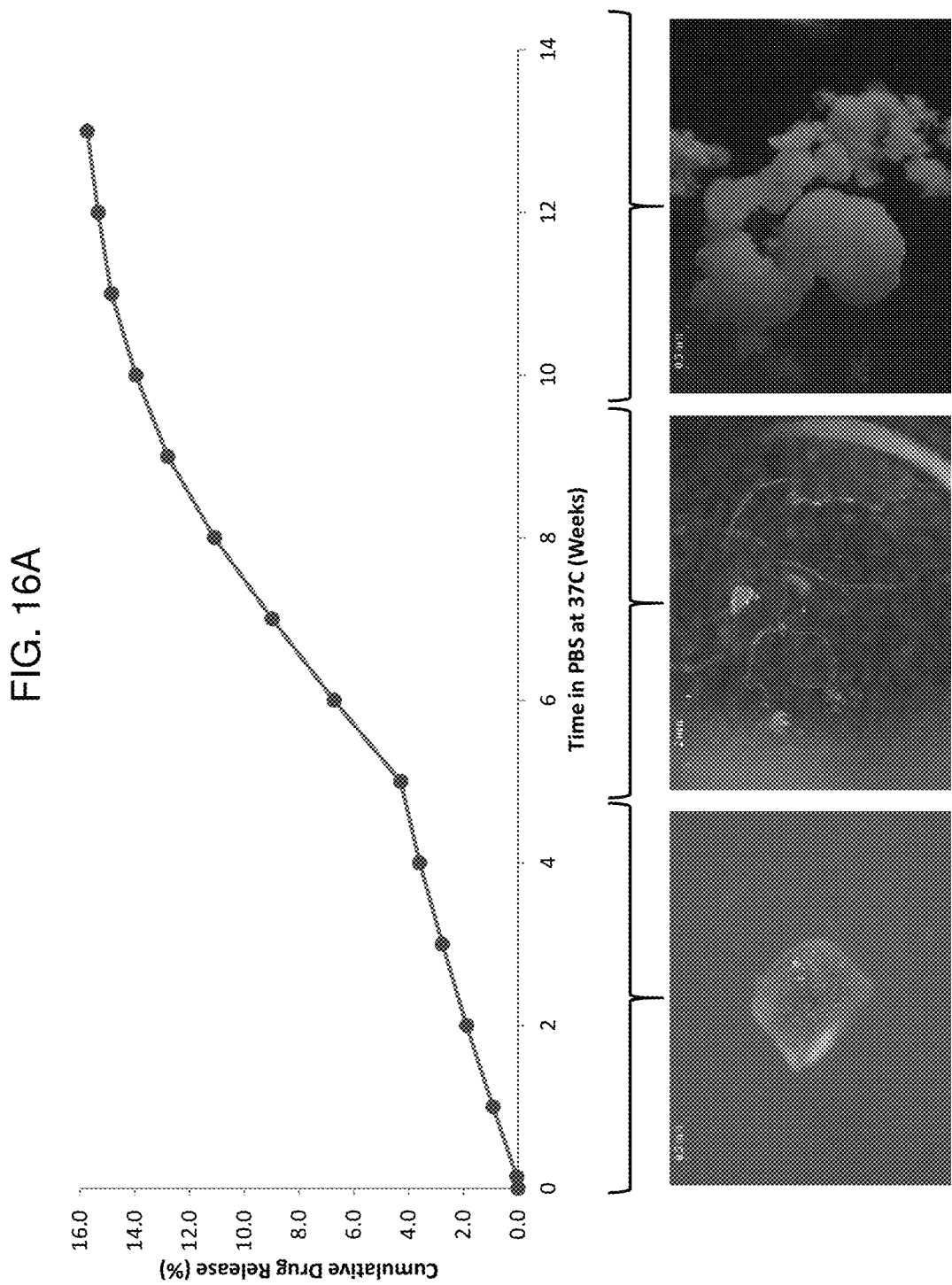

DEXAMETHASONE PRODRUG COMPOSITIONS AND USES THEREOF

BACKGROUND OF THE DISCLOSURE

Dexamethasone is a useful drug in a variety of medical fields, for example in the treatment of inflammatory diseases or conditions and in reducing inflammation associated with surgery or another therapy.

SUMMARY OF THE DISCLOSURE

The disclosure features prodrug dimers formed from dexamethasone and articles formed from the dimers. The articles of the disclosure can be machined, molded, emulsion-processed, electrospun, electrosprayed, blow molded, or extruded to form a fiber, fiber mesh, woven fabric, non-woven fabric, pellet, cylinder, microparticle (e.g., a microbead), nanoparticle (e.g., a nanobead), or any other type shaped article from which the dexamethasone prodrug dimer is released in a controlled fashion.

In one aspect, the disclosure features an article formed from a compound of the disclosure, wherein the article provides controlled release of dexamethasone at 37° C. in 100% bovine serum or at 37° C. in PBS.

In another aspect, the disclosure features compound described by the formula (I):

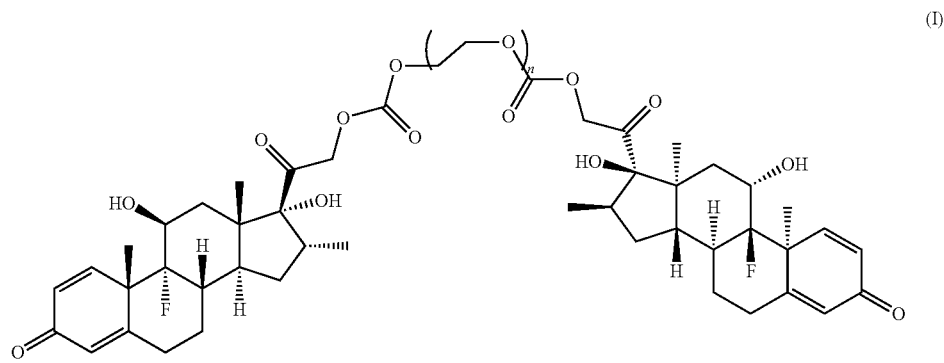

(I)

wherein n is an integer from 1 to 6 (e.g., wherein n is 1, 2, 3, 4, 5, or 6). In some embodiments, n is 1. In further embodiments, n is 2. In particular embodiments, n is 3. In other embodiments, n is 4. In further embodiments, n is 5. In yet other embodiments, n is 6.

In another aspect, the disclosure features a pharmaceutical composition including the compound of the previous aspect, and a pharmaceutically acceptable excipient.

In another aspect, the disclosure features an article including Compound 6 or a compound of formula (I):

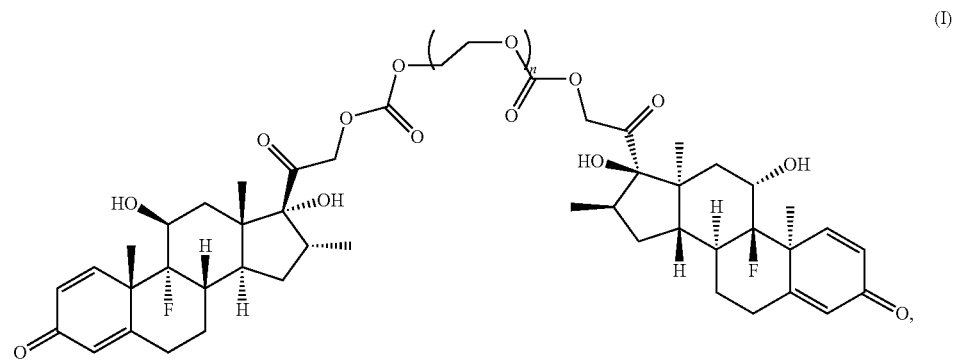

(I)

wherein the article provides controlled release of dexamethasone at 37° C. in 100% bovine serum or at 37° C. in PBS; wherein n is an integer from 1 to 6.

In some embodiments, dexamethasone is released from the article through surface erosion.

In some embodiments, the article releases less than 10% of dexamethasone, as a percentage of the total dexamethasone present in the article in prodrug form, at 37° C. in 100% bovine serum over 5 days; or the surface erosion releases less than 2% of dexamethasone, as a percentage of the total dexamethasone present in the article in prodrug form, at 37° C. in PBS over 5 days; or the surface erosion releases greater than 20% of dexamethasone, as a percentage of the total dexamethasone present in the article in prodrug form, at 37° C. in 100% bovine serum over not fewer than 6 days; or the surface erosion releases greater than 5.0% of dexamethasone as a percentage of the total dexamethasone present in the article in prodrug form, at 37° C. in PBS over not fewer than 6 days; or dexamethasone is released from the article at a rate such that $t_{10}$ is greater than or equal to $1/10$ of $t_{50}$.

In some embodiments, the article further includes from 0.1% to 10% (w/w) of one or more additives, wherein the one or more additives are selected from plasticizers, antioxidants, binders, lubricants, radio-opaque agents, and mixtures thereof.

In further embodiments, the article is a fiber, fiber mesh, woven fabric, non-woven fabric, pellet, cylinder, hollow tube, microparticle, nanoparticle, or shaped article. In other embodiments, the article is free of controlled release excipient, free of a crystallization inhibiting excipient, free of a mechanical integrity enhancing excipient, and/or free of a binding excipient. In some embodiments, the article is in a glassy state.

In certain embodiments, the controlled release is provided by any one of: dimensions of the article, composition of the article, crystallinity of the article, surface area of the article, or combinations thereof.

In another aspect, the disclosure features an article including a compound of formula (I):

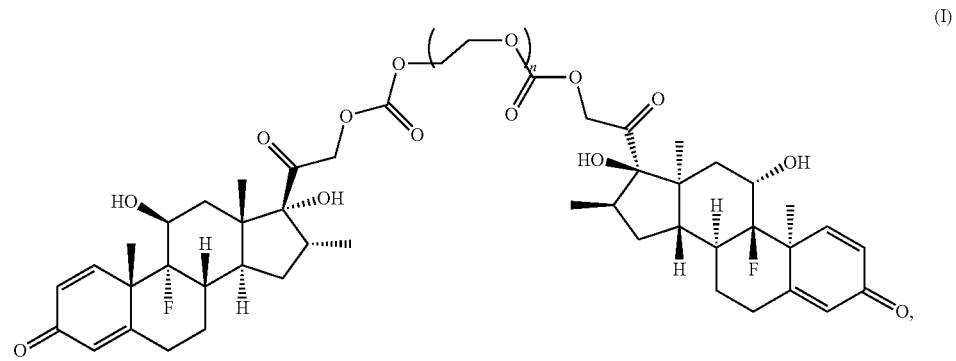

(I)

wherein the article is formed by a process including the steps of: (a) heating the compound to form a melt; and (b) heat molding the melt to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features an article including a compound of formula (I):

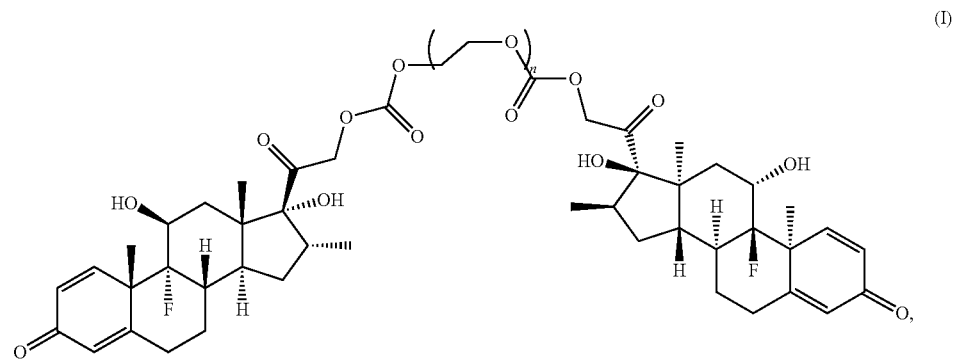

(I)

wherein the article is formed by a process including the steps of: (a) heating the compound to form a melt; and (b) injection molding the melt to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features an article including a compound of formula (I):

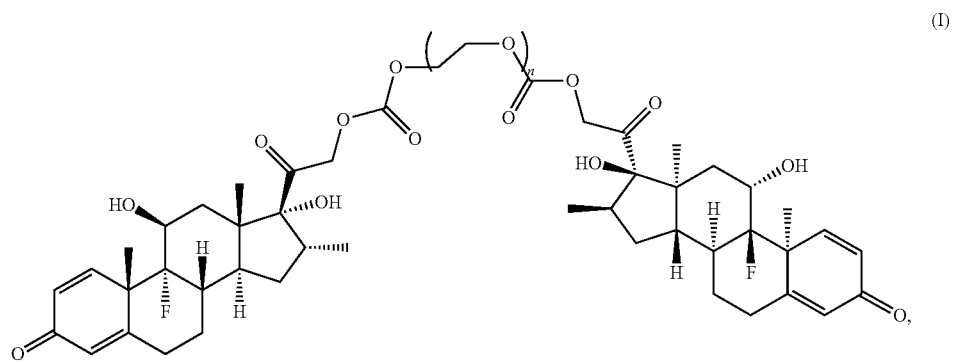

(I)

wherein the article is formed by a process including the steps of: (a) heating the compound to form a melt; and (b) blow molding the melt to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features an article including a compound of formula (I):

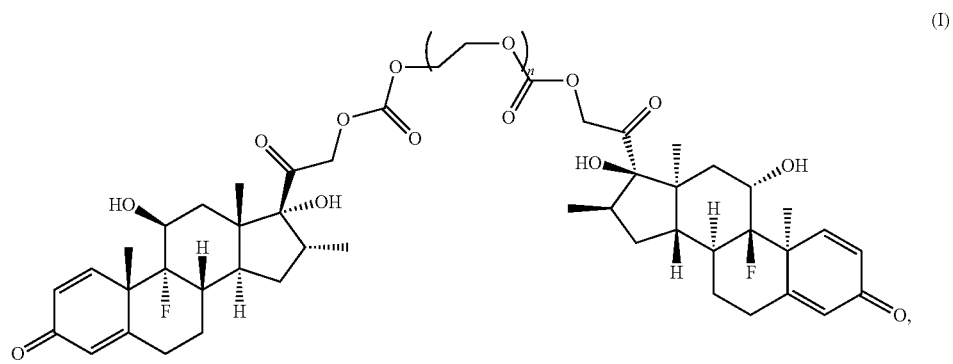

(I)

wherein the article is formed by a process including the steps of: (a) dissolving the compound to form a solution; and (b) evaporating the solvent to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state. In some embodiments, step (b) includes solvent casting to form a film or a fiber.

In another aspect, the disclosure features an article including a compound of formula (I):

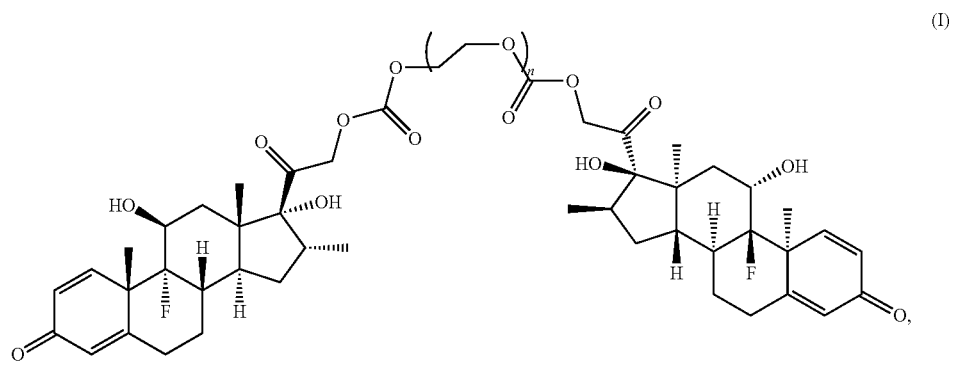

(I)

wherein the article is formed by a process including the steps of: (a) dissolving the compound to form a solution; and (b) electrospinning or electrospraying the solution to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features an article including a compound of formula (I):

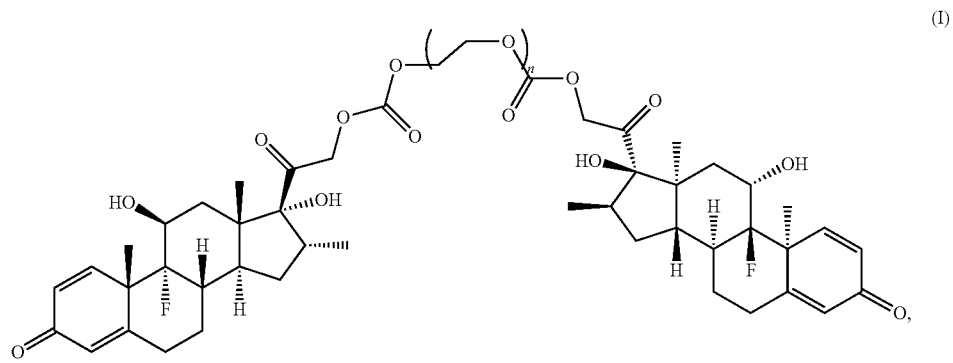

(I)

wherein the article is formed by a process including the steps of: (a) heating the compound to form a melt; and (b) electrospinning or electrospraying the melt to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features an article including a compound of formula (I):

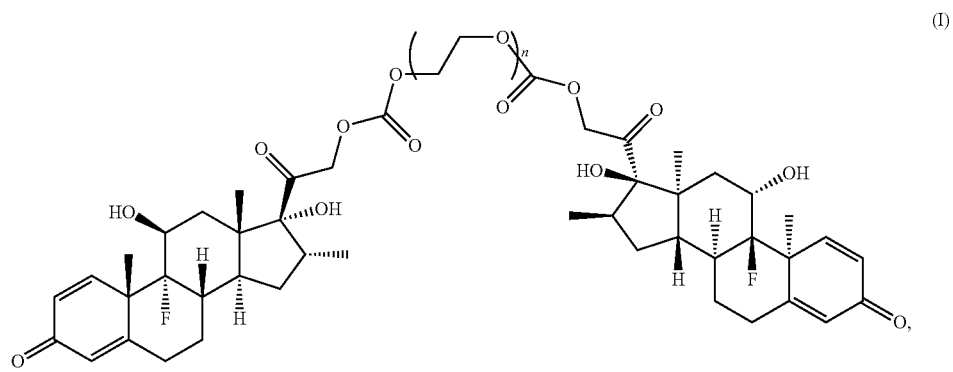

(I)

wherein the article is formed by a process including the steps of: (a) heating the compound to form a melt; (b) extruding the melt to form the article, wherein n is an integer from 1 to 6. In some embodiments, the article is free of controlled release excipient, free of a crystallization inhibiting excipient, free of a mechanical integrity enhancing excipient, and/or free of a binding excipient; or the article optionally has a glassy state.

In some embodiments of any of the above aspects, n is 1. In further embodiments, n is 2. In certain embodiments of the articles of the disclosure, n is 3. In other embodiments, n is 4. In further embodiments, n is 5. In yet other embodiments, n is 6.

In another aspect, the disclosure features an article formed from a compound of the disclosure.

In some embodiments of the articles of the disclosure, at least 70% (e.g., at least 75%, at least 80%, at least 85%, at least 90%, at least 95%, or at least 99%) (w/w) of the article is the compound of formula (I). In some embodiments, at least 90% (e.g., at least 91%, at least 92%, at least 93%, at least 94%, at least 95%, at least 96%, at least 97%, at least 98%, or at least 99%) (w/w) of the article is the compound of formula (I).

In further embodiments of the articles of the disclosure, the compound or dexamethasone is released from the article through surface erosion. In some embodiments, the surface erosion releases less than 10% (e.g., less than 9%, less than 8%, less than 7%, less than 6%, less than 5%, less than 4%, less than 3%, less than 2%, or less than 1%) of dexamethasone, as a percentage of the total drug, dexamethasone, present in the article in prodrug form, at 37° C. in 100% bovine serum over 5 days; or the surface erosion releases less than 2% (e.g., less than 1.8%, less than 1.5%, less than 1.2%, less than 1.0%, or less than 0.5%) of dexamethasone, as a percentage of the total drug, dexamethasone, present in the article in prodrug form, at 37° C. in PBS over 5 days. In still other embodiments of any of the above articles, the surface erosion releases greater than 20% (e.g., greater than 22%, 24%, 26%, 28%, or 30%) of dexamethasone (as a percentage of the total dexamethasone present in the article in prodrug form) at 37° C. in 100% bovine serum over not fewer than 6 days, 8 days, 10 days, or 12 days (e.g., greater than 24% of dexamethasone at 37° C. in 100% bovine serum over 10 days). In other embodiments of any of the above articles, the surface erosion releases greater than 5.0% (e.g., greater than 6.0%, 8.0%, 10%, 12%, or 15%) of dexamethasone (as a percentage of the total dexamethasone present in the article in prodrug form) at 37° C. in PBS over not fewer than 6 days, 8 days, 10 days, or 12 days (e.g., greater than 5% of dexamethasone at 37° C. in PBS over 10 days). The dexamethasone can be released from the article at a rate such that $t_{10}$ is greater than or equal to $\frac{1}{10}$ of $t_{50}$. In some embodiments, the article further includes from 0.1% to 10% (e.g., from 0.1 to 5%, from 0.1 to 2%, from 0.5 to 2%, from 1 to 10%) (w/w) of one or more additives, wherein the one or more additives are selected from plasticizers, antioxidants, binders, lubricants, radio-opaque agents, and mixtures thereof.

The article may be a fiber, fiber mesh, woven fabric, non-woven fabric, pellet, cylinder, hollow tube, microparticle (e.g., a microbead), nanoparticle (e.g., a nanobead), or shaped article. In some embodiments, the article is free of controlled release excipient, free of a crystallization inhibiting excipient, free of a mechanical integrity enhancing excipient, and/or free of a binding excipient; or the article optionally has a glassy state.

In another aspect, the disclosure features a fiber formed from a compound of the disclosure.

In another aspect, the disclosure features a fiber formed from a compound of formula (I):

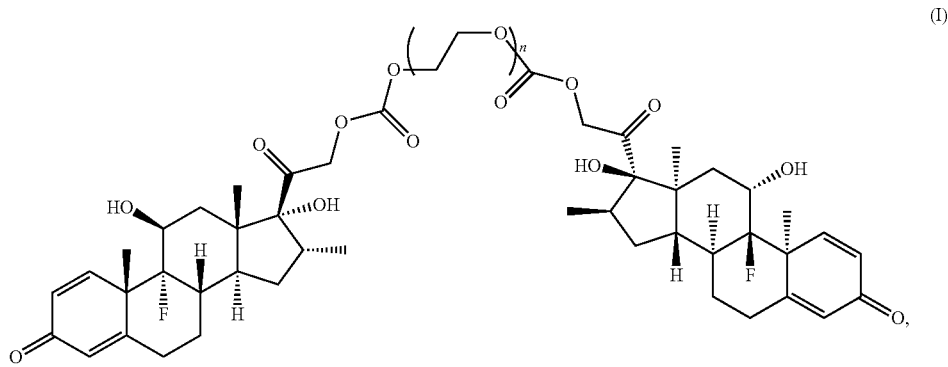

wherein the fiber is prepared by a process including the steps of: (a) dissolving the compound in a solvent to form a solution; and (b) electrospinning, dry spinning, wet spinning, or gel spinning the solution to form the fiber, wherein n is an integer from 1 to 6. In some embodiments, the fiber is free of controlled release excipient, free of a crystallization inhibiting excipient, free of a mechanical integrity enhancing excipient, and/or free of a binding excipient; or the fiber optionally has a glassy state.

In another aspect, the disclosure features a fiber formed from a compound of formula (I):

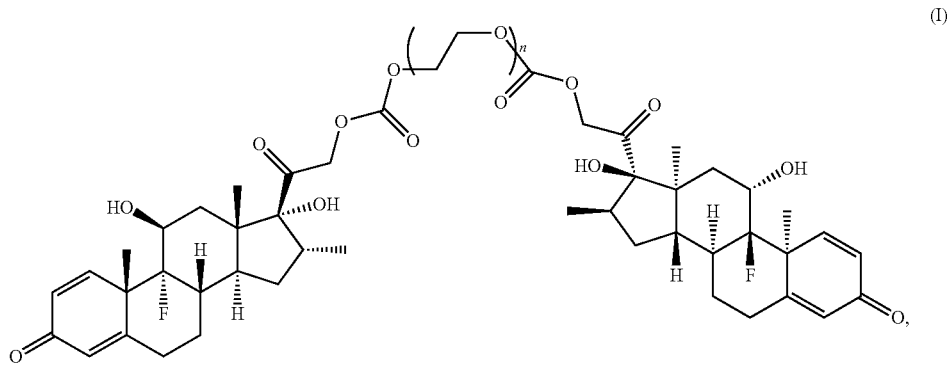

wherein the fiber is prepared by a process including the steps of: (a) heating the compound to form a melt; and (b) extruding the melt to form the fiber (i.e., melt spinning), wherein n is an integer from 1 to 6. In some embodiments, the fiber is free of controlled release excipient, free of a crystallization inhibiting excipient, free of a mechanical integrity enhancing excipient, and/or free of a binding excipient; or the fiber optionally has a glassy state.

In another aspect, the disclosure features a fiber formed from a compound of formula (I):

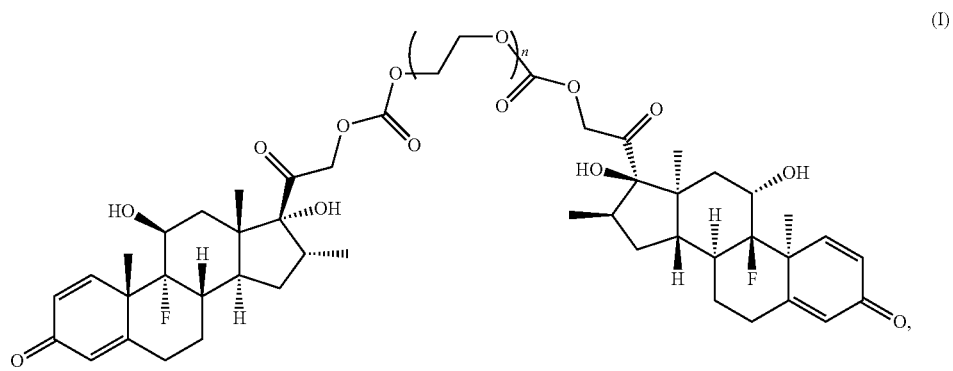

wherein the fiber is prepared by a process including the steps of: (a) heating the compound to form a melt; and (b) electrospinning the melt to form the fiber, wherein n is an integer from 1 to 6. In some embodiments, the fiber is free of controlled release excipient, free of a crystallization inhibiting excipient, free of a mechanical integrity enhancing excipient, and/or free of a binding excipient; or the fiber optionally has a glassy state.

In embodiments, n is 1. In further embodiments, n is 2. In particular embodiments of the fibers of the disclosure, n is 3. In another embodiment, n is 4. In further embodiments, n is 5. In yet other embodiments, n is 6.

In some embodiments of the fibers of the disclosure, at least 70% (e.g., at least 75%, at least 80%, at least 85%, at least 90%, at least 95%, or at least 99%) (w/w) of the fiber is the compound of formula (I). In some embodiments, at least 90% (e.g., at least 91%, at least 92%, at least 93%, at least 94%, at least 95%, at least 96%, at least 97%, at least 98%, or at least 99%) (w/w) of the fiber is the compound of formula (I).

In some embodiments of the fibers of the disclosure, the compound or dexamethasone is released from the fiber through surface erosion. In some embodiments, the surface erosion releases less than 10% (e.g., less than 9%, less than 8%, less than 7%, less than 6%, less than 5%, less than 4%, less than 3%, less than 2%, or less than 1%) of dexamethasone, as a percentage of the total drug, dexamethasone, present in the fiber in prodrug form, at 37° C. in 100% bovine serum over 5 days; or the surface erosion releases less than 2% (e.g., less than 1.8%, less than 1.5%, less than 1.2%, less than 1.0%, or less than 0.5%) of dexamethasone, as a percentage of the total drug, dexamethasone, present in the fiber in prodrug form, at 37° C. in PBS over 5 days. In still other embodiments of any of the above fibers, the surface erosion releases greater than 20% (e.g., greater than 22%, 24%, 26%, 28%, or 30%) of dexamethasone (as a percentage of the total dexamethasone present in the fiber in prodrug form) at 37° C. in 100% bovine serum over not fewer than 6 days, 8 days, 10 days, or 12 days (e.g., greater than 24% of dexamethasone at 37° C. in 100% bovine serum over 10 days). In other embodiments of any of the above fibers, the surface erosion releases greater than 5.0% (e.g., greater than 6.0%, 8.0%, 10%, 12%, or 15%) of dexamethasone (as a percentage of the total dexamethasone present in the fiber in prodrug form) at 37° C. in PBS over not fewer than 6 days, 8 days, 10 days, or 12 days (e.g., greater than 5% of dexamethasone at 37° C. in PBS over 10 days). The dexamethasone can be released from the fiber at a rate such that $t_{10}$ is greater than or equal to $\frac{1}{10}$ of $t_{50}$.

In further embodiments of the fibers of the disclosure, the fiber further includes from 0.1% to 10% (e.g., from 0.1 to 5%, from 0.1 to 2%, from 0.5 to 2%, from 1 to 10%) (w/w) of one or more additives, wherein the one or more additives are selected from plasticizers, antioxidants, binders, lubricants, radio-opaque agents, and mixtures thereof.

In particular embodiments of the fibers of the disclosure, the fiber is free of controlled release excipient, free of a crystallization inhibiting excipient, free of a mechanical integrity enhancing excipient, and/or free of a binding excipient; or the fiber optionally has a glassy state.

In another aspect, the disclosure features a fiber mesh or woven fabric formed from a fiber of the disclosure. The disclosure further features a non-woven fabric formed from a fiber of the disclosure. The fiber mesh, woven fabric, and non-woven fabric can be formed from the fibers using methods known in the art. In particular embodiments, the fiber mesh is free of controlled release excipient, free of a crystallization inhibiting excipient, free of a mechanical integrity enhancing excipient, and/or free of a binding excipient; or the fiber mesh optionally has a glassy state.

In another aspect, the disclosure features a glassy state composition formed from a compound of the disclosure.

In a further aspect, the disclosure features glassy state composition formed from a compound of formula (I):

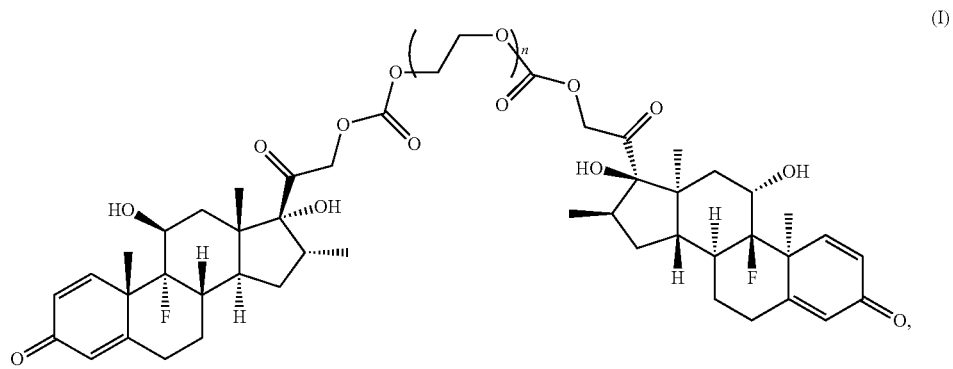

(I)

wherein the composition is prepared by a process including the steps of: (a) heating the compound to form a melt; and (b) cooling the melt to form the composition, wherein n is an integer from 1 to 6. In some embodiments, the glassy state composition is free of controlled release excipient, free of a crystallization inhibiting excipient, free of a mechanical integrity enhancing excipient, and/or free of a binding excipient.

In some embodiments, n is 1. In further embodiments, n is 2. In some embodiments of the glassy state compositions of the disclosure, n is 3. In other embodiments, n is 4. In yet other embodiments, n is 5. In yet other embodiments, n is 6.

In some embodiments of the glassy state compositions of the disclosure, at least 70% (e.g., at least 75%, at least 80%, at least 85%, at least 90%, at least 95%, or at least 99%) (w/w) of the glassy state composition is the compound of formula (I). In further embodiments, at least 90% (e.g., at least 91%, at least 92%, at least 93%, at least 94%, at least 95%, at least 96%, at least 97%, at least 98%, or at least 99%) (w/w) of the glassy state composition is the compound of formula (I).

In some embodiments of the glassy state compositions of the disclosure, the compound or dexamethasone is released from the glassy state composition through surface erosion.

In some embodiments, the surface erosion releases less than 10% (e.g., less than 9%, less than 8%, less than 7%, less than 6%, less than 5%, less than 4%, less than 3%, less than 2%, or less than 1%) of dexamethasone (as a percentage of the total drug, dexamethasone, present in the glassy state composition in prodrug form) at 37° C. in 100% bovine serum over 5 days. In other embodiments of any of the above glassy state compositions, the surface erosion releases less than 2.0% (e.g., less than 1.8%, 1.5%, 1.2%, 1.0%, or 0.5%) of dexamethasone (as a percentage of the total drug, dexamethasone, present in the glassy state composition in prodrug form) at 37° C. in PBS over 5 days, 7 days, 10 days, or 14 days (e.g., less than 2% of dexamethasone at 37° C. in PBS over 5 days). In still other embodiments of any of the above glassy state compositions, the surface erosion releases greater than 20% (e.g., greater than 22%, 24%, 26%, 28%, or 30%) of dexamethasone (as a percentage of the total dexamethasone present in the glassy state composition in prodrug form) at 37° C. in 100% bovine serum over not fewer than 6 days, 8 days, 10 days, or 12 days (e.g., greater than 24% of dexamethasone at 37° C. in 100% bovine serum over 10 days). In other embodiments of any of the above glassy state compositions, the surface erosion releases greater than 5.0% (e.g., greater than 6.0%, 8.0%, 10%, 12%, or 15%) of dexamethasone (as a percentage of the total dexamethasone present in the glassy state composition in prodrug form) at 37° C. in PBS over not fewer than 6 days, 8 days, 10 days, or 12 days (e.g., greater than 5% of dexamethasone at 37° C. in PBS over 10 days). The dexamethasone can be released from the glassy state composition at a rate such that $t_{10}$ is greater than or equal to $\frac{1}{10}$ of $t_{50}$.

In further embodiments of the glassy state compositions of the disclosure, the glassy state composition further includes from 0.1% to 10% (e.g., from 0.1 to 5%, from 0.1 to 2%, from 0.5 to 2%, from 1 to 10%) (w/w) of one or more additives, wherein the one or more additives are selected from plasticizers, antioxidants, binders, lubricants, radio-opaque agents, and mixtures thereof. The glassy state composition can be formed by machining, molding, electrospinning, electrospraying, blow molding, fiber spinning (e.g., wet spinning, dry spinning, gel spinning, melt spinning, etc.), or extruding.

In some embodiments, the glassy state composition is a fiber, fiber mesh, woven fabric, non-woven fabric, pellet, cylinder, hollow tube, microparticle (e.g., a microbead), nanoparticle (e.g., a nanobead), or shaped article in the shape of a cylinder, a cube, a sheet, a star, a toroid, a pyramid, a sphere, an irregular polygon, or a regular polygon.

In further embodiments, the glassy state composition is a shaped article in the form of fibers having a mean diameter of from about 0.01 to 1 mm (e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm).

In other embodiments, the glassy state composition is a shaped article in the form of pellets having a mean diameter of from about 0.2 to 5 mm (e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm).

In further embodiments, the glassy state composition is a shaped article in the form of cylinders of from about 0.01 to 1 mm in diameter (e.g., about 0.01 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm) and 0.5 to 20 mm in length (e.g., about to 0.5 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm). In some embodiments, the length of the cylinder is about 0.5 to 10 mm, or about 1 to 10 mm.

In yet other embodiments, the glassy state composition is a shaped article in the form of microparticles having a mean diameter of from about 1 to 1000 μm (e.g., about 10 to 1000 μm, about 100 to 1000 μm, about 200 to 1000 μm, about 500 to 1000 μm, about 700 to 1000 μm, or about 900 to 1000 μm).

In still other embodiments, the glassy state composition is a shaped article in the form of nanoparticles having a mean diameter of from about 0.01 to 1 μm (about 0.05 to 1 μm, about 0.1 to 1 μm, about 0.2 to 1 μm, about 0.3 to 1 μm, about 0.4 to 1 μm, about 0.5 to 1 μm, about 0.6 to 1 μm, about 0.7 to 1 μm, about 0.8 to 1 μm, or about 0.9 to 1 μm).

In certain embodiments of the glassy state compositions of the disclosure, the glassy state composition is free of controlled release excipient, free of a crystallization inhibiting excipient, free of a mechanical integrity enhancing excipient, and/or free of a binding excipient.

In another aspect, the disclosure features a substrate including a coating formed from a compound of the disclosure.

In another aspect, the disclosure features a substrate including a coating formed from a compound of formula (I):

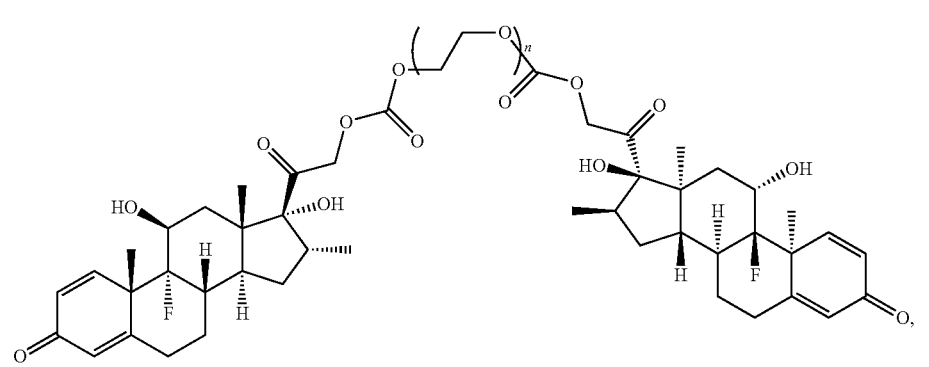

wherein n is an integer from 1 to 6. In some embodiments, the coating is free of controlled release excipient, free of a crystallization inhibiting excipient, free of a mechanical integrity enhancing excipient, and/or free of a binding excipient; or the coating optionally has a glassy state.

In some embodiments, n is 1. In further embodiments, n is 2. In certain embodiments of the substrates of the disclosure, n is 3. In other embodiments, n is 4. In still other embodiments, n is 5. In yet other embodiments, n is 6.

In some embodiments of the substrates of the disclosure, at least 70% (e.g., at least 75%, at least 80%, at least 85%, at least 90%, at least 95%, or at least 99%) (w/w) of the coating is the compound of formula (I). In some embodiments, at least 90% (e.g., at least 91%, at least 92%, at least 93%, at least 94%, at least 95%, at least 96%, at least 97%, at least 98%, or at least 99%) (w/w) of the coating is the compound of formula (I).

In some embodiments of the substrates of the disclosure, the compound or dexamethasone is released from the coating through surface erosion. In some embodiments, the surface erosion releases less than 10% (e.g., less than 9%, less than 8%, less than 7%, less than 6%, less than 5%, less than 4%, less than 3%, less than 2%, or less than 1%) of dexamethasone, as a percentage of the total drug, dexamethasone, present in the coating in prodrug form, at 37° C. in 100% bovine serum over 5 days; or the surface erosion releases less than 2% (e.g., less than 1.8%, less than 1.5%, less than 1.2%, less than 1.0%, or less than 0.5%) of dexamethasone, as a percentage of the total drug, dexamethasone, present in the coating in prodrug form, at 37° C. in PBS over 5 days. In still other embodiments of any of the above coatings, the surface erosion releases greater than 20% (e.g., greater than 22%, 24%, 26%, 28%, or 30%) of dexamethasone (as a percentage of the total dexamethasone present in the coating in prodrug form) at 37° C. in 100% bovine serum over not fewer than 6 days, 8 days, 10 days, or 12 days (e.g., greater than 24% of dexamethasone at 37° C. in 100% bovine serum over 10 days). In other embodiments of any of the above coatings, the surface erosion releases greater than 5.0% (e.g., greater than 6.0%, 8.0%, 10%, 12%, or 15%) of dexamethasone (as a percentage of the total dexamethasone present in the coating in prodrug form) at 37° C. in PBS over not fewer than 6 days, 8 days, 10 days, or 12 days (e.g., greater than 5% of dexamethasone at 37° C. in PBS over 10 days). The dexamethasone can be released from the coating at a rate such that $t_{10}$ is greater than or equal to $\frac{1}{10}$ of $t_{50}$.

In still other embodiments of the substrates of the disclosure, the coating further includes from 0.1% to 10% (e.g., from 0.1 to 5%, from 0.1 to 2%, from 0.5 to 2%, from 1 to 10%) (w/w) of one or more additives, wherein the one or more additives are selected from plasticizers, antioxidants, binders, lubricants, radio-opaque agents, and mixtures thereof. In some embodiments, the coating is a fiber, fiber mesh, woven fabric, non-woven fabric, pellet, cylinder, hollow tube, microparticle (e.g., a microbead), nanoparticle (e.g., a nanobead), or other shaped article.

In some embodiments of the substrates of the disclosure, the coating is free of controlled release excipient, free of a crystallization inhibiting excipient, free of a mechanical integrity enhancing excipient, and/or free of a binding excipient; or the coating optionally has a glassy state.

In further embodiments of the substrates of the disclosure, the coating has a glassy state and is formed from a compound of the disclosure.

In another aspect, the disclosure features a coating having a glassy state formed from a compound of the disclosure.

In another aspect, the disclosure features an implantable medical device including a substrate of the disclosure, wherein the coating resides on the surface of the implantable medical device.

In another aspect, the disclosure features a method of forming an article including a compound of formula (I):

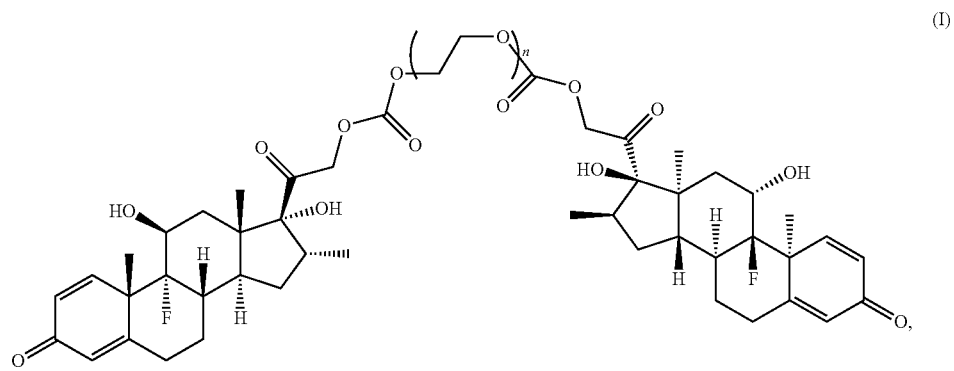

wherein the article is formed by a process including the steps of: (a) heating the compound to form a melt; (b) cooling the melt to form a glassy state composition; and (c) heating the glassy state composition to a temperature above the glass transition temperature of the glassy state composition and shaping the glassy state composition to form a shaped article, wherein n is an integer from 1 to 6. Step (c) can include extruding, molding, blow molding, heat spinning, electrospinning, or electrospraying the glassy state composition to form the shaped article. In some embodiments, the method forms an article free of controlled release excipient, free of a crystallization inhibiting excipient, free of a mechanical integrity enhancing excipient, and/or free of a binding excipient; or the method forms an article that optionally has a glassy state.

In yet another aspect, the disclosure features a method of forming an article including a compound of formula (I):

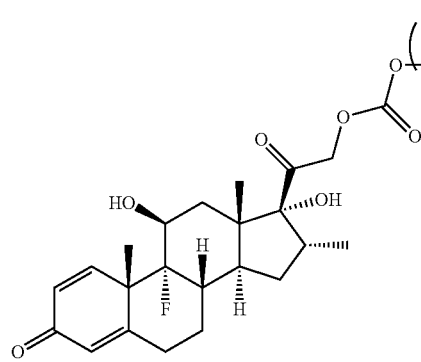

wherein the article is formed by a process including the steps of: (a) dissolving the compound in a solvent to form a solution; (b) evaporating the solvent to form a glassy state composition; and (c) heating the glassy state composition to a temperature above the glass transition temperature of the glassy state composition and shaping the glassy state composition to form a shaped article, wherein n is an integer from 1 to 6. Step (c) can include extruding, molding, blow molding, heat spinning, electrospinning, or electrospraying the glassy state composition to form the shaped article. In some embodiments, the method forms an article free of controlled release excipient, free of a crystallization inhibiting excipient, free of a mechanical integrity enhancing excipient, and/or free of a binding excipient; or the method forms an article that optionally has a glassy state. In some embodiments of the methods of the disclosure, step (c) includes molding, extruding, blow molding, electrospinning, heat spinning, or electrospraying the glassy state composition to form the shaped article (e.g., a fiber, fiber mesh, woven fabric, non-woven fabric, pellet, cylinder, microparticle (e.g., a microbead), or nanoparticle (e.g., a nanobead), or another shaped article). In other embodiments, microparticles are prepared by melting the compound to form glassy state pellets or other shaped forms, crushing the glassy state articles into rough or irregular-shaped particles, filtering particles through sieves, and heating the particles above the Tg to round them into smoother spherical particles. In further embodiments, the method produces an article free of controlled release excipient, free of a crystallization inhibiting excipient, free of a mechanical integrity enhancing excipient, and/or free of a binding excipient; or the method produces an article that optionally has a glassy state.

In a further aspect, the disclosure features a method of forming an article comprising a compound of formula (I):

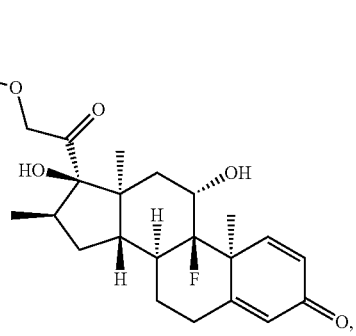

wherein n is an integer from 1 to 6, and wherein the article is formed by a process comprising the steps of: (a) dissolving the compound in a solvent to form a solution; (b) electrospraying the solution to form a glassy state composition; and (c) heating the glassy state composition to a temperature above the glass transition temperature of the glassy state composition and shaping the glassy state composition to form a coating; wherein n is an integer from 1 to 6. In particular embodiments, the method forms an article that is free of controlled release excipient, free of a crystallization inhibiting excipient, free of a mechanical integrity enhancing excipient, and/or free of a binding excipient; or the method forms an article that optionally has a glassy state.

In another aspect, the disclosure features a solid crystalline form of Compound 1 having an X-ray powder diffraction (XRPD) pattern including three, four, five, or more angles 2θ (°) of 9.316°, 11.501°, 14.019°, 15.982°, 17.268°, 17.685°, 18.658°, 20.440°, 21.782°, 23.472°, 29.816°, and/or 33.150°.

In some embodiments, the solid crystalline form of Compound 1 has an XRPD pattern including at least one peak at diffraction angle 2θ (°) of 9.316°. In some embodiments, the solid crystalline form of Compound 1 has an XRPD pattern including at least one peak at diffraction angle 2θ (°) of 11.501°. In some embodiments, the solid crystalline form of Compound 1 has an XRPD pattern including at least one peak at diffraction angle 2θ (°) of 14.019°. In further embodiments, the solid crystalline form of Compound 1 has an XRPD pattern including at least one peak at diffraction angle 2θ (°) of 15.982°. In still further embodiments, the solid crystalline form of Compound 1 has an XRPD pattern including at least one peak at diffraction angle 2θ (°) of 17.268°. In other embodiments, the solid crystalline form of Compound 1 has an XRPD pattern including at least one peak at diffraction angle 2θ (°) of 17.685°. In further embodiments, the solid crystalline form of Compound 1 has an XRPD pattern including at least one peak at diffraction angle 2θ (°) of 18.658°. In yet other embodiments, the solid crystalline form of Compound 1 has an XRPD pattern including at least one peak at diffraction angle 2θ (°) of 20.440°. In some embodiments, the solid crystalline form of Compound 1 has an XRPD pattern including at least one peak at diffraction angle 2θ (°) of 21.782°. In certain embodiments, the solid crystalline form of Compound 1 has an XRPD pattern including at least one peak at diffraction angle 2θ (°) of 23.472°. In still other embodiments, the solid crystalline form of Compound 1 has an XRPD pattern including at least one peak at diffraction angle 2θ (°) of 29.816°. In particular embodiments, the solid crystalline form of Compound 1 has an XRPD pattern including at least one peak at diffraction angle 2θ (°) of 33.150°. In other embodiments, the solid crystalline form of Compound 1 has an XRPD pattern including at least one peak diffraction angle 2θ (°) of 9.316°, 11.501°, 14.019°, 15.982°, 17.268°, 17.685°, 18.658°, 20.440°, 21.782°, 23.472°, 29.816°, and 33.150°.

In another aspect, the disclosure features Compound 6.

The disclosure also includes a pharmaceutical composition comprising Compound 6 and a pharmaceutically acceptable excipient.

Definitions

The term "free of controlled release polymer," as used herein, refers to the absence of an amount of a polymeric material of greater than 10 KDa in the articles of the disclosure that is sufficient to delay or slow the release of the dexamethasone prodrug dimer from the article in comparison to the release profile observed for an otherwise identical article containing none of the polymeric material, where the release profile is measured at 37° C. in 100% fetal bovine serum (FBS).

The term "free of a crystallization inhibiting excipient," as used herein, refers to the absence of an amount of an excipient in the articles of the disclosure that is sufficient to reduce the amount of crystalline dexamethasone prodrug dimer in the article in comparison to the amount of crystalline dexamethasone prodrug dimer observed in an otherwise identical article containing none of the excipient. The level of crystallinity can be measured using DSC or XRD. In particular embodiments, the articles of the disclosure are free of a crystallization inhibiting excipient that is a polymeric material of greater than 10 KDa.

The term "free of a mechanical integrity enhancing excipient," as used herein, refers to the absence of an amount of an excipient in the articles of the disclosure that is sufficient to increase the mechanical integrity of the article in comparison to the mechanical integrity of an otherwise identical article containing none of the excipient. The mechanical integrity of an article can be tested using a 3- or 4-point mechanical bend test (ASTM C1684-18) on the formulation with or without the excipient with the article in the shape of a rod either in the dry state (prior to drug release) or after 15-30% drug release. For articles with a rectangular shape, the mechanical integrity can be tested using a 3-point mechanical bend test (ASTM D790-17) or 4-point mechanical bend test (ASTM D6272) on the formulation with or without excipient either in the dry state (prior to drug release) or after 15-30% drug release. A reduction in mechanical integrity causes the articles to break apart sooner, increasing the total surface area of the quantity of articles, and resulting in a more rapid release profile. In particular embodiments, the articles of the disclosure are free of a mechanical integrity enhancing excipient that is a polymeric material of greater than 10 KDa.

The term "free of a binding excipient," as used herein, refers to the absence of an amount of an excipient in the articles of the disclosure that is sufficient to delay or slow the release of the dexamethasone prodrug dimer from the article in comparison to the release profile observed for an otherwise identical article containing none of the binding excipient, where the release profile is measured at 37° C. in 100% FBS.

The term "cylinder," as used herein, refers to the shape of the pharmaceutical compositions of the disclosure that has parallel sides and a circular or oval cross section, or a shaped cross section (e.g., a star shaped cross section). A mean diameter of the cylinder can range from about 0.01 to 1 mm diameter, e.g., about 0.01 to 0.2 mm, about 0.1 to 0.3 mm, about 0.1 to 0.4 mm, about 0.2 to 0.5 mm, about 0.1 to 0.6 mm, about 0.1 to 0.7 mm, about 0.1 to 0.8 mm, or about 0.1 to 0.9 mm. A mean length of the cylinder can range from about 0.05 to 20 mm, e.g., about 0.05 to 1 mm, about 0.5 to 2 mm, about 0.5 to 4 mm, about 0.5 to 6 mm, about 0.5 to 8 mm, about 0.5 to 10 mm, about 0.5 to 12 mm, about 0.5 to 14 mm, about 0.5 to 16 mm, or about 0.5 to 18 mm. In some embodiments, the mean diameter of the cylinder is in the range of about 0.01 to 1 mm and the mean length of the cylinder is about 0.1 mm to 4.0 mm. In some embodiments, the mean length of the cylinder is about 0.5 to 10 mm, or about 1 to 10 mm.

The term "fiber," as used herein, refers to the shape of the pharmaceutical compositions of the disclosure that is elongated or threadlike. A mean diameter of the fiber can range from about 0.01 to 1 mm, e.g., 0.05 to 0.3 mm, 0.1 to 0.3 mm, 0.15 to 0.3 mm, 0.2 to 0.3 mm, 0.25 to 0.3 mm, 0.01 to 0.1 mm, 0.01 to 0.2 mm, 0.01 to 0.3 mm, 0.01 to 0.4 mm, 0.01 to 0.5 mm, 0.01 to 0.6 mm, 0.01 to 0.7 mm, 0.01 to 0.8 mm, or 0.01 to 0.9 mm. A mean length of the fiber can range from about 20 to 20,000 mm, e.g., about 20 to 1000 mm, about 20 to 2,000 mm, about 100 to 2,000 mm, about 100 to 5,000 mm, about 1,000 to 8,000 mm, about 2,000 to 8,000 mm, about 2,000 to 10,000 mm, about 2,000 to 12,000 mm, about 2,000 to 15,000 mm, or about 5,000 to 18,000 mm.

The term "fiber mesh," as used herein refers to a web or a net in having many attached or woven fibers. The fiber mesh can have aligned and unaligned morphologies.

The term "glassy state," as used herein, refers to an amorphous solid including greater than 70%, 80%, 90%, 95%, 98%, or 99% (w/w) of one or more dexamethasone prodrug dimers of the disclosure and exhibiting a glass transition temperature in the range of from 38 to 150° C. In the glassy state, as measured by DSC or XRD, the level of crystallinity is low, ranging from 0-15%, e.g., 0-1%, 0-3%, 0-5%, 0-7%, 0-9%, 0-10%, or 0-13%. Glass formulations of the disclosure can be formed using heat processing or solvent processing one or more dexamethasone prodrug dimers.

The term "microparticle," as used herein, refers to the shape of the pharmaceutical compositions of the disclosure, which can be regularly or irregularly shaped. A mean diameter of the microparticle can range from about 1 to 1000 µm, e.g., about 10 to 1000 µm, about 100 to 1000 µm, about 200 to 1000 µm, about 500 to 1000 µm, about 700 to 1000 µm, or about 900 to 1000 µm. As used herein, a microbead is a microparticle that is spherical.

The term "nanoparticle," as used herein, refers to the shape of the pharmaceutical compositions of the disclosure, which can be regularly or irregularly shaped. A mean diameter of the nanoparticle can range from about 0.01 to 1 µm, e.g., about 0.05 to 1 µm, about 0.1 to 1 µm, about 0.2 to 1 µm, about 0.3 to 1 µm, about 0.4 to 1 µm, about 0.5 to 1 µm, about 0.6 to 1 µm, about 0.7 to 1 µm, about 0.8 to 1 µm, or about 0.9 to 1 µm. As used herein, a "nanobead" refers to a nanoparticle that is spherical.

The term "non-woven fabric," as used herein, refers to a web structure bonded together by entangling fibers.

The term "pellet," as used herein, refers to the shape of the pharmaceutical compositions of the disclosure that is rounded, spherical, or cylindrical, or a combination thereof. A mean diameter of the pellet can range from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm.

The term "surface erosion," as used herein refers to a process of a gradual disintegration of the pharmaceutical compositions of the disclosure and release of a free drug from the dexamethasone prodrug dimer. Surface erosion can be tailored to achieve desired drug release rates. The rate of surface erosion and release of a given drug from a dexamethasone prodrug dimer may also depend on the quantity of the loaded dexamethasone prodrug dimer as a percent of the final dexamethasone prodrug dimer formulation, article size, solubility of dexamethasone prodrug dimer (e.g., through selection of appropriate linker), and/or surface area of the article. For example, surface erosion mechanism of drug release allows drug delivery articles to be tailored with specific physical features (dimensions, diameters, surface areas, total mass, etc.) to achieve desired drug release rates, and drug release may be designed to be initiated within minutes or hours, and may continue to occur over days, weeks, months, or years.

As used herein, "$t_{50}$" is the time at which 50% of the releasable drug has been released from an article of the disclosure. Time $t_{10}$ is, correspondingly, the time at which 10% of the releasable drug has been released from an article of the disclosure. When the release curve is perfectly linear, $t_{10} = \frac{1}{5}$ of $t_{50}$. When there is an initial burst of released drug, $t_{10}$ is much less than $\frac{1}{5}$ of $t_{50}$. In the compositions and methods of the disclosure $t_{10}$ can be equal to or greater than $\frac{1}{10}$ of $t_{50}$. Drug release from an article or compound of the disclosure can be measured at 37° C. in 100% bovine serum, or at 37° C. in PBS, as described in Example 1.

The term "woven fabric," as used herein, refers to pharmaceutical compositions that resemble materials that are formed by weaving of fibers.

BRIEF DESCRIPTION OF THE DRAWINGS

FIGS. 1A-1F are a series of images and graphs showing Compound 1 (dexamethasone-triethylene glycol-dexamethasone, Dex-TEG-Dex) (FIG. 1A) formed into pellets (FIG. 1B) in the glassy state. Results of testing by differential scanning calorimetry (DSC) (FIG. 1C) and X-ray powder diffraction (XRPD) (FIG. 1D) are shown, and drug release over time was determined (FIG. 1E). FIG. 1F shows representative images of the pellets over time.

FIGS. 3A-3K are a series of images and graphs showing Compound 1 coated onto titanium (FIG. 3A) and poly (styrene-block-isobutylene-block-styrene) (SIBS) surfaces (FIG. 3B), as well as non-woven fibrous meshes aligned (FIG. 3C) and unaligned (FIG. 3D) morphologies and DSC (FIG. 3E) and XRPD data (FIG. 3F). Compound 1 was processed into fibers (FIG. 3G), nanoparticles (FIG. 3H), microparticles (FIGS. 3I and 3J). Microparticles were analyzed by DSC (FIG. 3K).

FIGS. 7A-7F are a series of images and graphs showing Compound 1 formed into heat extruded cylinders (FIGS. 7A-7D), purity of extrudate over time (FIG. 7E), and coating formed from Compound 1 (FIG. 7F).

FIGS. 8A-8C are a series of an image and a graph showing Compound 3 (FIG. 8A) (dexamethasone-pentaethylene glycol-dexamethasone, Dex-EGS-Dex) processed into heat-molded pellets (FIG. 8B) and drug release (FIG. 8C).

(FIG. 13D).

(FIG. 14D).

(FIG. 15D).

FIGS. 16A and 16B are a series of images and graphs showing drug release from heat-molded pellets formed from Compound 4 (FIG. 16A) and Compound 5 (FIG. 16B).

DETAILED DESCRIPTION OF THE DISCLOSURE

Figure 1A:
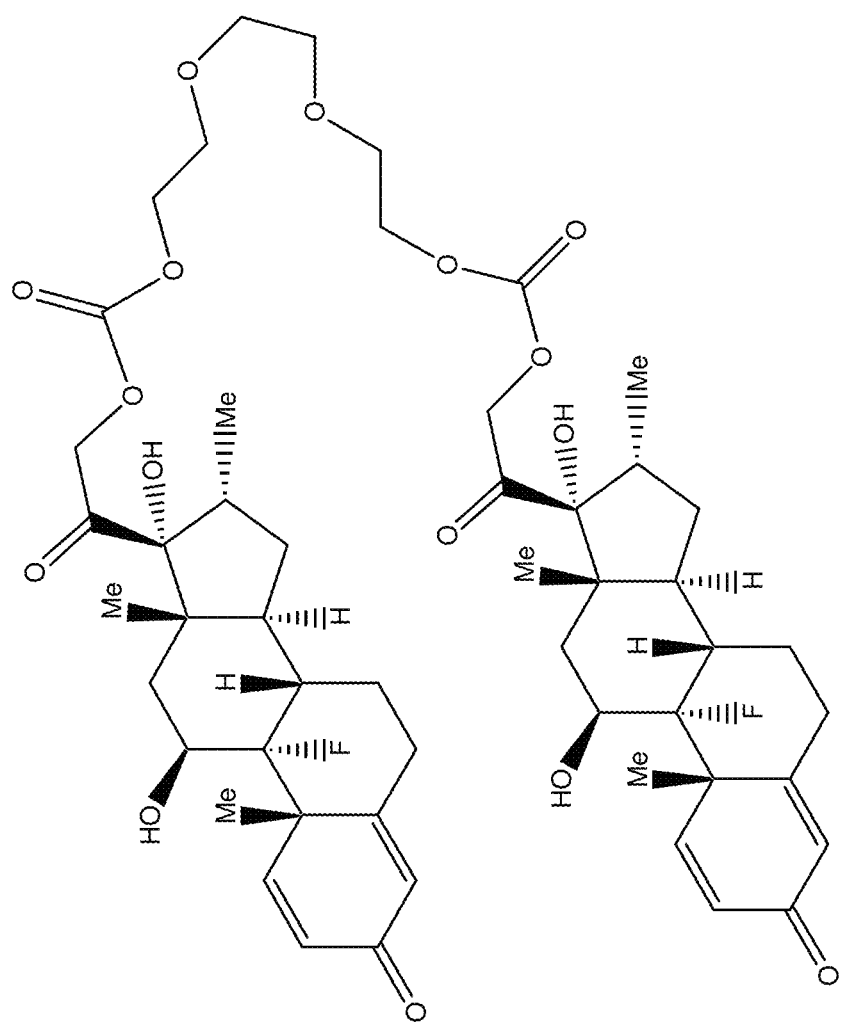

While the clinical importance of sustained drug release delivery systems to maintain therapeutic concentration of drugs for extended periods of time (e.g., days to weeks, to months or even years) has been well acknowledged for decades, there has been a limited number of successfully commercialized products on the market to date. It is recognized in this disclosure that to develop successful sustained drug delivery systems, technical difficulties must be overcome ranging from drug degradation during formulation process; lack of controlled release, including unwanted burst or incomplete release associated with diffusion or bulk erosion mechanisms of drug release; low encapsulation efficiency; and formulation complexity.

For locally administered sustained release delivery systems, it is recognized in this disclosure that additional challenges can arise where the mass balance of the carrier or matrix for the drug hinders drug loading, or where the carriers and matrices produce unwanted effects (i.e., such as local inflammation). It is recognized in this disclosure that there is an unmet need for a sustained release drug system that is formulated to release dexamethasone via a surface erosion process in the absence or with a minimal amount of carrier and/or excipient agents, at a rate-controlled manner over an extended period of time (e.g., days to weeks, to months or even years), where the system contains predominantly dexamethasone prodrug and minimizes side effects associated with the use of carriers or matrices.

This disclosure describes dexamethasone prodrug dimers that can be in a crystalline or amorphous form and have unique properties that allow them to be processed as viscous fluids from a melt or solution, in order yield shaped articles where most of the material is in a glassy state. The shaped articles may be held together by secondary (e.g., non-crystalline) interactions and have the ability to release their prodrug/drug elements from these shaped forms upon surface mediated degradation/dissolution. This may provide a controlled rate of drug release over days, weeks, months, or years, due to unique interactions between the molecules that exist in a mostly amorphous state while holding the shaped form intact as the surface erodes. This disclosure may alter the need for a carrier matrix to provide shape and form to a drug delivery depot or device, and therefore, may mitigate the issues of phase separation of drug from the matrix, and incompatible processing conditions between the formulations' components. Further, such materials can minimize inflammatory responses because the drugs/prodrugs undergoing surface erosion from the shaped article can be released in the biological environment in a non-particulate (e.g., non-crystalline) form and can have inherent anti-inflammatory activity from the drugs being released from the prodrug shaped form.

The compounds of the disclosure can be designed for the controlled and sustained release of dexamethasone from the dexamethasone prodrug dimer used to make the shaped article. Articles formed from the compounds of the disclosure can yield sustained and uniform release of the dexamethasone prodrugs, without exhibiting any burst release (e.g., $t_{10}$ can be equal to or greater than $\frac{1}{10}$ of $t_{50}$) and without reliance upon degradable matrices, which can cause undesirable local side effects (such as inflammation). The high drug loading that can be present in the articles of the disclosure are suitable for producing locally effective concentrations of a dexamethasone for periods of days to weeks to months or even years.

Compounds
The disclosure described herein features a compound of formula (I):
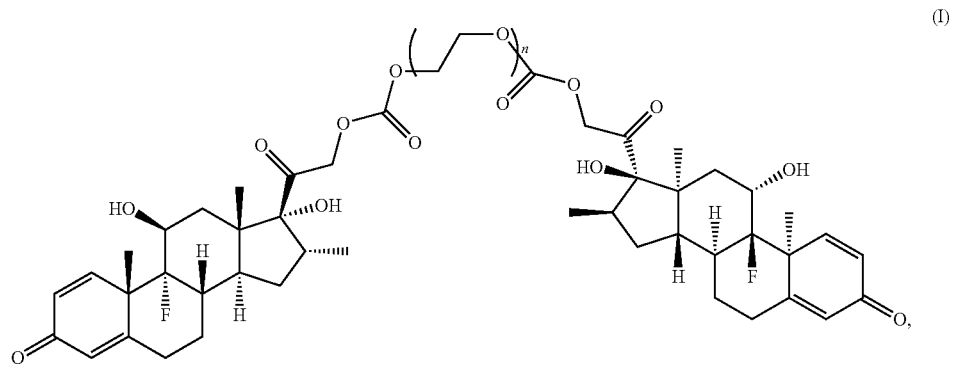
wherein n is an integer from 1 to 6.
In some embodiments, the compound is Compound 1:
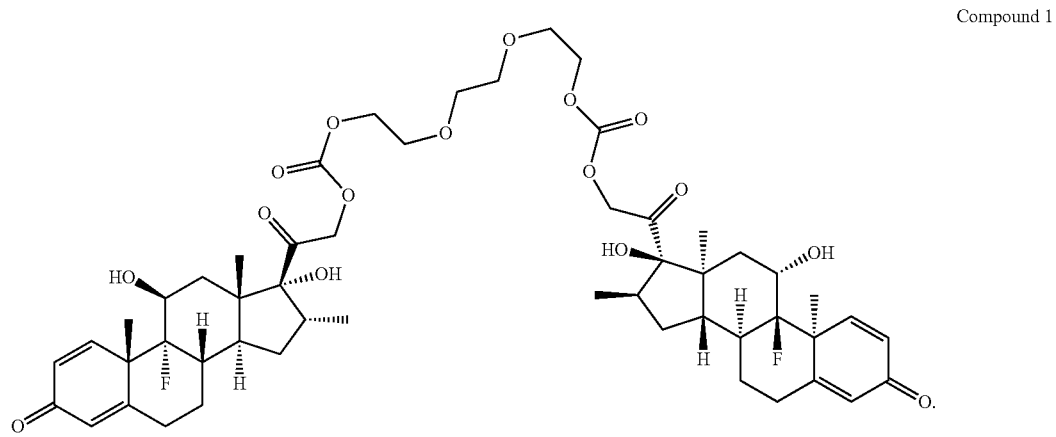
In some embodiments, the compound is Compound 2:
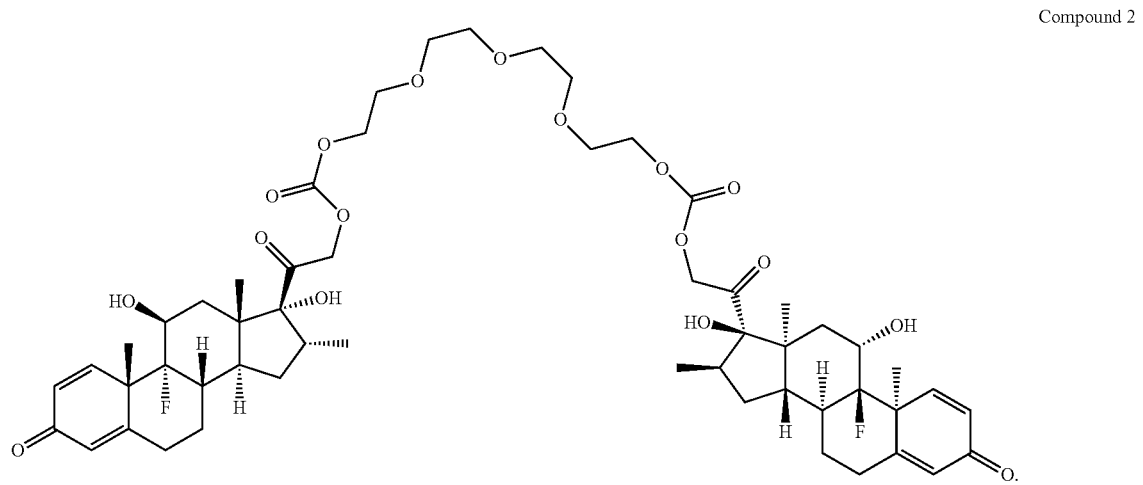

In some embodiments, the compound is Compound 3:

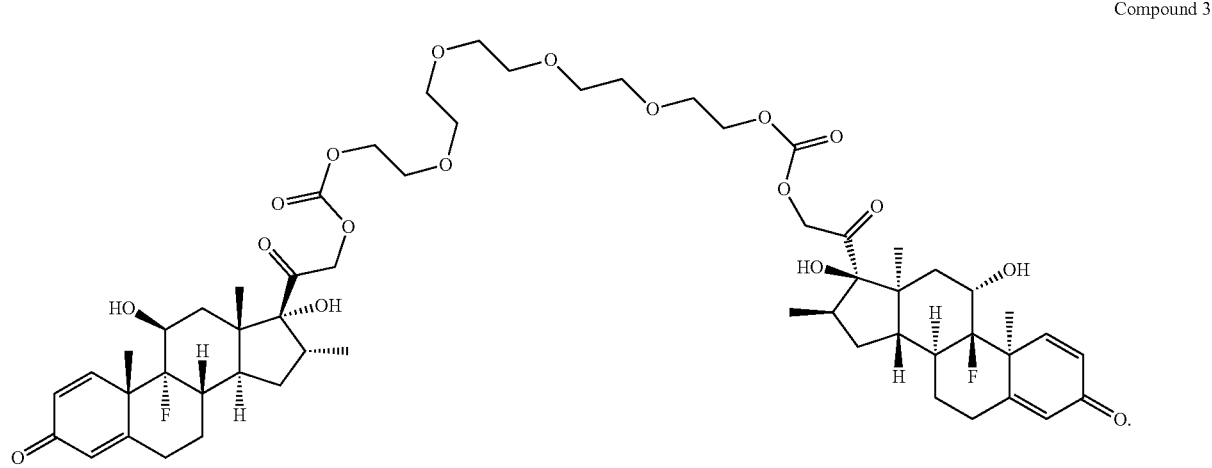

Compound 3

The disclosure also features Compound 6:

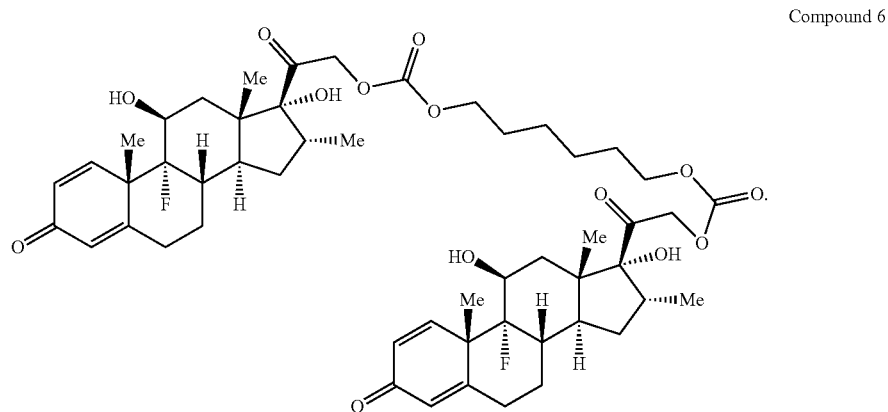

Compound 6

Formulations

The pharmaceutical compositions of the disclosure can include an article in the form of fibers, fiber meshes, woven fabrics, non-woven fabrics, pellets, cylinders, hollow tubes, microparticles (e.g., microbeads), nanoparticle (e.g., nanobeads), or other shaped articles. In some embodiments, the pharmaceutical composition of the disclosure has a non-circular shape that affects, e.g., increases, the surface area (e.g., extruded through star-shaped dye). Suitable pharmaceutical compositions for use with this disclosure can be small regularly or irregularly shaped particles, which can be solid, porous, or hollow.

Different forms of pharmaceutical compositions of the present disclosure (e.g., fibers, fiber meshes, woven fabrics, non-woven fabrics, pellets, cylinders, hollow tubes, microparticles (e.g., microbeads), nanoparticles (e.g., nanobeads), or other shaped articles) can have the advantages of providing a controllable surface area, being easily injected, not requiring removal after completion of drug release, and allow for tailoring drug release rates required for a given indication. When used as an injectable drug delivery device, drug release rate and interaction with cells are strongly dependent on the size distribution of the pharmaceutical composition form.

Processing Methods

Articles of the disclosure can be formed using any number of the methods, for example, heat processing or solvent processing of the dexamethasone prodrug dimer of formula (I). Heat processing can include heat molding, injection molding, extrusion, 3D printing, melt electrospinning, fiber spinning, fiber extrusion, and/or blow molding. Solvent processing may include coating, micro printing, emulsion processing dot printing, micropatterning, fiber spinning, solvent blow molding, electrospraying, and electrospinning.

Electrospraying Method

In some embodiments, the pharmaceutical compositions of the disclosure are dissolved in a solvent (e.g., acetone) at concentrations ranging from, e.g., 10-30% w/v, and are electrosprayed to form micro- and nanobeads. The solutions can be loaded into a syringe and can be injected at a particular rate, e.g., 0.5 mL/h, onto a stationary collection plate. Between the needle and collecting surface, a potential difference of, e.g., 18 kV, can be maintained. Exemplary concentration of 10% w/v is used to obtain nanoparticles. In other embodiments, a concentration of 30% w/v is used to obtain microbeads.

Fiber Spinning Methods

In some embodiments, the pharmaceutical compositions of the disclosure, e.g., fibrous meshes with aligned and unaligned morphologies are prepared by electrospinning. The pharmaceutical compositions of the disclosure are dissolved in a solvent (e.g., THF, or 1:1 ratio of DCM/THF). The solutions may be injected from a syringe at a particular rate, e.g., 0.5 mL/h, onto a cylindrical mandrel rotating at a particular rotational speed, e.g., 1150 rpm, to obtain aligned fibers, or onto a stationary collector surface to obtain unaligned fibers. A potential difference (e.g., 18 kV or 17 kV) can be maintained between the needle and collecting surface for aligned and random fibers.

In other embodiments, fibers are prepared either from the melt at elevated temperatures, the glassy state intermediate, or from solution by dissolving the pharmaceutical compositions of the disclosure in a solvent (e.g., DCM, THF, or chloroform). As used herein, melt spinning describes heat processing from the melt state, heat spinning describes heat processing from the glassy state, and wet, dry, and gel spinning describe solution processing.

The viscous melt, intermediate, or solution can be fed through a spinneret and fibers may be formed upon cooling (melt or heat spinning) or following solvent evaporation with warm air as the compound exits the spinneret (dry spinning). Wet spinning and gel spinning, performed according to methods known in the art, may also be used to produce the fibers of the disclosure. Heat spinning describes a process that is essentially the same as the melt spinning process, but performed with the glassy state intermediate and heated above the glass transition temperature (Tg) to get the viscous fluid to extrude/spin instead of the melt. Alternatively, tweezers may be dipped into melted material or concentrated solutions and retracted slowly in order to pull fibers. The rate of pulling and distance pulled may be varied to yield fibers and columnar structures of different thickness.

Emulsion Method

In some embodiments, micro-particles or nano-particles made from the pharmaceutical composition can be formed using an emulsion process. The pharmaceutical composition may be dissolved in an organic solvent (e.g., DCM, THF, etc.) and a surfactant (e.g., SDS, PVA, etc.) may be added to the solution/mixture at a low percentage (e.g., 1%). The resulting mixture may be stirred for the appropriate time at room temperature to form an emulsion. The emulsion may be subsequently added to Milli-Q water under stirring for an appropriate time (e.g., 1 h) to remove residual solvent. The resulting micro- or nano-particles may be collected by centrifugation and dried to obtain the desired form.

Extrusion Method

In some embodiments, injectable cylinders made from the pharmaceutical composition may be formed by heat extrusion. The pharmaceutical composition may be loaded into a hot melt extruder, heated to a temperature above the melting point (for crystalline compositions) or glass transition temperature (for pre-melted or amorphous compositions), and extruded using a light compressive force to push the material through the nozzle and a light tensile force to pull the material out of the extruder. The extrudate may be cut to the desired length for appropriate drug dosing for the indication of interest.

Bead Sizing and Milling

In some embodiments, a milling process may be used to reduce the size of an article of the disclosure to form sized particles, e.g., beads, in the micrometer (microbeads) to nanometer size range (nanobeads). The milling process may be performed using a mill or other suitable apparatus. Dry and wet milling processes such as jet milling, cryo-milling, ball milling, media milling, sonication, and homogenization are known and can be used in methods described herein. Generally, in a wet milling process, a suspension of the material to be used as the core is agitated with or without excipients to reduce particle size. Dry milling is a process wherein the material to be used as the article core is mixed with milling media with or without excipients to reduce particle size. In a cyro-milling process, a suspension of the material to be used as the core is mixed with milling media with or without excipients under cooled temperatures. In some embodiments, subsequent heating of the milled microparticle above the Tg is needed to achieve a spherical shape, or particles with non-spherical shapes can be used as milled.

Low Temperature Processing Using Intermediate Glassy State Articles

In certain embodiments, the dexamethasone prodrug dimer has a limited window (e.g., short timeframe of seconds to minutes) of thermal stability, whereby the purity of the dimer is minimally affected at elevated temperatures. In some embodiments, it is beneficial to make an intermediate glassy state form (e.g., film, pellet, micro-particles, or other shaped article). This can be accomplished by heat or solvent processing to remove or reduce the crystallinity of the material to form a glassy state composition. The glassy state composition is subsequently heat processed at a lower temperature (e.g., processing just above the glass transition temperature (Tg), and below the melt temperature (Tm)). This can provide a longer timeframe for heat processing the glassy state material into the final shaped article, while reducing the impact of processing conditions on the purity of the dexamethasone prodrug dimer in the article.

Exemplary processing details are provided in the Examples.

Drug Delivery

The pharmaceutical compositions of the disclosure provide optimal delivery of dexamethasone they release the dexamethasone from an article of the disclosure in a controlled manner, for example, by surface erosion. The surface erosion mechanism of drug release may allow the shaped article to maintain its physical form (e.g. shape/geometry of the article), while gradually decreasing in size as the surface erodes (e.g., like a bar of soap), rather than bulk erosion that is characteristic of some polymer-based drug release vehicles (e.g. polylactic/glycolic acid). This may inhibit burst release and reduce the formation of inflammatory particulates (e.g., no crystalline particulates are formed when drug is released in the manner described herein). The drug can be controlled to be delivered over a desired period of time. A slower and steadier rate of delivery may in turn result in a reduction in the frequency with which the pharmaceutical composition must be administered to a subject, and improve the safety profile of the drug. Drug release can also be tailored to avoid side effects of slower and longer release of the drug by engineering the article to provide steady release over a comparatively shorter period of time.

The rate of release of a given drug from a dexamethasone prodrug dimer may also depend on the quantity of the loaded drug dimer as a percent of the final drug dimer formulation, e.g., by using a pharmaceutical excipient that acts as a bulking agent. Another factor that can affect the release rate of a drug from, for example a microbead, is the microbead size. In some embodiments, drug release is tailored based on the solubility of dexamethasone prodrug dimer (e.g., through selection of appropriate linker) that will influence the rate of surface erosion (e.g., dissolution/degradation)

from the article. In other embodiments, drug release is affected by changes in surface area of the formulation, e.g., by changing the diameter of the microbeads. By adjusting the vide supra factors, dissolution, degradation, diffusion, and controlled release may be varied over wide ranges. For example, release may be designed to be initiated over minutes to hours, and may extend over the course of days, weeks, months, or years.

Uses and Pharmaceutical Compositions

In some embodiments, the dexamethasone prodrug dimers of the disclosure are used as a drug delivery device (or, e.g., a drug depot) with a minimal need for additives. This may achieve a local, sustained release and a local biological effect, while minimizing a systemic response. In some embodiments, when present, the additives are in small amounts and do not affect the physical or bulk properties. In some embodiments, when present, the additives do not alter the drug release properties from the pharmaceutical composition but rather act to improve processing of the prodrug dimer into the shaped article. In some embodiments, the pharmaceutical compositions contain additives such as a plasticizer (e.g., to reduce thermal transition temperatures), an antioxidant (e.g., to increase stability during heat processing), a binder (e.g., to add flexibility to the fibers), a bulking agent (e.g., to reduce total drug content), a lubricant, a radio-opaque agent, or mixtures thereof. The additives may be present at 30% (w/w), e.g., 20% (w/w), 10% (w/w), 7% (w/w), 5% (w/w), 3% (w/w), 1% (w/w), 0.5% (w/w), or 0.1% (w/w). Examples of plasticizers are polyols, e.g., glycerol, ethylene glycol, diethylene glycol, triethylene glycol, tetraethylene glycol, polyethylene glycol, propylene glycol, triacetin, sorbitol, mannitol, xylitol, fatty acids, monosaccharides (e.g., glucose, mannose, fructose, sucrose), ethanolamine, urea, triethanolamine, vegetable oils, lecithin, or waxes. Exemplary antioxidants are glutathione, ascorbic acid, cysteine, or tocopherol. The binders and bulking agents can be, e.g., polyvinylpyrrolidone (PVP), starch paste, pregelatinized starch, hydroxypropyl methyl cellulose (HPMC), carboxymethyl cellulose (CMC), or polyethylene glycol (PEG) 6000.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an agent even though such agent does not treat the cause of the pain).

Pharmaceutical compositions containing the dexamethasone prodrug dimers described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), buccal and inhalational administration. Desirably, the articles of the disclosure are administered parenterally as injections (intravenous, intramuscular, or subcutaneous), or locally as injections (intraocularly or into a joint space). The formulations are admixed under sterile conditions with a pharmaceutically acceptable carrier or suspension or resuspension agents (e.g., for micro- and nanoparticles) and any needed preservatives or buffers as may be required.

The articles of the disclosure described herein including a dexamethasone prodrug dimer may be administered to a subject to be delivered in an amount sufficient to deliver to a subject a therapeutically effective amount of an incorporated pharmaceutical agent as part of prophylactic or therapeutic treatment, or as a part of adjunctive therapy to avoid side-effects of another drug or therapy. In general, an effective amount of a pharmaceutical agent or component refers to the amount necessary to elicit the desired biological response. The desired concentration of pharmaceutical agent in the article of the disclosure will depend on numerous factors, including, but not limited to, absorption, inactivation, and excretion rates of the drug as well as the delivery rate of the compound from the subject compositions, the desired biological endpoint, the agent to be delivered, the target tissue, etc. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The concentration and/or amount of any pharmaceutical agent to be administered to a subject may be readily determined by one of ordinary skill in the art. Known methods are also available to assay local tissue concentrations, diffusion rates from dexamethasone prodrug dimers and local blood flow before and after administration of the therapeutic formulation.

Sterilization of Formulations

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, articles of the disclosure may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Treatment Methods

The formulations of the disclosure may be used in the fields of ophthalmology, oncology, laryngology, endocrinology and metabolic diseases, rheumatology, urology, neurology, cardiology, dental medicine, dermatology, otology, post-surgical medicine, and orthopedics.

Ophthalmic Uses

In certain embodiments, the articles of the disclosure may be used prevent, treat or manage diseases or conditions at the back of the eye, such as at the retina, macula, choroid, sclera and/or uvea.

In some embodiments, the articles of the disclosure are used as injectable drug delivery devices for ophthalmology (e.g., intravitreal injection, coating on a minimally invasive glaucoma surgery (MIGS) devices, or implant in blebs). During an intravitreal injection a medication is placed directly into the space in the back of the eye called the vitreous cavity, which is filled with a jelly-like fluid called the vitreous humor gel. Intravitreal injections may be used to treat retinal diseases such as diabetic retinopathy, macular degeneration, macular edema, uveitis, and retinal vein occlusion.

In certain embodiments, the articles of the disclosure may be used to treat, prevent, or manage an ocular condition, i.e., a disease, ailment, or condition that affects or involves the eye or one or more of the parts or regions of the eye. In some embodiments, the articles of the disclosure may be used to treat, prevent, or manage an ocular condition at the front of the eye of a subject. A front of the eye ocular condition includes a disease, ailment or condition, such as for example, post-surgical inflammation; uveitis; infections; aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; corneal neovascularization; refractive disorders and strabismus. In some embodiments, articles of the disclosure may be used to treat, prevent, or manage an ocular condition at the back of the eye of a subject. A posterior ocular condition can include a disease, ailment, or condition, such as intraocular melanoma; acute macular neuroretinopathy; Behcet's disease; choroidal neovascularization; uveitis; diabetic uveitis; histoplasmosis; infections, such as fungal or viral-caused infections; macular degeneration, such as acute macular degeneration, non-exudative age related macular degeneration and exudative age related macular degeneration; edema, such as macular edema (e.g., cystoid macular edema (CME) and diabetic macular edema (DME)); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. In some embodiments, the articles of the disclosure may be used to treat, prevent, or manage dry eye in a subject. In some embodiments, the articles of the disclosure may be used to treat, prevent, or manage inflammation in the eye of a subject. Inflammation is associated with a variety of ocular disorders. Inflammation may also result from a number of ophthalmic surgical procedures, including cataract surgery. In some embodiments, the pharmaceutical agent that is delivered into the eye by the articles of the disclosure and/or methods described herein may be a corticosteroid. In some embodiments, the dexamethasone prodrug dimers of the disclosure are used as adjunctive therapy to reduce inflammation and fibrosis associated with devices (e.g., minimally invasive glaucoma surgery (MIGS) devices). In some embodiments, articles of the disclosure may be used to treat, prevent, or manage age-related macular degeneration (AMD) in a subject.

Osteoarthritis Treatment

In some embodiments, the articles of the disclosure are used for the treatment of osteoarthritis (OA). For OA of the knee, intraarticular (IA) injection (e.g., steroids) is preferred as the last non-operative modality, if other conservative treatment modalities are ineffective. Steroids may be used to reduce inflammation in tendons and ligaments in osteoarthritic joints. IA steroid injections provide short term reduction in OA pain and can be considered as an adjunct to core treatment for the relief of moderate to severe pain in people with OA. Dexamethasone can be used in the treatment of OA. In some embodiments, microspheres of the disclosure composed of the dexamethasone prodrug dimers are injected into a knee joint for the treatment of OA.

Surgical Procedures

In some embodiments, the articles of the disclosure are used in conjunction with a surgical procedure. For example, an article of the disclosure can be implanted at a surgical site to reduce the risk of inflammation treated by the surgical procedure, or can be used as an adjunctive to reduce the risk of infection.

EXAMPLES

The following examples are put forth to provide those of ordinary skill in the art with a description of how the compositions and methods described herein may be used, made, and evaluated, and are intended to be purely exemplary of the disclosure and are not intended to limit the scope of what the inventors regard as their disclosure.

Compounds 1-8 can be used in the compositions, methods, and articles of the disclosure.

TABLE 1

Compounds of the disclosure

| Compound | Dimer | Abbreviation |
|---|---|---|
| 1 | Dexamethasone-Triethylene Glycol-Dexamethasone | Dex-TEG-Dex |
| 2 | Dexamethasone-Tetraethylene Glycol-Dexamethasone | Dex-EG4-Dex |
| 3 | Dexamethasone-Pentaethylene Glycol-Dexamethasone | Dex-EG5-Dex |
| 4 | Dexamethasone-Heptaethylene Glycol-Dexamethasone | Dex-EG7-Dex |
| 5 | Dexamethasone-Nonaethylene Glycol-Dexamethasone | Dex-EG9-Dex |
| 6 | Dexamethasone-Hexane-Dexamethasone | Dex-HEX-Dex |
| 7 | Dexamethasone-Polyethylene Glycol (MW = 200)-Dexamethasone | Dex-PEG200-Dex |
| 8 | Dexamethasone-Polyethylene Glycol (MW = 300)-Dexamethasone | Dex-PEG300-Dex |

Example 1: Compound 1 (Dexamethasone-Triethylene Glycol-Dexamethasone) can be Synthesized, Processed into Pellets in the Glassy State by Heat Molding, and Release Drug Through Surface Erosion from an Intact Pellet Dexamethasone (1 mol equivalent) was suspended in dichloromethane on an ice bath and triethylamine (2 mol equivalent) and triethylene glycol bis(chloroformate) (0.6 mol equivalent) were added to the mixture. The ice bath was allowed to warm to room temperature and the reaction was stirred overnight. The solvent was removed and the solid residue was purified by column chromatography. Product was recrystallized twice from acetonitrile to give Compound 1 (FIG. 1A) as an off-white crystalline solid.

Compound 1: HPLC (mobile phase: $H_2O$/TFA and MeCN/TFA) 31.7 min; Elemental analysis: Anal. Calcd for $C_{52}H_{68}F_2O_{16}$: C, 63.27; H, 6.94; N, 0.00; Cl, 0.00. Found: C, 62.62; H, 6.84; N, <0.50; Cl, <100 ppm. $^1$H NMR (400 MHz, DMSO-$d_6$) δ (ppm) 0.80 (d, J=7 Hz, 6H, 2×C16

α-CH$_3$); 0.90 (s, 6H, 2×C18-CH$_3$); 1.08 (m, 2H, 2×C16-H); 1.35 (m, 2H, 2×C14-H); 1.49 (s, 6H, 2×C19-CH$_3$); 1.54 (q, J=13 Hz, 2H, 2×C13-H); 1.64 (q, J=11 Hz, 2H, 2×C15-CH$_2$); 1.77 (m, 2H, 2×C15-CH$_2$); 2.15 (m, 4H, 2×C6-CH$_2$); 2.32 (m, 4H, 2×C7-CH$_2$); 2.62 (m, 2H, 2×C12-CH$_2$); 2.89 (m, 2H, 2×C12-CH$_2$); 3.57 (s, 4H, 2×TEG OCH$_2$); 3.65 (m, 4H, 2×TEG OCH$_2$); 4.15 (m, 2H, 2×OCH); 4.22 (m, 4H, 2×TEG OCH$_2$); 4.79 (d, 2H, AB, J=18.5 Hz, 2H, C21-CH$_2$O—); 5.09 (d, 2H, AB, J=18.5 Hz, 2H, C21-CH$_2$O—); 5.18 (s, 2H, C17-OH); 5.40 (d, 2H, J=4.5 Hz, C11-OH); 6.01 (d, 2H, J=1.9 Hz, 2×alkene C4-CH); 6.23 (dd, 2H, J=10.1 and 1.9 Hz, 2×alkene C2-CH); 7.29 (d, 2H, C1-CH 2×alkene CH, 10.1 Hz, 2H). MS (ESI+) m/z: [M+H]+Calcd for C$_{52}$H$_{69}$F$_2$O$_{16}$ 987.46. Found 987.46.

Figure 1C:
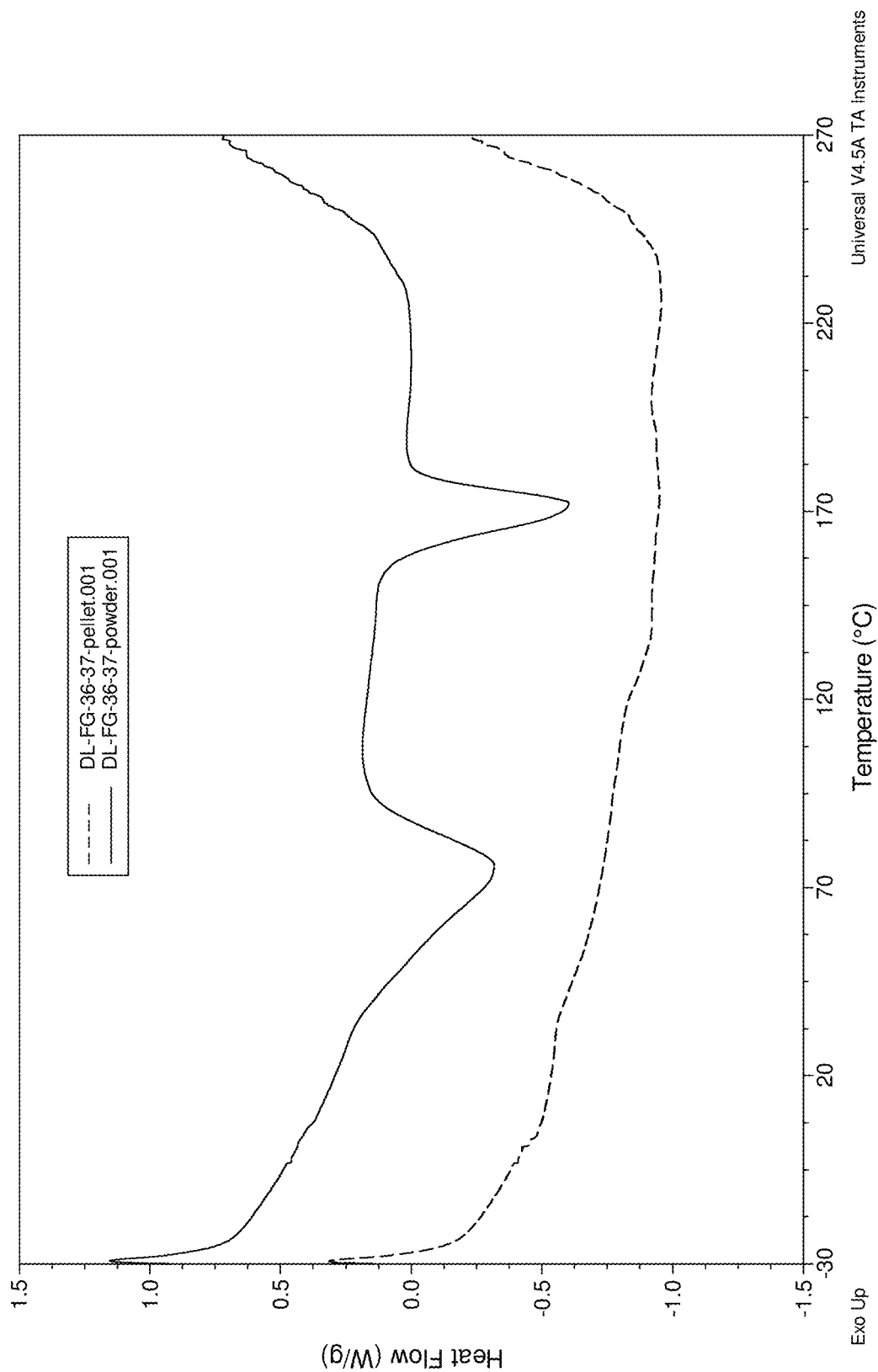
Figure 1D:
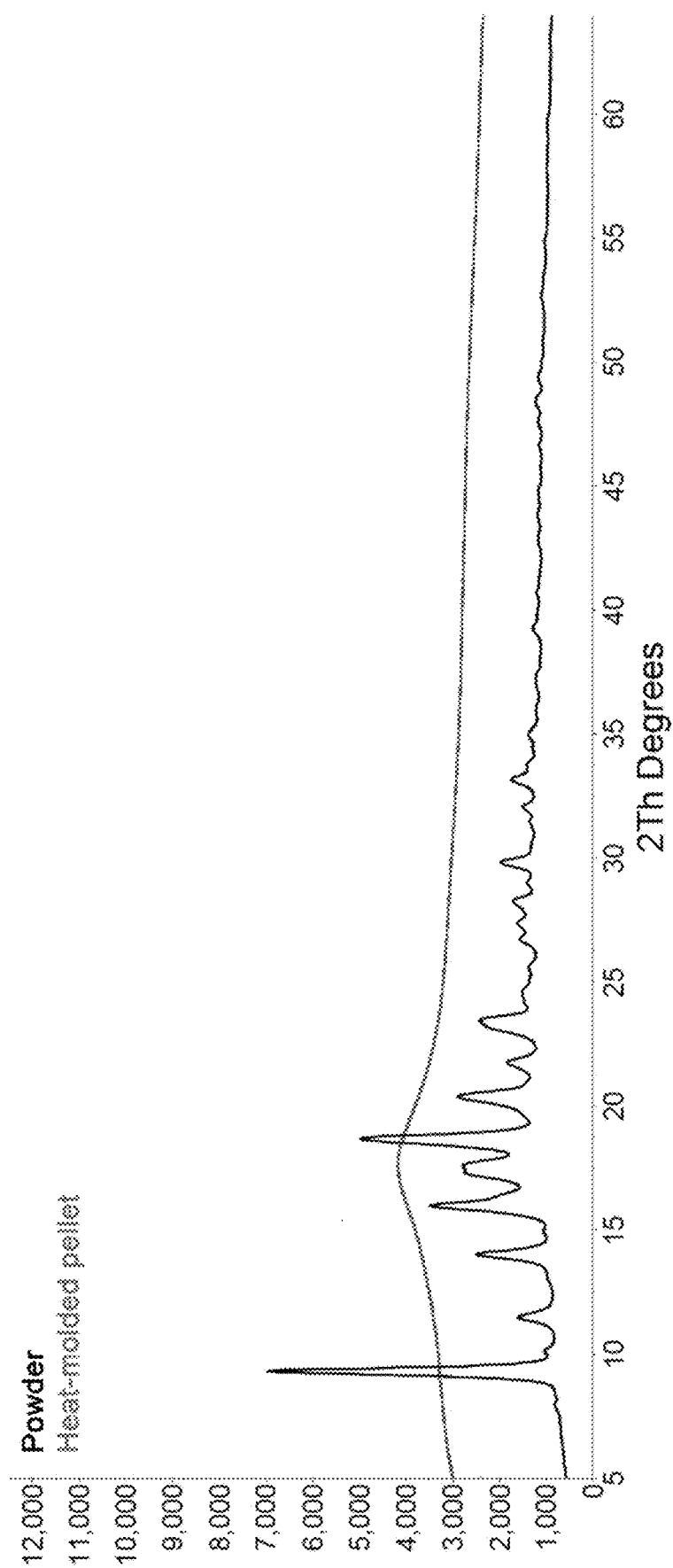

Compound 1 was formed into pellets in the glassy state by heat molding (FIG. 1B). Crystalline powder was melted at 185° C. and pellets were formed from 1 mm×1 mm cylindrical molds. The starting powder and heat-processed pellets were tested by differential scanning calorimetry (DSC; FIG. 1C) and X-ray powder diffraction (XRPD; FIG. 1D) to confirm heat-processing converted Compound 1 from the crystalline state to the glassy state.

Heat-molded pellets from Compound 1 (~1 mm×1 mm) were then placed in 20 mL glass vials and 2 mL of release buffer (either 100% phosphate buffered saline (PBS), 1% fetal bovine serum (FBS) in PBS, or 100% FBS) was added. Samples were incubated at 37° C. on a shaker rotating at 115 rpm. After 1 day, 3 days, 7 days, and subsequently in alternating 3 and 4 day intervals (i.e., 1, 3, 7, 10, 14 days etc.), release buffer was sampled directly (PBS) or syringe filtered, proteins were precipitated with acetonitrile, and drug release products were extracted. The samples were analyzed by high performance liquid chromatography (HPLC) to quantify drug products. Cumulative drug release was calculated and plotted as a percentage of the total drug in each pellet released over time (FIG. 1E). Representative images of the pellets confirm surface erosion over time in 100% FBS (FIG. 1F)

Figure 2C:
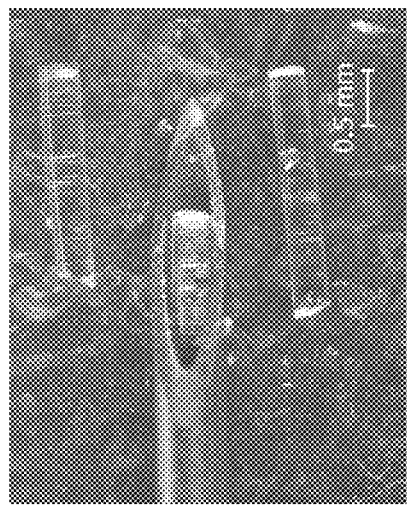
FIGS. 2A-2E are a series of images showing Compound 1 processed into heat-molded pellets (FIG. 2A), extruded cylinders (FIGS. 2B and 2C), glass droplets (FIG. 2D), and fibers (FIG. 2E).
Figure 2B:
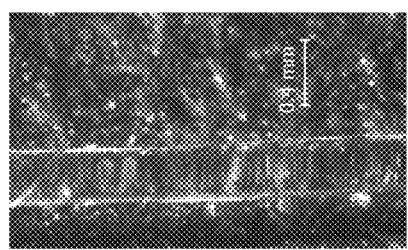
Figure 2A:
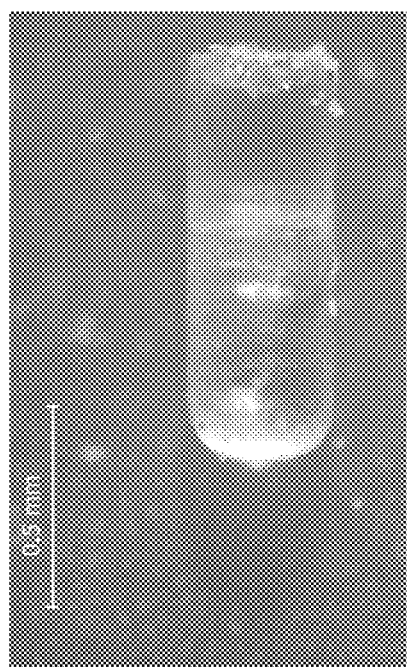
Figure 2E:
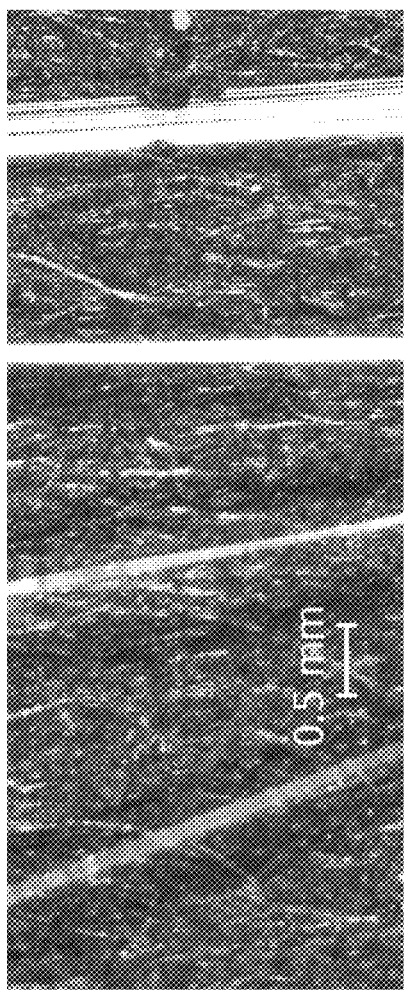
Figure 2D:
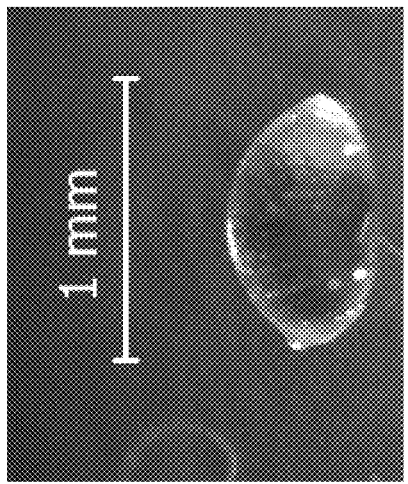

Example 2: Compound 1 (Dex-TEG-Dex) can be Processed into Different Forms in the Glassy State by Multiple Processing Methods from the Melt State Compound 1 was processed into different forms in the glassy state from the melt state. Heat-molded pellets (FIG. 2A) were prepared as described in Example 1 with a cylindrical mold (~0.34 mm diameter and 0.85 mm length). Extruded cylinders (FIG. 2B) were prepared by adding Compound 1 as a crystalline powder into a micro-extruder with different nozzles to form extruded material of different diameters. The micro-extruder was heated to 185° C. to melt the powder and form the extrudate. FIG. 2C shows an extruded cylinder with a 23 G diameter nozzle, cut, and loaded into a 23 G needle. Glass droplets (FIG. 2D) were formed by dispersing Compound 1 as a powder on PTFE sheet and heating it to 185° C. Fibers of Compound 1 were prepared by heat extrusion at 185° C. using a small diameter nozzle (e.g. 30-32 G) combined with a tensile force to pull the extrudate out of the nozzle. Fibers were also prepared by melting Compound 1 from a powder at 185° C. and by pulling the melted material at different rates to yield fibers of different diameters (FIG. 2E).

Figure 3B:
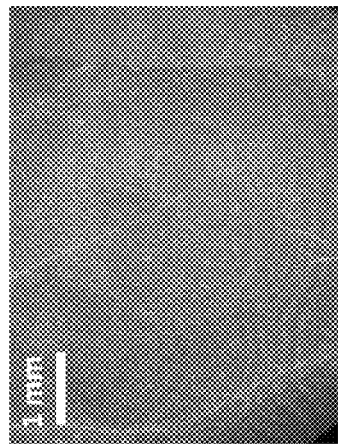
Figure 3A:
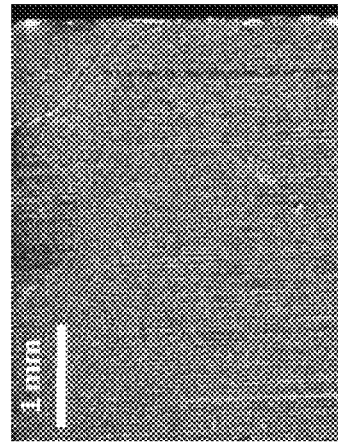

Example 3: Compound 1 (Dex-TEG-Dex) can be Processed into Different Forms in the Glassy State by Multiple Processing Methods from the Solution State Compound 1 was processed into different forms in the glassy state, including coatings, non-woven fibrous meshes, fibers, and micro- and nano-particles, from the solution state using organic solvents. Compound 1 was coated onto titanium (FIG. 3A) and poly(styrene-block-isobutylene-block-styrene) (SIBS) surfaces (FIG. 3B) from acetone by drop coating and can be coated using other common techniques (e.g., dip-coating, spray coating, electrospraying, etc.).

Figure 3C:
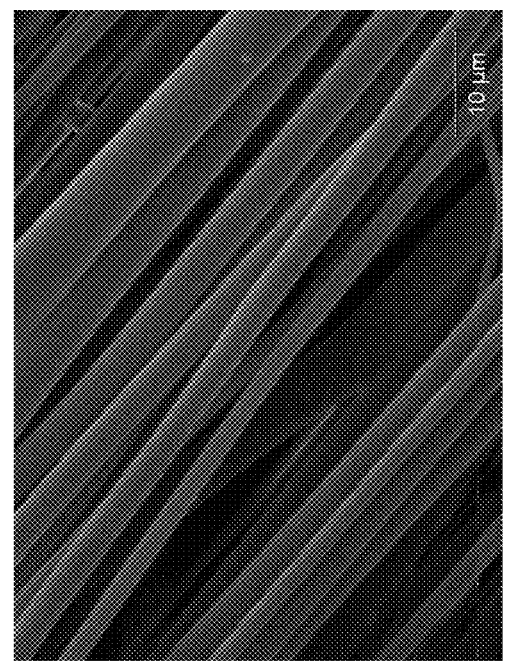
Figure 3C:
Figure 3D:
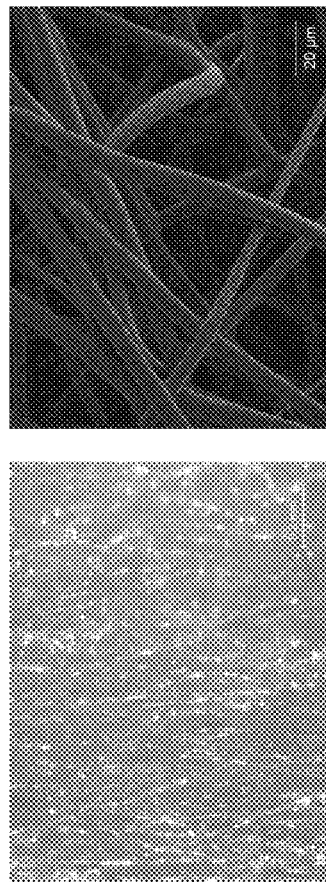
Figure 3E:
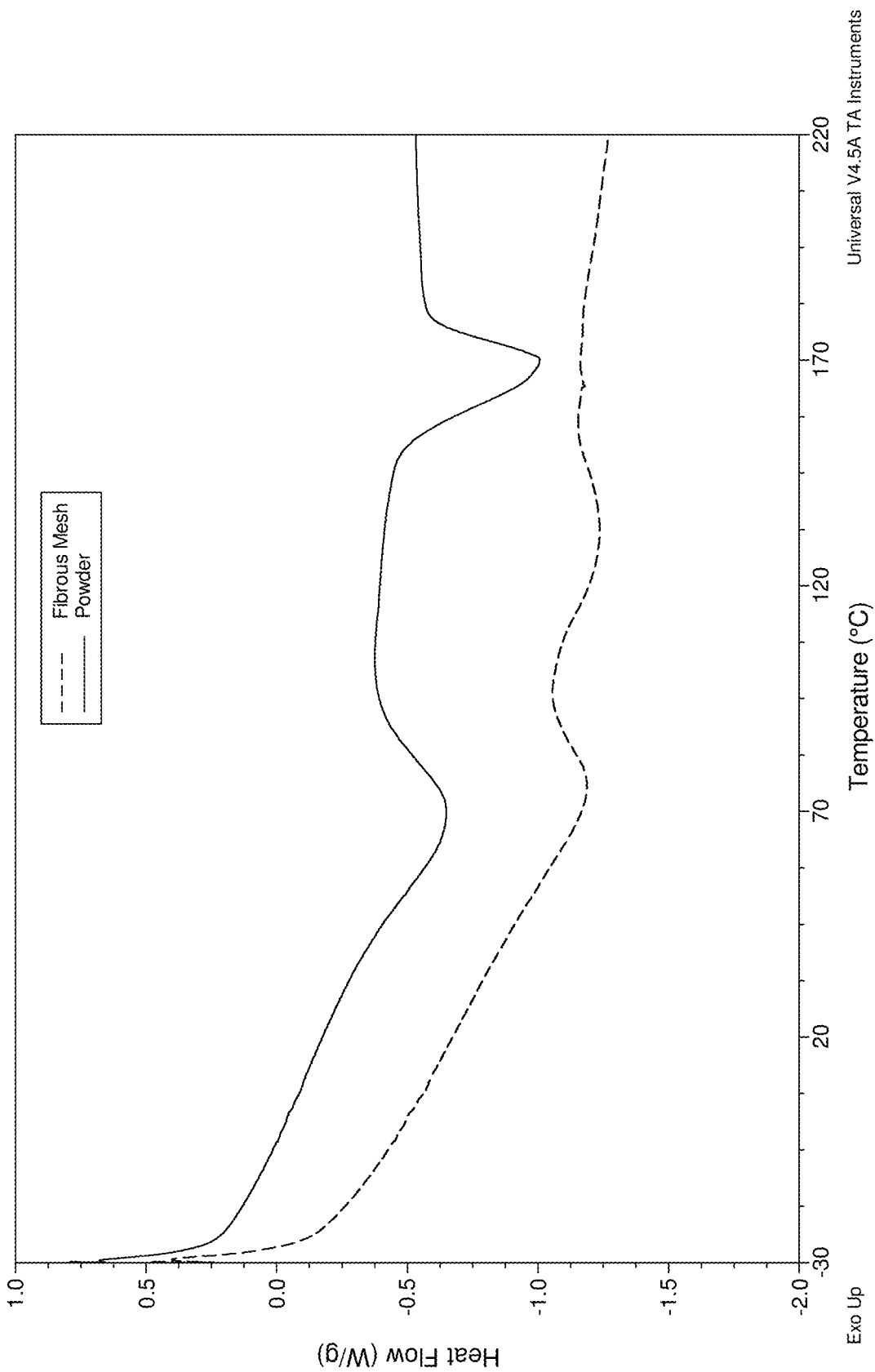
Figure 3F:
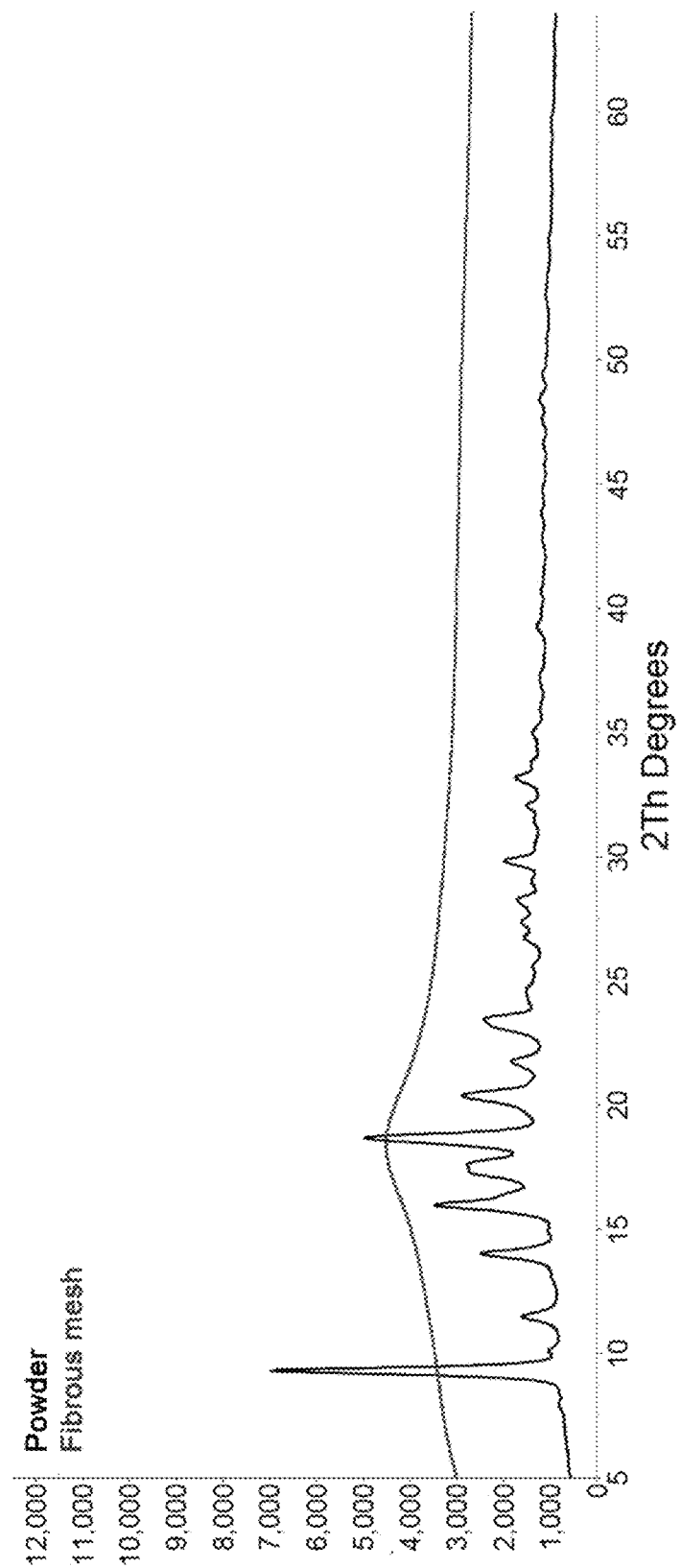

Non-woven fibrous meshes with aligned (FIG. 3C) and unaligned (FIG. 3D) morphologies were prepared by electrospinning. Compound 1 was dissolved in tetrahydrofuran (THF) and was electrosprayed onto a cylindrical rotating mandrel to obtain aligned fibers or onto a stationary collector surface to obtain unaligned fibers. Compound 1 as the starting powder and solvent-processed fibrous mesh were tested by DSC (FIG. 3E) and XRPD (FIG. 3F) to confirm the meshes were in the glassy state.

Figure 3G:
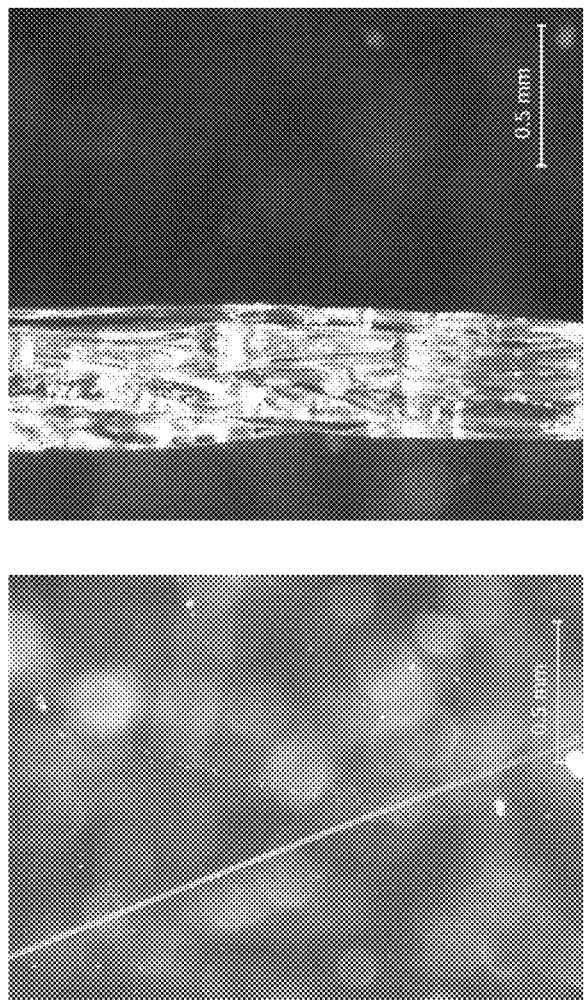

Fibers (FIG. 3G) were prepared by dissolving Compound 1 in dichloromethane (DCM), THF, or chloroform and by pulling Compound 1 from the solution. The rate of pulling and distance pulled were varied to yield fibers and columnar structures of different thickness.

Figure 3H:
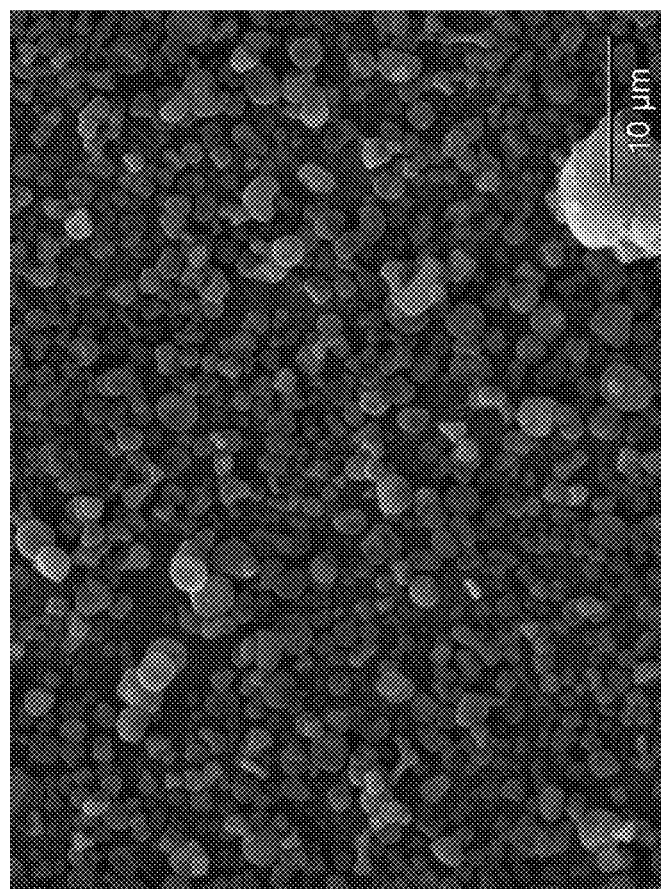
Figure 3I:
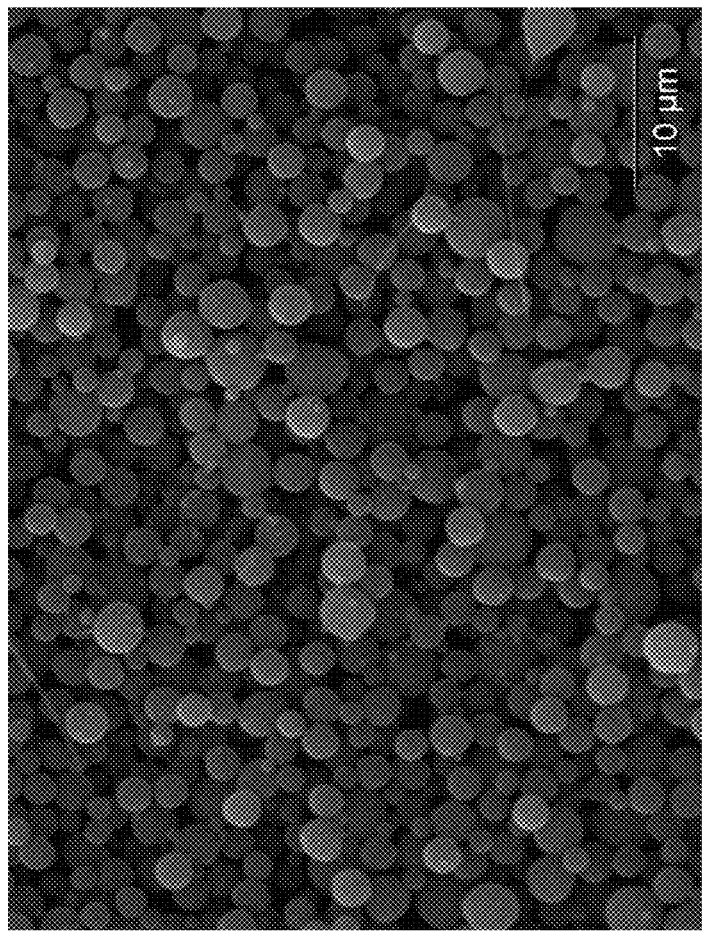

Electrosprayed micro- and nano-particles were prepared by dissolving Compound 1 in acetone. A concentration of 10% w/v was used to electrospray Compound 1 into nanoparticles (FIG. 3H), while a concentration of 30% w/v was used to electrospray Compound 1 into microparticles (FIG. 3I).

Figure 3J:
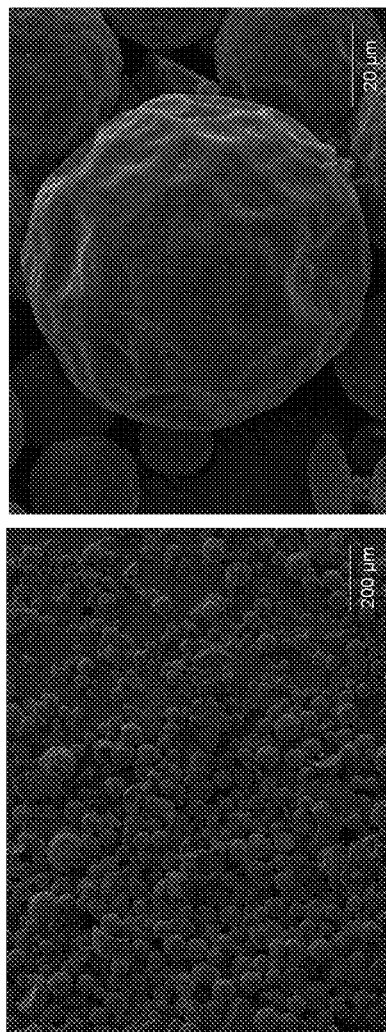

Micro-particles of Compound 1 were prepared by emulsion from DCM using sodium dodecyl sulfate (FIG. 3J). The microparticles were analyzed by DSC (FIG. 3K) to confirm they were in the glassy state. Different preparation conditions (solvents, concentrations, surfactants, surfactant concentrations, mixing conditions, etc.) resulted in different particle sizes and distributions.

Figure 4:
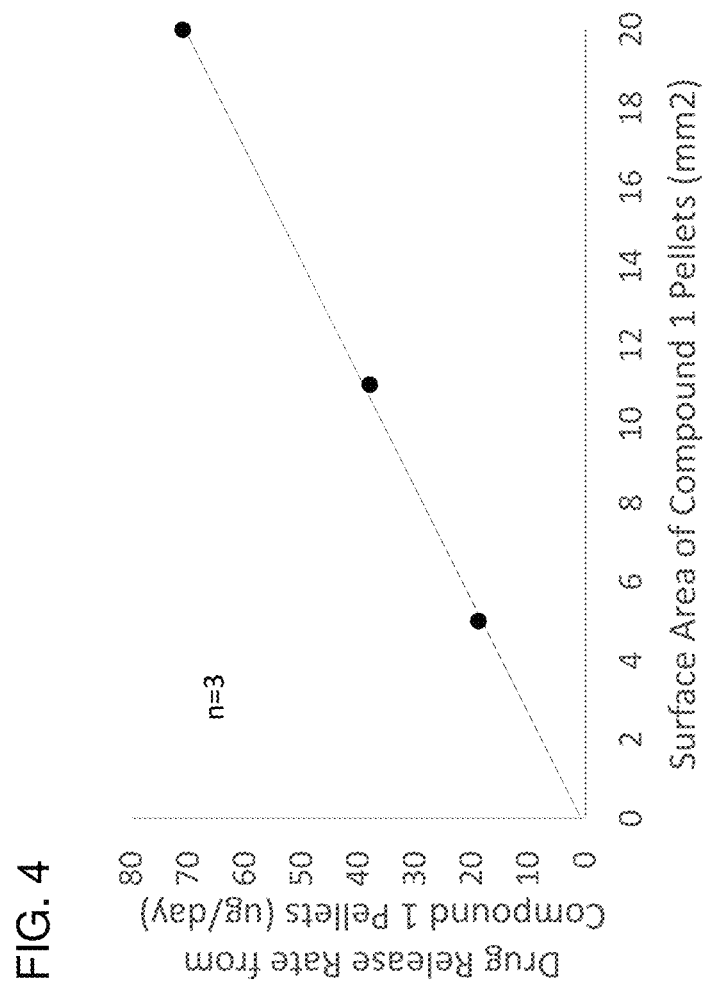
FIG. 4 is a graph showing drug release of pellets of Compound 1 in 100% FBS over time.

Example 4: Drug Release Properties from Heat-Molded Pellets of Compound 1 (Dex-TEG-Dex) can be Adjusted by Changing the Physical Properties of the Pellets Due to Surface Erosion Mechanism of Drug Release Compound 1 was heat-molded into pellets with ~1 mm and ~0.35 mm diameters using the conditions described in Example 1 and 2 above to get pellets with different masses of Compound 1 and different surface areas. Details of the samples are summarized in Table 2, below. Drug release from the different samples was carried out in 100% FBS as described in Example 1 over a 7 day period. The change in drug release expected from different surface areas due to the surface erosion mechanism of drug release is exemplified in FIG. 4 as a plot of surface area vs. the average drug released per day taken from the linear release curves.

TABLE 2

Heat-Molded Pellets Formed From Compound 1. Different Masses and Surface Areas Were Obtained by Changing the Number of Pellets of Given Dimensions

| Sample Number | Pellet Dimensions (diameter × length) | Number of Pellets | Total Mass of Compound 1 | Total Surface Area |
|---|---|---|---|---|
| 1 | ~1 mm × 1 mm | 1 | ~1 mg | ~5 mm$^2$ |
| 2 | ~0.35 mm × ~0.8 mm | 12 | ~1 mg | ~11 mm$^2$ |
| 3 | ~1 mm × 1 mm | 4 | ~4 mg | ~20 mm$^2$ |

Example 5: Mechanical Testing of Extruded Cylinders of Compound 1 (Dex-TEG-Dex) Using a 3 Point Bend Test (ASTM C1684-18)

Figure 5:
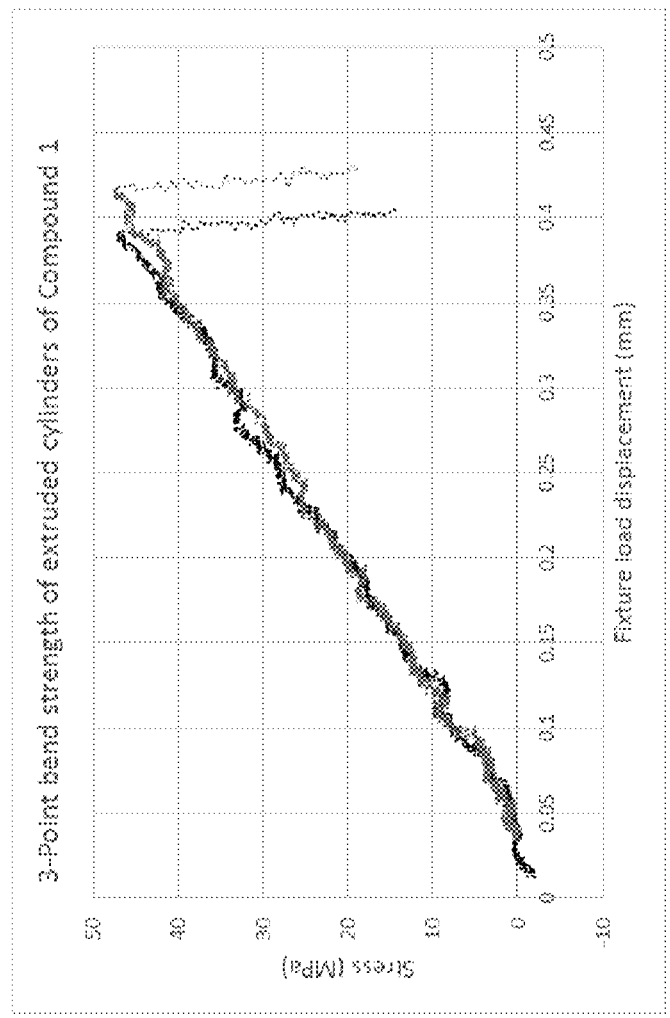
FIG. 5 is a graph showing representative fracture force.

The mechanical properties of extruded cylinders of Compound 1 were quantified with a 3-point bend test using ASTM C1684-18 (Standard test method of Flexural strength of advanced ceramics and ambient temperature-cylindrical rod strength). The ASTM C1684-18 was followed as closely as possible but modifications were necessary due to the small dimensions of the extruded cylinders. Representative fracture force data from the 3-point bend test of Compound 1 cylinders (~0.25 mm×6 mm) are shown in FIG. 5.

Example 6: Ethylene Oxide Gas Sterilization of Heat Molded Pellets of Compound 1 (Dex-TEG-Dex)

Figure 6B:
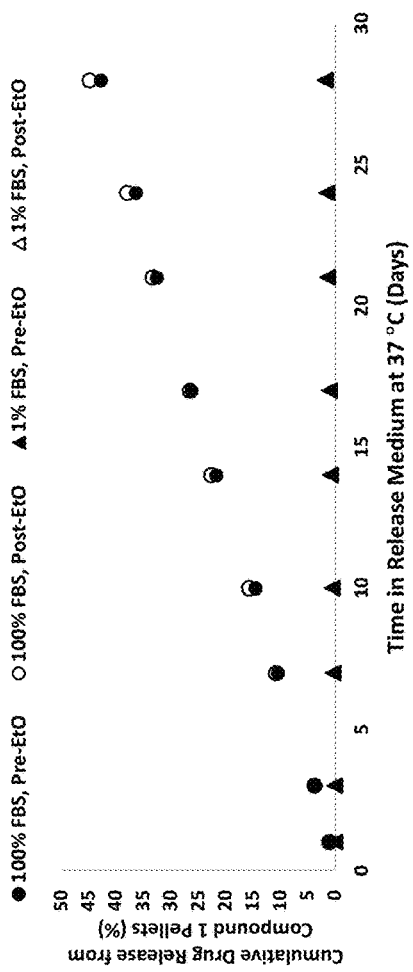
FIGS. 6A and 6B are a series of graphs showing purity of Compound 1 pre- and post-ethylene oxide gas sterilization (FIG. 6A) and drug release (FIG. 6B).
Figure 6A:
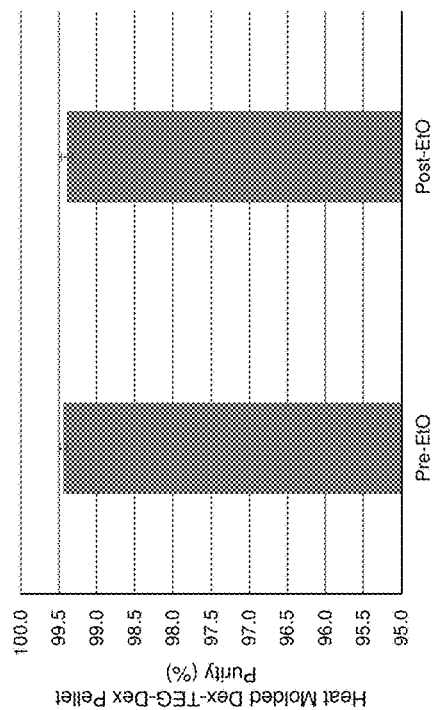

Heat-molded pellets from Compound 1 (~1 mm in diameter) were sterilized by ethylene oxide (ETO) gas at a temperature of 55° C. Pre- and post-ETO sterilized pellets were analyzed by HPLC to demonstrate no changes in pellet (Compound 1) purity (FIG. 6A) and drug release (FIG. 6B) to demonstrate no changes in release properties due to the ETO sterilization process. Drug release was carried out in either 1% FBS in PBS or 100% FBS as described in Example 1.

Figure 7A:
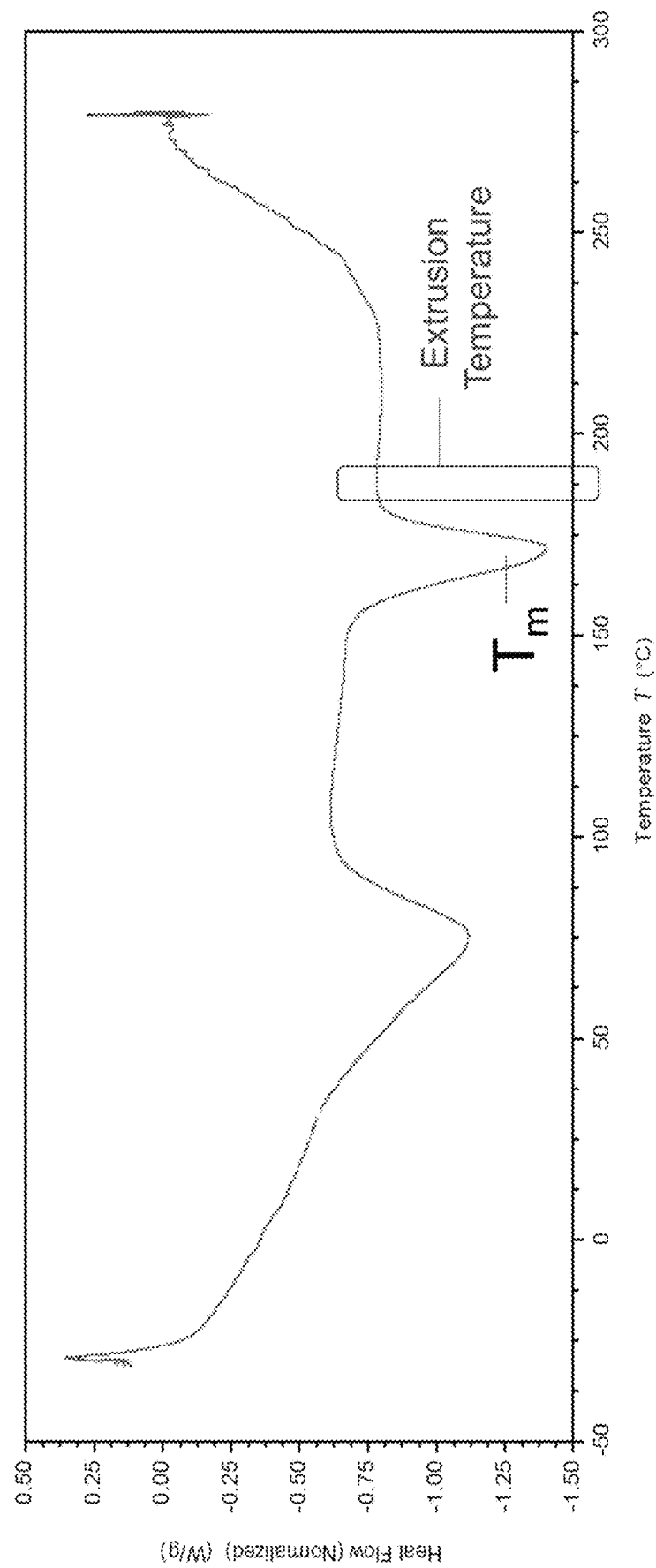
Figure 7B:
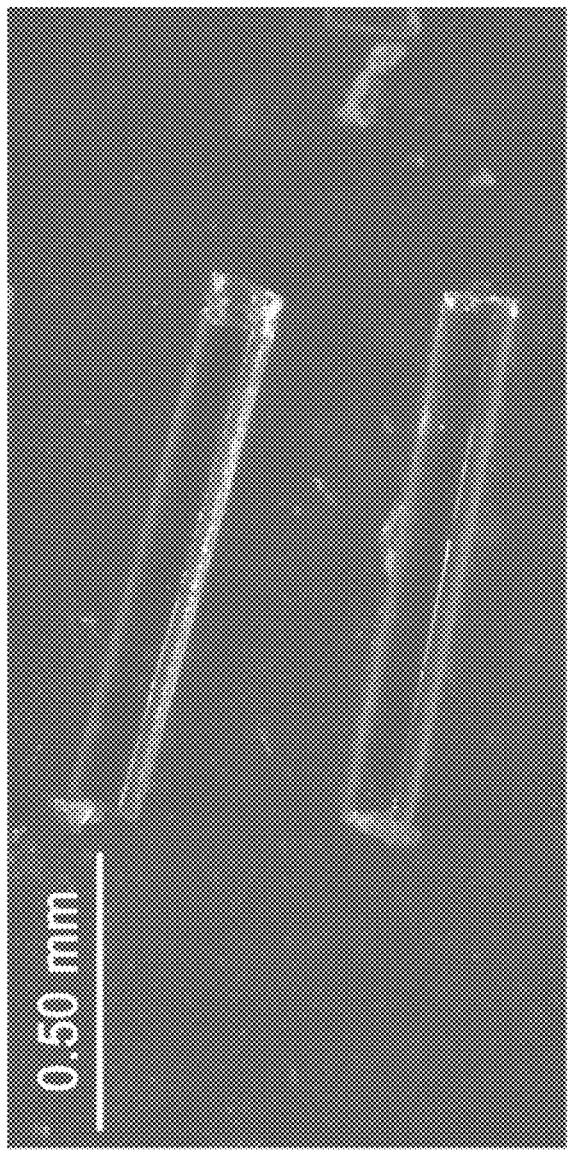
Figure 7C:
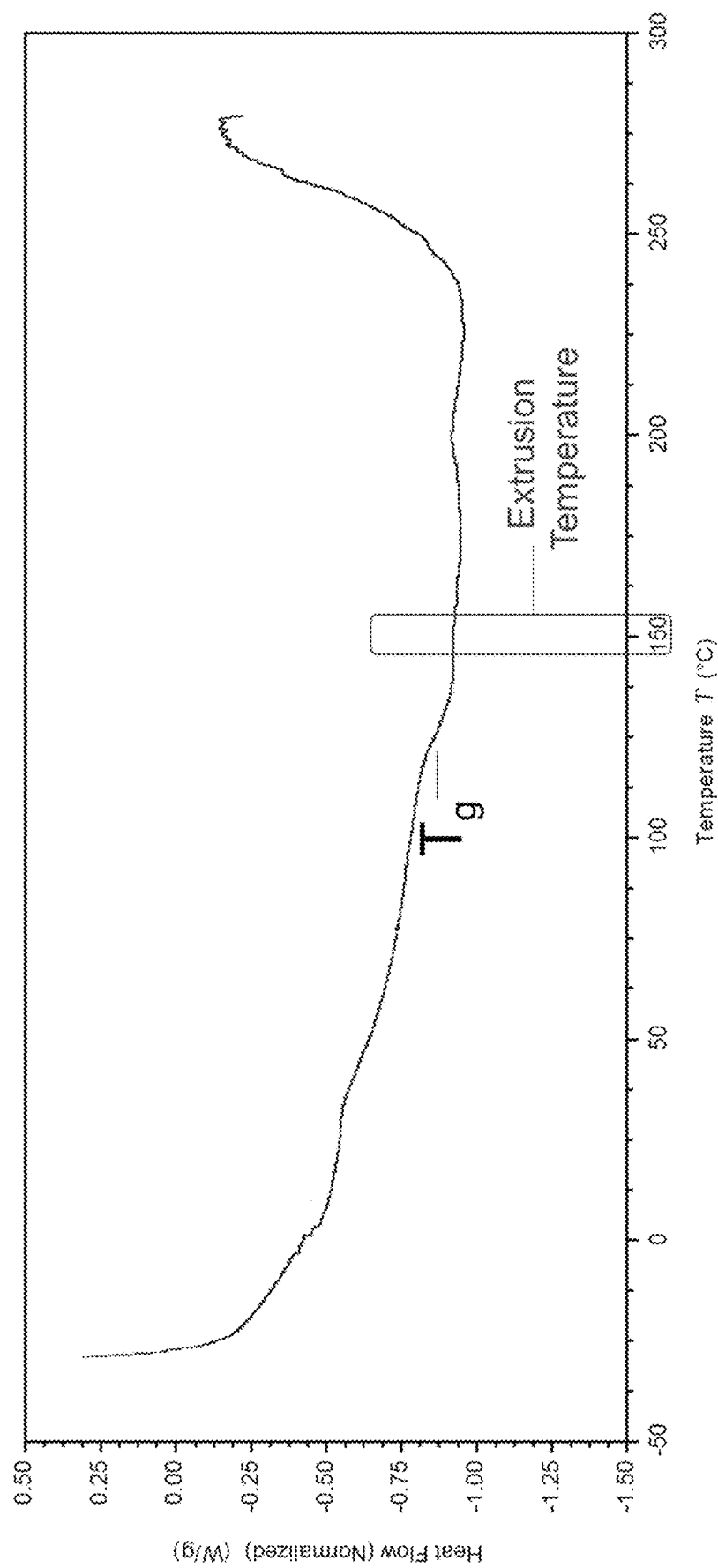
Figure 7D:
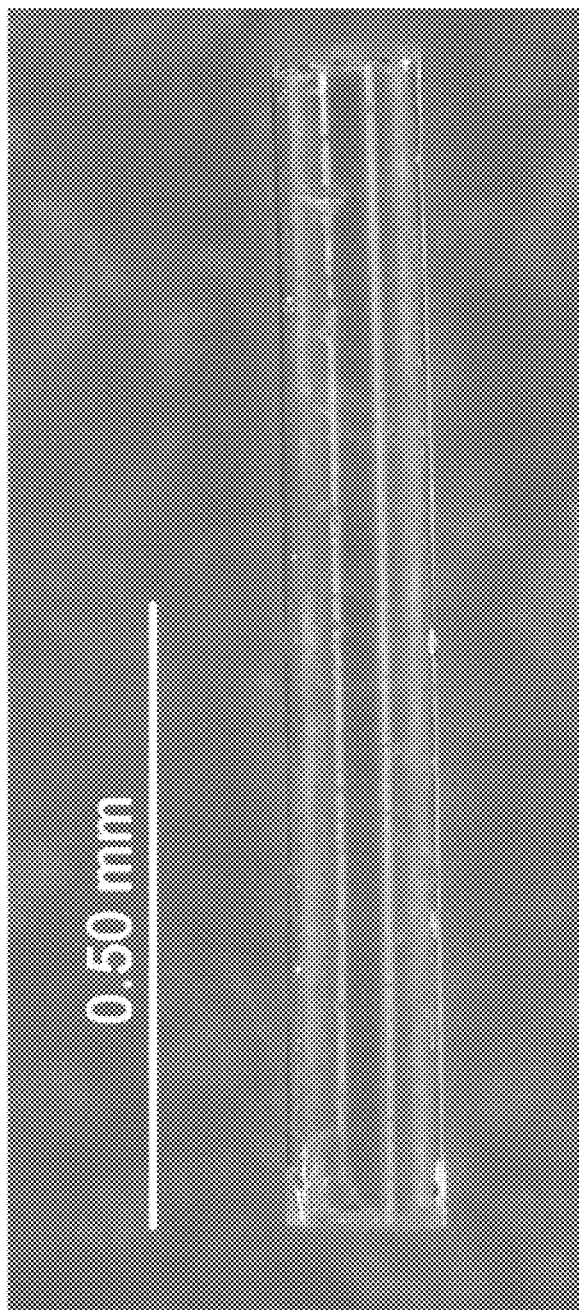

Example 7: Processing Compound 1 (Dex-TEG-Dex) into an Intermediate Glassy State to Manufacture the Final Article Compound 1 (Dex-TEG-Dex) was formed into heat extruded cylinders directly from the crystalline powder by heating above the melting point (185° C.), as shown in FIGS. 7A and 7B, using the methods described above in Example 2. Compound 1 was also formed into heat extruded cylinders by forming an intermediate glassy state form from the melt followed by heat extrusion above the glass transition temperature (150° C.) as shown in FIGS. 7C and 7D. Purity of the extrudate over time is shown in FIG. 7E and demonstrates longer extrusion run times using the intermediate glassy state before Compound 1 drops in purity when compared to extrusion from the melt state.

An intermediate glassy state was also formed from the solution state. Compound 1 was dissolved in acetone and was electrosprayed onto a polymer surface to form glassy state microparticles. The sprayed surface was heated to −150° C. to obtain a coating as shown in FIG. 7F.

Example 8: Synthesis of Compounds 3 to 8

Compounds 3 to 8 were synthesized using standard methods known in the art, similar to the synthesis of Compound 1 in Example 1 above. Details of synthesized Compounds 3 to 8 are shown in Table 3, below. All compounds were synthesized to HPLC purity of 98% and structures were confirmed by $^1$H NMR and ESI MS. Melting points (Tm) and glass transition temperatures (Tg) were determined to establish processing temperatures needed to heat-process the compounds into pellets, fibers, and cylinders for further testing.

TABLE 3

Structures of Compounds 3 to 8

Figure 9D:
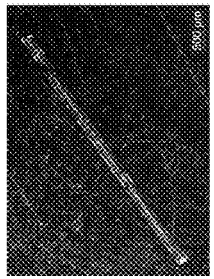
FIGS. 9A-9E are a series of images and a graph showing Compound 6 (FIG. 9A) (dexamethasone-hexane-dexamethasone, Dex-HEX-Dex) processed into heat-molded pellets (FIG. 9B), fibers (FIG. 9C), extruded cylinders (FIG. 9D), and drug release (FIG. 9E).
Figure 9C:
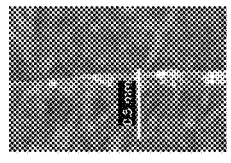
Figure 9B:
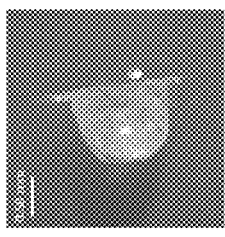
Figure 9E:
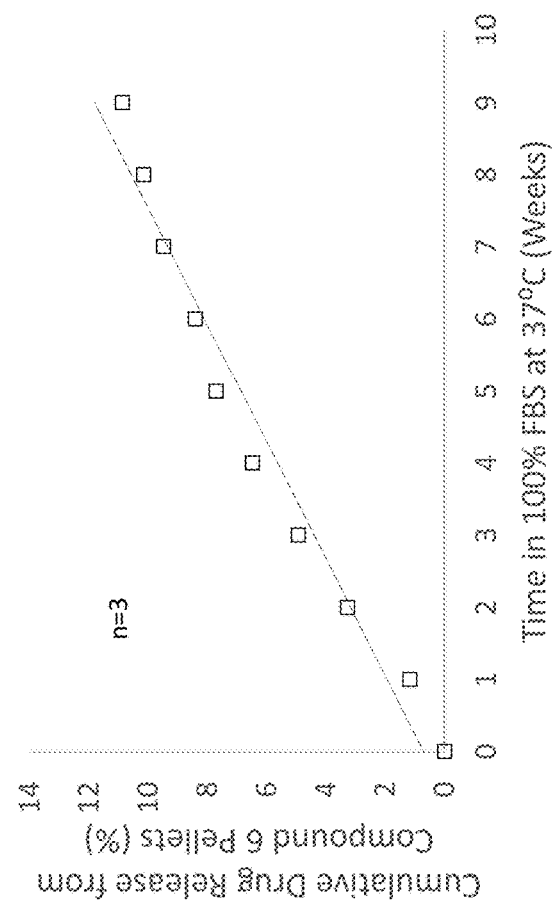
Figure 9A:
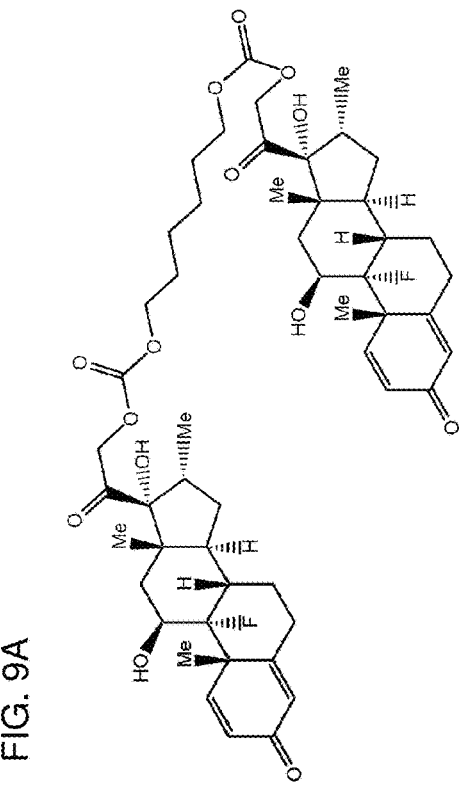
Figure 10B:
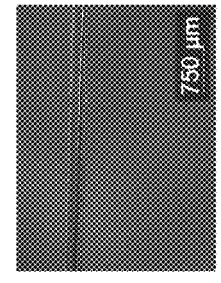
FIGS. 10A-10D are a series of images and a graph showing Compound 7 (FIG. 10A) (dexamethasone-polyethylene glycol (MW=200)-dexamethasone, Dex-PEG200-Dex) processed into heat-molded pellets (FIG. 10B), extruded cylinders (FIG. 10C), and drug release (FIG. 10D).
Figure 10C:
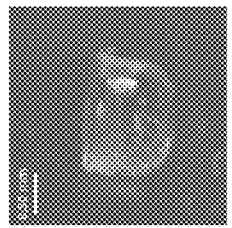
Figure 10D:
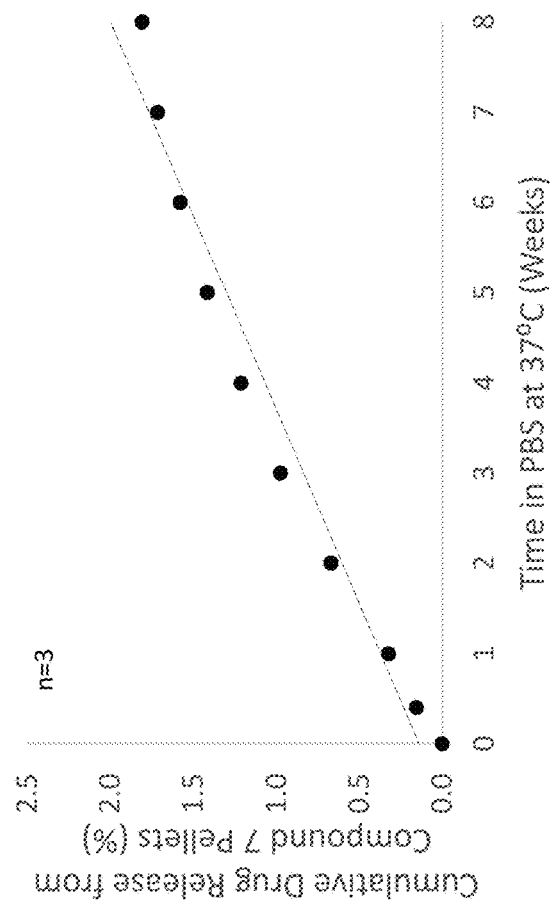
Figure 10A:
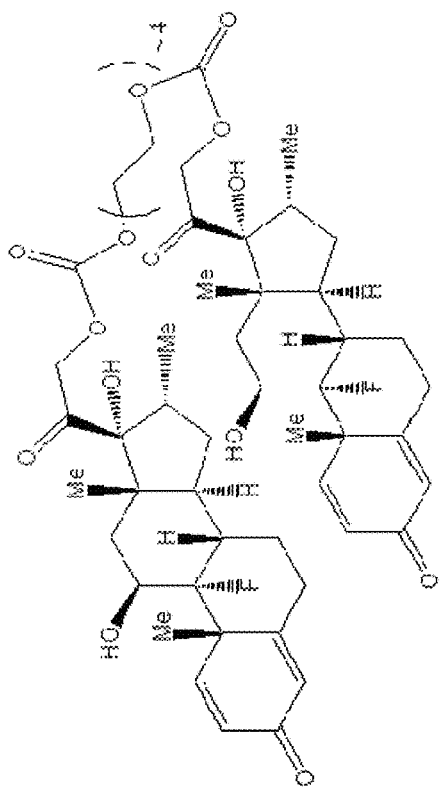
Figure 13B:
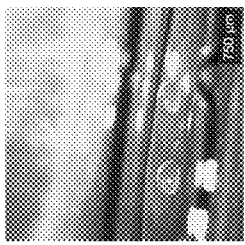
FIGS. 13A-13D are a series of image showing Compound 4 (FIG. 13A) (dexamethasone-heptaethylene glycol-dexamethasone, Dex-EG7-Dex) processed into heat-molded pellets (FIG. 13B) and extruded cylinders (FIG. 13C), the extruded cylinders after two weeks in PBS at 37° C.
Figure 13C:
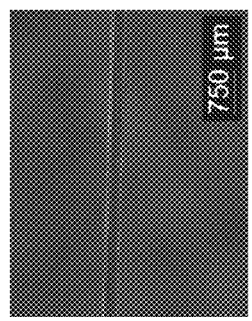
Figure 13D:
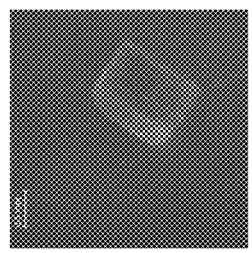
Figure 13A:
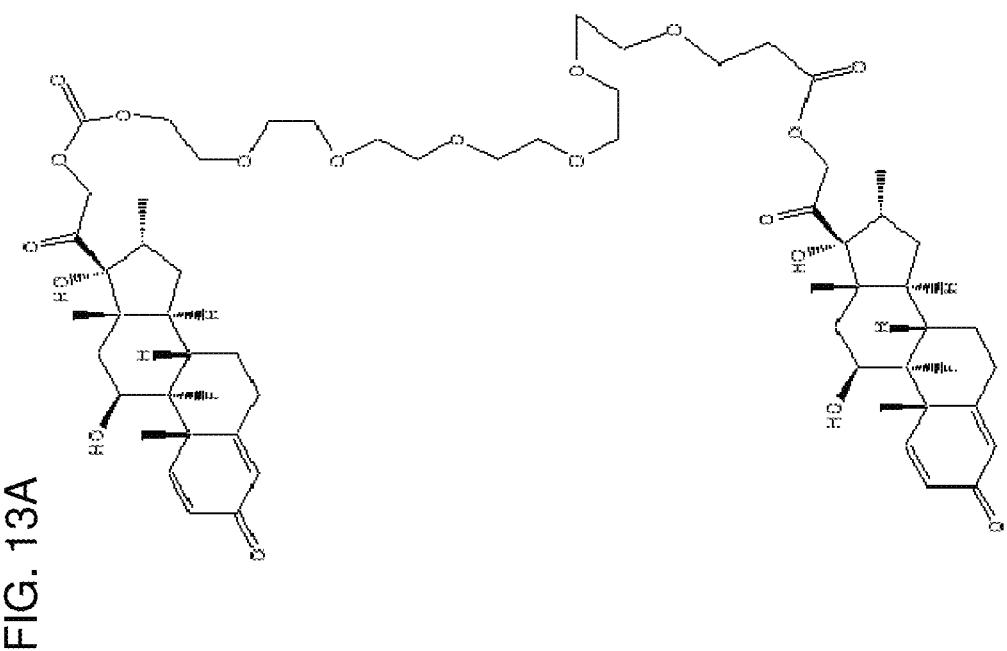
Figure 14D:
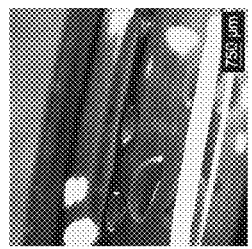
FIGS. 14A-14D are a series of image showing Compound 5 (FIG. 14A) (dexamethasone-nonaethylene glycol-dexamethasone, Dex-EG9-Dex) processed into heat-molded pellets (FIG. 14B) and extruded cylinders (FIG. 14C), and the extruded cylinders after two weeks in PBS at 37° C.
Figure 14C:
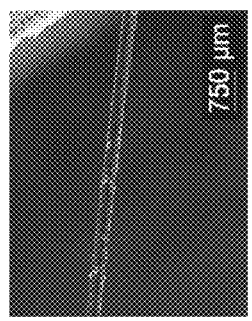
Figure 14B:
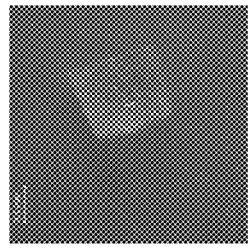
Figure 14A:
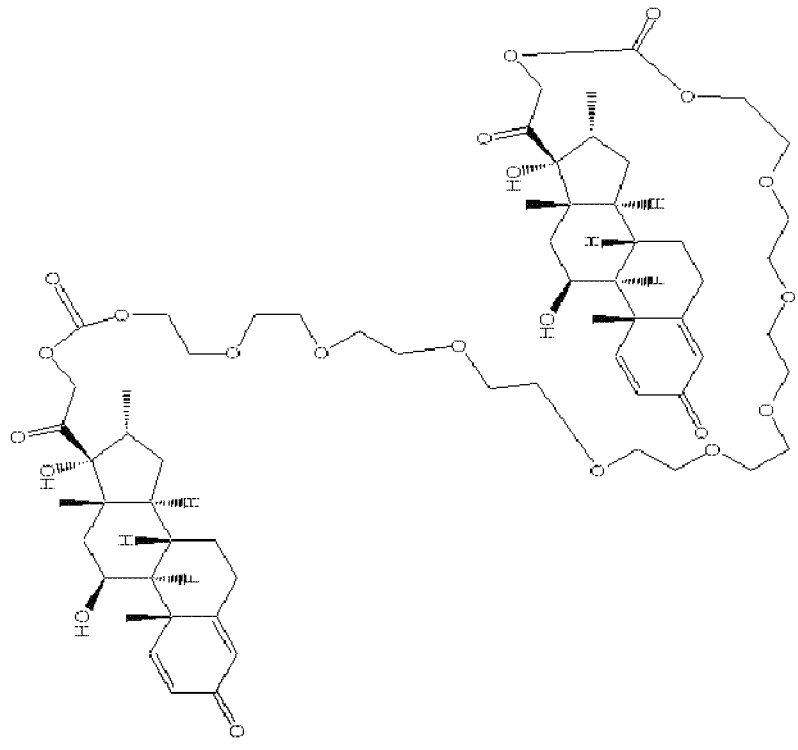
Figure 15A:
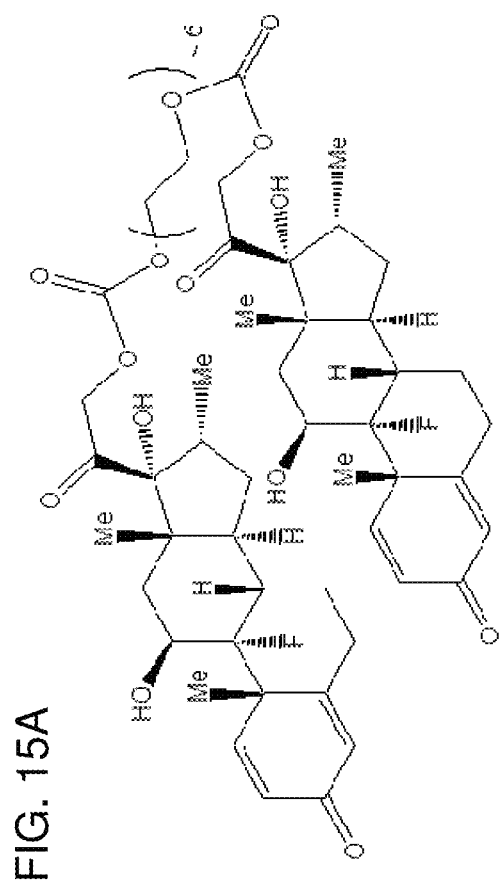
FIGS. 15A-15D are a series of image showing Compound 8 (FIG. 15A) (dexamethasone-polyethylene glycol (MW=300)-dexamethasone, Dex-PEG300-Dex) processed into heat-molded pellets (FIG. 15B) and extruded cylinders (FIG. 15C), and the extruded cylinders after two weeks in PBS at 37° C.

| Compound (Abbreviation) | Linker | Linking Moiety | Structure | Tm & Tg (° C.) |
| --- | --- | --- | --- | --- |
| 3 (Dex-EG5-Dex) | Pentaethylene Glycol | Carbonate | FIG. 8A | n.d.* & 66 |
| 4 (Dex-EG7-Dex) | Heptaethylene Glycol | Carbonate | FIG. 13A | 51 & 47 |
| 5 (Dex-EG9-Dex) | Nonaethylene Glycol | Carbonate | FIG. 14A | 41 & 37 |
| 6 (Dex-HEX-Dex) | Hexane Diol | Carbonate | FIG. 9A | 149 & 146 |
| 7 (Dex-PEG200-Dex) | Polyethlene Glycol (MW = 200) | Carbonate | FIG. 10A | n.d.* & 96 |
| 8 (Dex-PEG300-Dex) | Polyethylene Glycol (MW = 300) | Carbonate | FIG. 15A | 77 & 75 |

*n.d. = not determined

Example 8: Formation of Pellets, Fibers, and/or Cylinders in the Glassy State from Compounds 3, 6, and 7 and Drug Release from Intact Glassy-State Pellets Compounds 3, 6, and 7 were processed into heat molded pellets (~1 mm×~1 mm), fibers from the melt state, and/or heat extruded cylinders from the melt or intermediate glassy state as described in Examples 1, 2, and 7 above using the appropriate temperature for each compound (i.e., above the Tm or Tg as required). Processing Compounds 3, 6, and 7 into the articles converted crystalline compounds into the glassy state and was confirmed for heat molded pellets by DSC. Drug release from heat molded pellets was carried out in PBS and/or 100% FBS, as described in Example 1, for different time periods. Cumulative drug release plotted over time demonstrated drug release from different compounds occurs mostly linearly at different rates from intact pellets in the timeframes tested, similar to drug release from Compound 1. Figures corresponding to images of the pellets, fibers, and cylinders and drug release curves from pellets are indicated in Table 4, below.

TABLE 4

Compounds 3, 6, and 7 Processed in Glassy State and Drug Release

| Compound | Processed Compounds in Glassy State | | | |
|---|---|---|---|---|
| | Heat-Molded Pellets | Fibers | Extruded Cylinders | Drug Release |
| 3 (Dex-EG5-Dex) | FIG. 8B | Not Tested | Not Tested | FIG. 8C |
| 6 (Dex-Hex-Dex) | FIG. 9B | FIG. 9C | FIG. 9D | FIG. 9E |
| 7 (Dex-PEG200-Dex) | FIG. 10B | Not Tested | FIG. 10C | FIG. 10D |

Figure 11B:
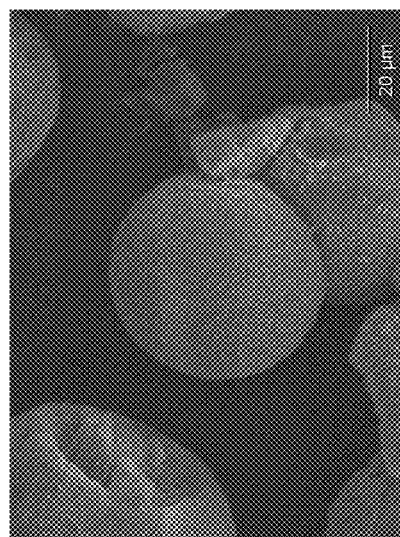
FIGS. 11A and 11B are a series of images showing nano- and microparticles formed from Compound 6.
Figure 11A:
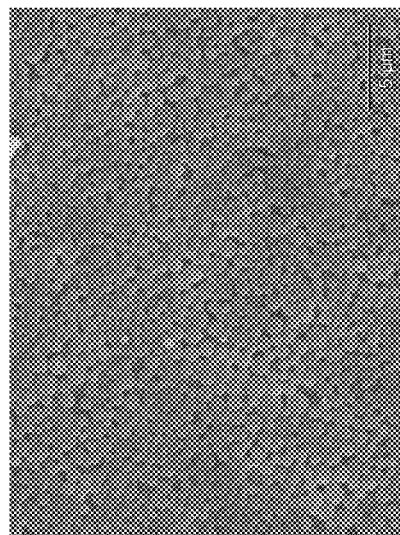

Example 9: Nano- and Micro-Particle Formation in the Glassy State from Compound 6 (Dex-HEX-Dex) Provides Sustained Release of Drug Electrospraying and emulsions were used to make nano- and microparticles from Compound 6 (FIGS. 11A and 11B) using conditions similar to that described for Compound 1 in Example 3 above. Different preparation conditions, for example solvents, concentrations, surfactants, surfactant concentrations, mixing conditions, etc., resulted in different particle sizes and distributions. DSC was used to confirm the particles were in the glassy state.

Example 10: Methods to Adjust Release of Drug from Glassy State Articles

Figure 12:
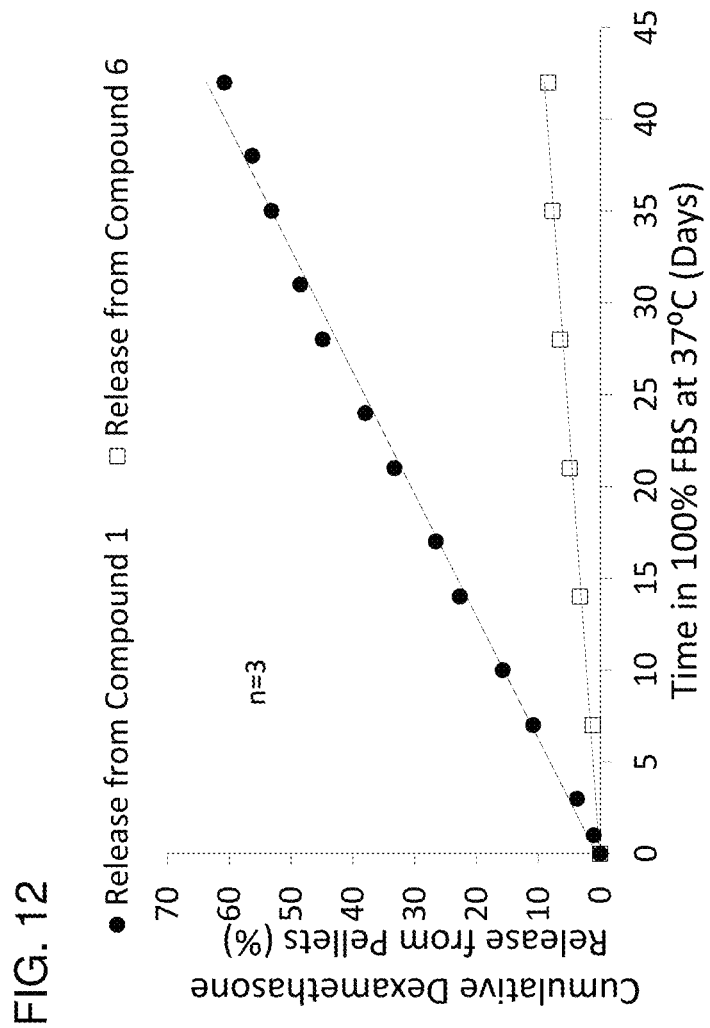
FIG. 12 is a graph showing dexamethasone release from heat-molded pellets of Compound 1 and Compound 6 in 100% FBS.

The release of drug from glassy state articles can be controlled in various ways for example by changing the environment the article is placed or by adjusting the physical properties of the article to take advantage of the surface erosion mechanism of drug release. In scenarios where the environment and physical properties of the article are fixed, other properties such as compound structure via a change in linker can be adjusted to engineer the article to obtain the desired drug release properties for the application of interest. Dexamethasone release from heat molded pellets (~1 mm×1 mm) of Compound 1 (Dex-TEG-Dex) and Compound 6 (Dex-Hex-Dex) in 100% FBS as shown in FIG. 12 exemplifies how linker affects the drug release rates.

Example 11: Compounds 4 (Dex-EG7-Dex), 5 (Dex-EG9-Dex), and 8 (Dex-PEG300-Dex) can be Formed into Heat Molded Pellets and Extruded Cylinders in the Glassy State but Undergo Physical (e.g., Shape) and Drug Release Changes Over Time in Release Medium at 37° C.

Figure 16B:
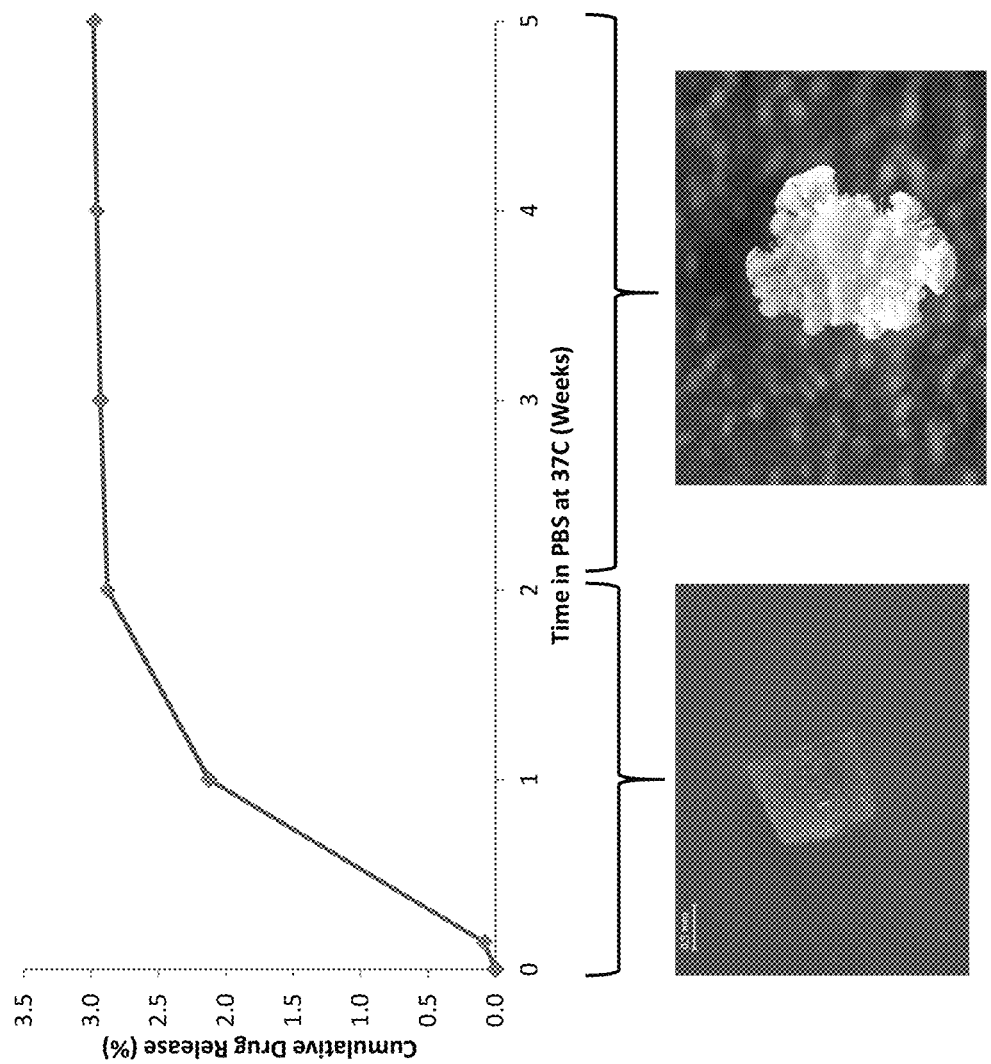

Compounds 4, 5, and 8 were processed into heat molded pellets (~1 mm×~1 mm) and heat extruded cylinders as described in Examples 1, 2, and 7 above using the appropriate temperature for the compound and are shown in the table below. The heat-processed articles from Compounds 4, 5, and 8 were in the glassy state as confirmed by DSC. Drug release from heat molded pellets were carried out in PBS and 100% FBS, as described in Example 1, for Compounds 4 and 5. Physical (shape) and drug release changes occurred for both compounds in PBS and 100% FBS and is exemplified in FIGS. 16A and 16B for pellets of Compounds 4 and 5 respectively in PBS at 37° C. Similar changes in physical form (shape) were observed for extruded cylinders for Compounds 4, 5, and 8 where they formed into droplets on the bottom of the vial in less than 2 weeks in PBS at 37° C. as shown in Table 5, below.

TABLE 5

Compounds 4, 5, and 8 Processed in Glassy State

Figure 15D:
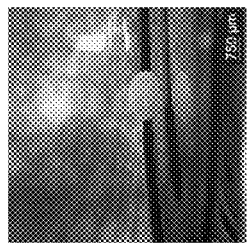
Figure 15C:
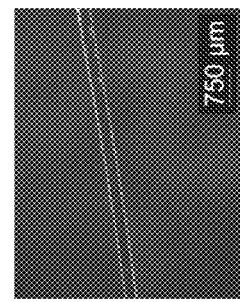
Figure 15B:
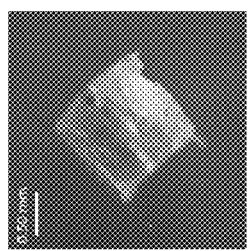

| Compound | Processed Compounds in Glassy State | | |
|---|---|---|---|
| | Heat Molded Pellets | Extruded Cylinders | Extruded Cylinder after 2 weeks in PBS at 37° C. |
| 4 (Dex-EG7-Dex) | FIG. 13B | FIG. 13C | FIG. 13D |
| 5 (Dex-EG9-Dex) | FIG. 14B | FIG. 14C | FIG. 14D |
| 8 (Dex-PEG300-Dex) | FIG. 15B | FIG. 15C | FIG. 15D |

Figure 17:
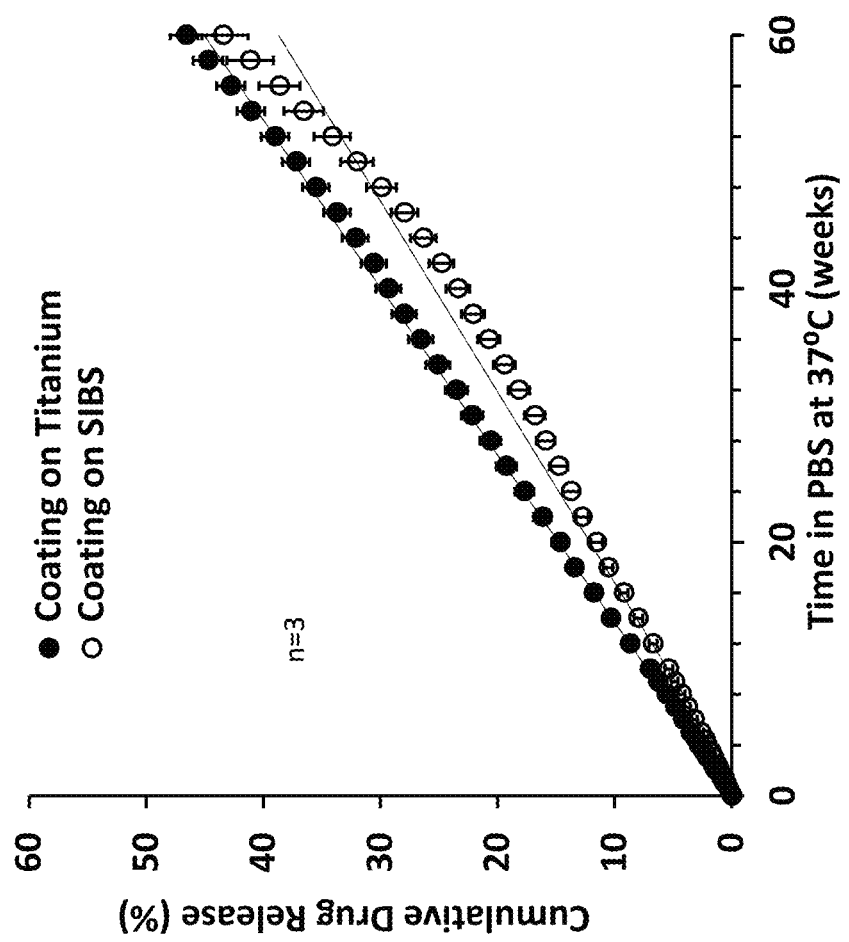
FIG. 17 is a graph showing cumulative drug release from a coating of Compound 1 (Dex-TEG-Dex) from titanium and poly(styrene-block-isobutylene-block-styrene) (SIBS) over time.

Example 12: Drug Release from Compound 1 (Dex-TEG-Dex) Coated on Different Surfaces Compound 1 was coated onto titanium and SIBS as described in Example 3 above. Drug release from the coated material was carried out in PBS as described in Example 1 above. Cumulative drug release was calculated and plotted as a percentage of the total drug in each coated surface released over time (FIG. 17).

Example 13: Effect of Linker on Article Stability and Dexamethasone Release Profiles Each of compounds 1-8 differ in modest changes to the linker covalently tethering two dexamethasone radicals into a dimer. All of the compounds were observed to be capable of being processed into articles (e.g., glassy amorphous solids). However, articles formed from different compounds were observed to exhibit dramatically different stability (under physiologically relevant conditions) and dramatically different dexamethasone release profiles.

For example, articles formed from Compounds 4, 5, and 8 (i.e., the compounds with the longer PEG linkers) appear to undergo a change in physical form (geometric shape) in an aqueous environment at 37° C., while articles formed from Compounds 1, 3, 6, and 7 do not. As evidenced in FIGS. 13D, 14D, and 15D, Compounds 4, 5, and 8 form into spherical droplets after two weeks in PBS. On the other hand, FIG. 1F shows pellets formed from Compound 1 maintaining their shape over extended periods of time, and similar stability was observed for compounds 3, 6, and 7 in PBS.

Articles formed from different compounds were also observed to exhibit dramatically different dexamethasone release profiles. For example, the dexamethasone release profiles from articles formed from compounds 1, 3, 6, and 7 were observed to be generally linear over the course of 12 weeks or more (see, e.g., FIGS. 1E, 8C, 9E, and 10D). In contrast, the dexamethasone release profiles from articles formed from compounds 4 and 5 were observed to be non-linear (see FIGS. 16A and 16B). Surprisingly, in articles formed from compound 5 the dexamethasone release stops at only ca. 3% cumulative release after just 2 weeks in PBS.

Finally, the dexamethasone release profiles from heat molded pellets (~1 mm×1 mm) of Compound 1 (Dex-TEG-Dex) and Compound 6 (Dex-Hex-Dex) in 100% FBS as shown in FIG. 12 exemplifies how linker affects the drug release rates. The difference in these release profiles show that articles formed from Compound 1 might be preferred for use where dexamethasone release is only needed for 1 or 2 months, while articles formed from Compound 6 might be preferred for use where dexamethasone release is needed for 6 months or more.

Example 14: Dexamethasone Prodrug Dimers

Compounds 9-11, described below, can be prepared by using methods analogous to those described herein. The compounds can be processed as described herein to produce articles capable of producing an extended release profile following implantation into a subject, and can be used in the methods, compositions, and articles of the disclosure.

| Compound | Dimer | Abbreviation |
|---|---|---|
| 9 | Dexamethasone-Ethylene Glycol-Dexamethasone | Dex-EG1-Dex |
| 10 | Dexamethasone-Diethylene Glycol-Dexamethasone | Dex-DEG-Dex |
| 11 | Dexamethasone-Hexaethylene Glycol-Dexamethasone | Dex-EG6-Dex |

Some embodiments of the disclosure provided herein can be defined according to the following numbered items:

1. An article formed from the compound of any one of items 2-5 and 95, wherein the article releases less than 10% of dexamethasone, as a percentage of the total dexamethasone present in the article in prodrug form, at 37° C. in 100% bovine serum over 5 days.

2. A compound described by the formula (I):

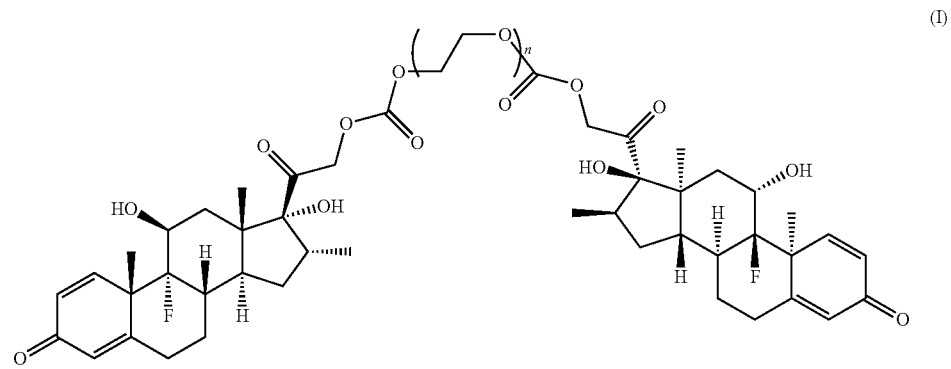

(I)

wherein n is an integer from 1 to 6.

3. The compound of item 2, wherein n is 3.

4. The compound of item 2, wherein n is 4.

5. The compound of item 2, wherein n is 5.

6. A pharmaceutical composition comprising the compound of any one of items 2-5, and a pharmaceutically acceptable excipient.

7. An article comprising Compound 6 or a compound of formula (I):

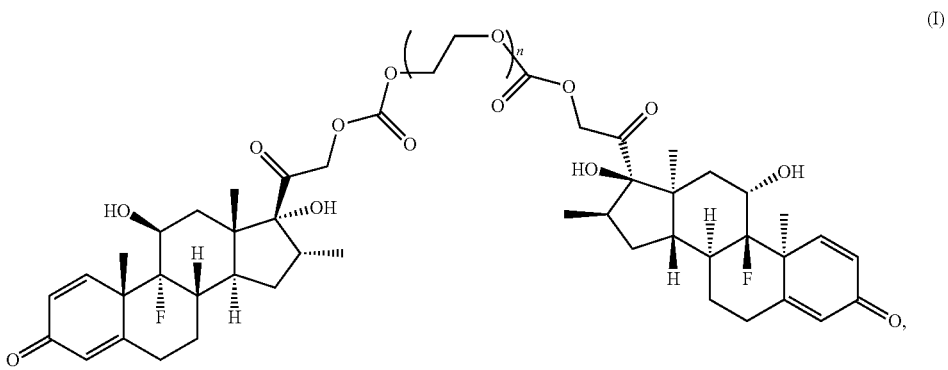

wherein the article provides controlled release of dexamethasone at 37° C. in 100% bovine serum or at 37° C. in PBS; wherein n is an integer from 1 to 6.

8. The article of item 7, wherein dexamethasone is released from the article through surface erosion.

9. The article of item 7 or 8, wherein the article releases less than 10% of dexamethasone, as a percentage of the total dexamethasone present in the article in prodrug form, at 37° C. in 100% bovine serum over 5 days; or the surface erosion releases less than 2% of dexamethasone, as a percentage of the total dexamethasone present in the article in prodrug form, at 37° C. in PBS over 5 days; or the surface erosion releases greater than 20% of dexamethasone, as a percentage of the total dexamethasone present in the article in prodrug form, at 37° C. in 100% bovine serum over not fewer than 6 days; or the surface erosion releases greater than 5.0% of dexamethasone as a percentage of the total dexamethasone present in the article in prodrug form, at 37° C. in PBS over not fewer than 6 days; or dexamethasone is released from the article at a rate such that $t_{10}$ is greater than or equal to $\frac{1}{10}$ of $t_{50}$.

10. The article of any one of items 7-9, wherein the article further comprises from 0.1% to 10% (w/w) of one or more additives, wherein the one or more additives are selected from plasticizers, antioxidants, binders, lubricants, radio-opaque agents, and mixtures thereof.

11. The article of any one of items 7-10, wherein the article is a fiber, fiber mesh, woven fabric, non-woven fabric, pellet, cylinder, hollow tube, microparticle, nanoparticle, or shaped article.

12. The article of any one of items 7-11, wherein the article is free of controlled release excipient, free of a crystallization inhibiting excipient, free of a mechanical integrity enhancing excipient, and/or free of a binding excipient.

13. The article of any one of items 7-12, wherein the article is in a glassy state.

14. An article comprising Compound 6, or a compound of formula (I):

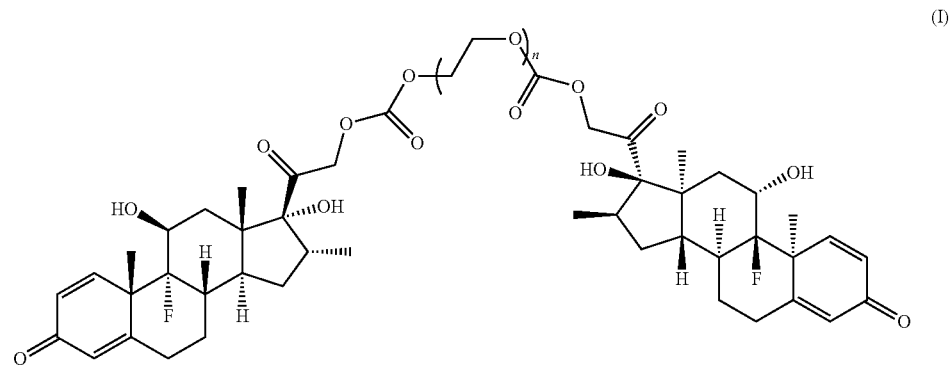

wherein the article is formed by a process comprising the steps of:
(a) heating the compound to form a melt; and
(b) heat molding the melt to form the article,
wherein n is an integer from 1 to 6.

15. An article comprising Compound 6 or a compound of formula (I):

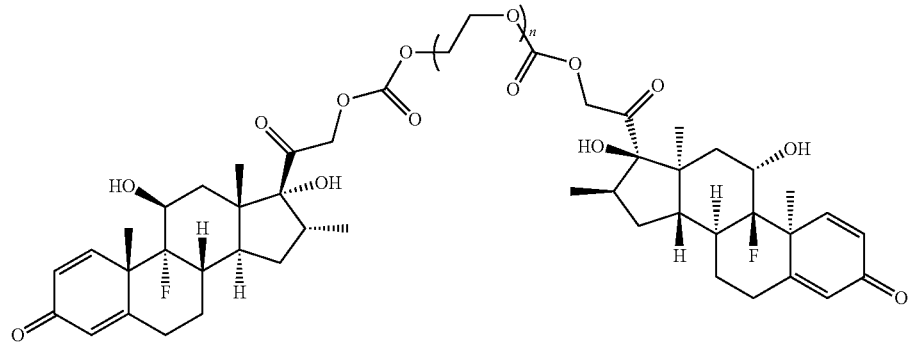
(I)

wherein the article is formed by a process comprising the steps of:
(a) heating the compound to form a melt; and
(b) injection molding the melt to form the article,
wherein n is an integer from 1 to 6.

16. An article comprising Compound 6 or a compound of formula (I):

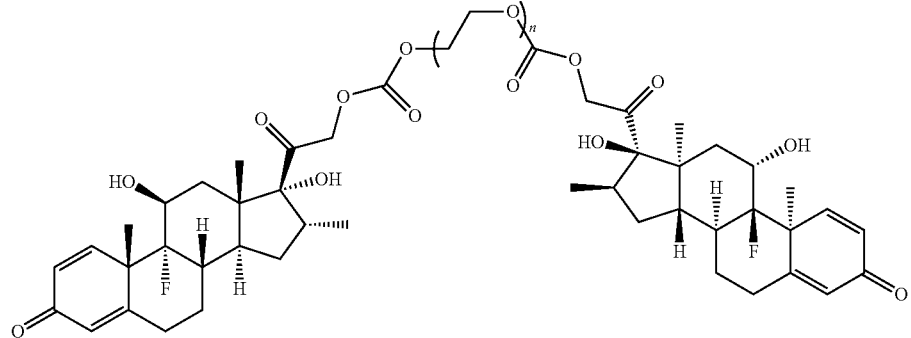
(I)

wherein the article is formed by a process comprising the steps of:
(a) heating the compound to form a melt; and
(b) blow molding the melt to form the article,
wherein n is an integer from 1 to 6.

17. An article comprising Compound 6 or a compound of formula (I):

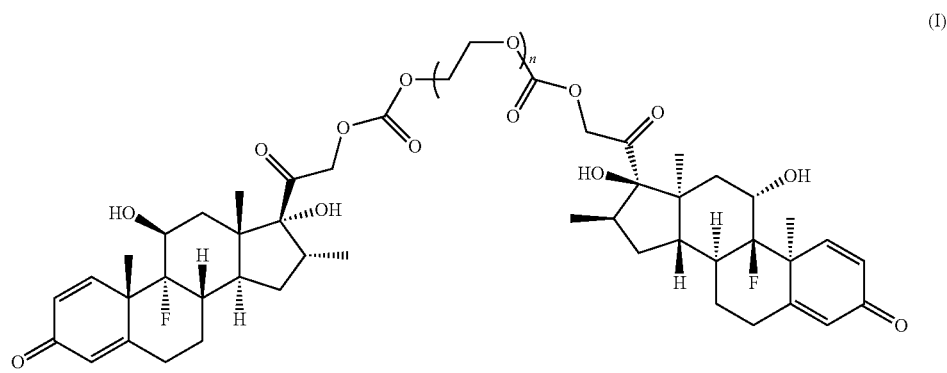

wherein the article is formed by a process comprising the steps of:
(a) dissolving the compound to form a solution; and
(b) evaporating the solvent to form the article,
wherein n is an integer from 1 to 6.

18. The article of item 17, wherein step (b) comprises solvent casting to form a film or a fiber.

19. An article comprising Compound 6 or a compound of formula (I):

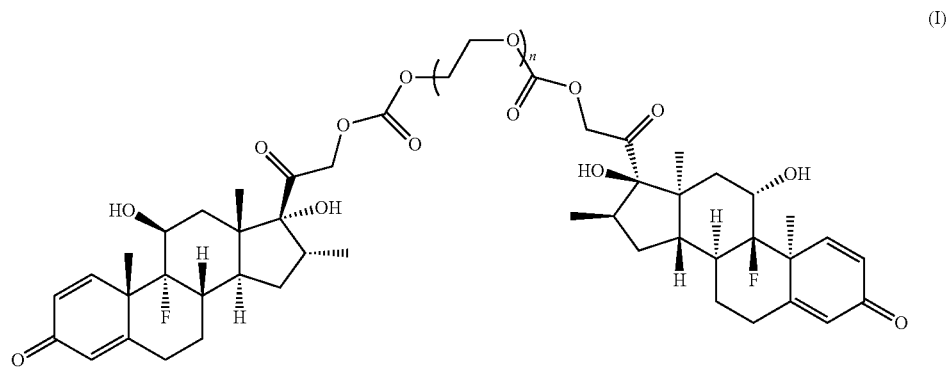

wherein the article is formed by a process comprising the steps of:
(a) dissolving the compound to form a solution; and
(b) electrospinning or electrospraying the solution to form the article,
wherein n is an integer from 1 to 6.

20. An article comprising Compound 6 or a compound of formula (I):

(I)

wherein the article is formed by a process comprising the steps of:
(a) heating the compound to form a melt; and
(b) electrospinning or electrospraying the melt to form the article,
wherein n is an integer from 1 to 6.

21. An article comprising Compound 6 or a compound of formula (I):

(I)

wherein the article is formed by a process comprising the steps of:
(a) heating the compound to form a melt;
(b) extruding the melt to form the article,
wherein n is an integer from 1 to 6.

22. The article of any one of items 7-21, wherein n is 3.
23. The article of any one of items 7-21, wherein n is 4.
24. The article of any one of items 7-21, wherein n is 5.
25. An article formed from the compound of any one of items 2-5 and 95.
26. The article of any one of items 7-25, wherein at least 70% (w/w) of the article is Compound 6 or the compound of formula (I).
27. The article of any one of items 7-26, wherein at least 90% (w/w) of the article is Compound 6 or the compound of formula (I).
28. The article of any one of items 7-27, wherein the compound or dexamethasone is released from the article through surface erosion.
29. The article of item 28, wherein the surface erosion releases less than 10% of dexamethasone, as a percentage of the total drug, dexamethasone, present in the article in prodrug form, at 37° C. in 100% bovine serum over 5 days; or the surface erosion releases less than 2% of dexamethasone, as a percentage of the total drug, dexamethasone, present in the article in prodrug form, at 37° C. in PBS over 5 days; or the surface erosion releases greater than 20% of dexamethasone, as a percentage of the total dexamethasone present in the article in prodrug form, at 37° C. in 100% bovine serum over not fewer than 6 days; or the surface erosion releases greater than 5.0% of dexamethasone as a percentage of the total dexamethasone present in the article in prodrug form, at 37° C. in PBS over not fewer than 6 days; or dexamethasone is released from the article at a rate such that $t_{10}$ is greater than or equal to $\frac{1}{10}$ of $t_{50}$.

30. The article of any one of items 7-29, wherein the article further comprises from 0.1% to 10% (w/w) of one or more additives, wherein the one or more additives are selected from plasticizers, antioxidants, binders, lubricants, radio-opaque agents, and mixtures thereof.

31. The article of any one of items 7-30, wherein the article is a fiber, fiber mesh, woven fabric, non-woven fabric, pellet, cylinder, hollow tube, microparticle, nanoparticle, or shaped article.

32. The article of any one of items 7-31, wherein the article is free of controlled release excipient, free of a crystallization inhibiting excipient, free of a mechanical integrity enhancing excipient, and/or free of a binding excipient; or the article optionally has a glassy state.

33. A fiber formed from the compound of any one of items 2-5 and 95.

34. A fiber formed from Compound 6 or a compound of formula (I):

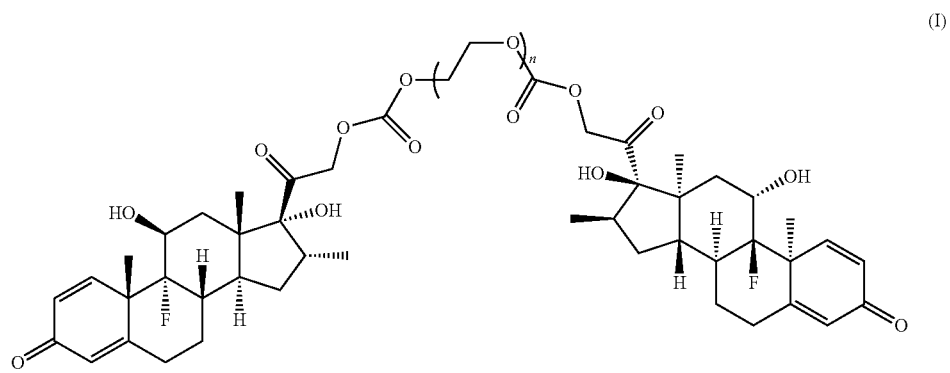

wherein the fiber is prepared by a process comprising the steps of:

(a) dissolving the compound in a solvent to form a solution; and (b) electrospinning, dry spinning, wet spinning, or gel spinning the solution to form the fiber, wherein n is an integer from 1 to 6.

35. A fiber formed from Compound 6 or a compound of formula (I):

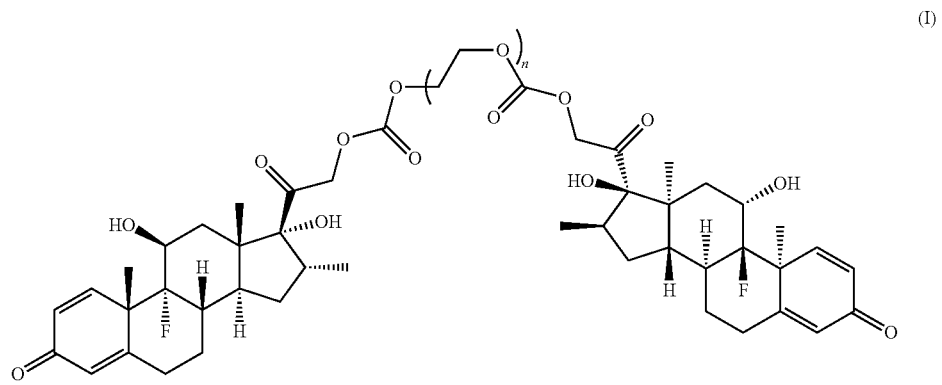

wherein the fiber is prepared by a process comprising the steps of:
(a) heating the compound to form a melt; and
(b) extruding the melt to form the fiber (i.e., melt spinning),
wherein n is an integer from 1 to 6.

36. A fiber formed from Compound 6 or a compound of formula (I):

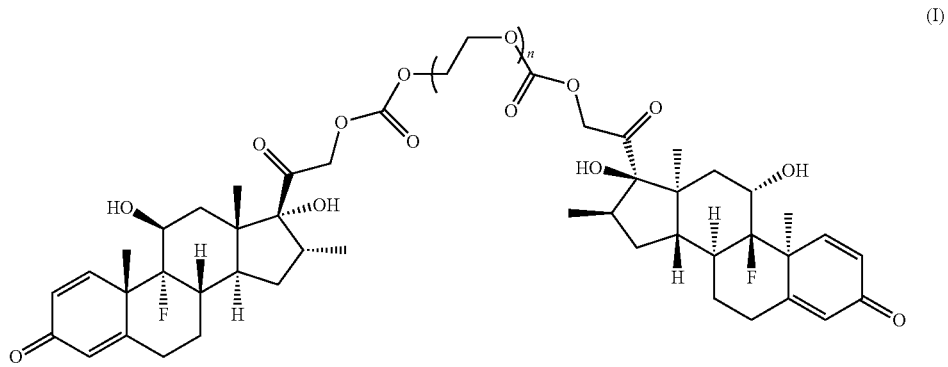

(I)

wherein the fiber is prepared by a process comprising the steps of:
(a) heating the compound to form a melt; and
(b) electrospinning the melt to form the fiber,
wherein n is an integer from 1 to 6.

37. The fiber of any one of items 33-36, wherein n is 3.
38. The fiber of any one of items 33-36, wherein n is 4.
39. The fiber of any one of items 33-36, wherein n is 5.
40. The fiber of any one of items 33-39, wherein at least 70% (w/w) of the fiber is Compound 6 or the compound of formula (I).
41. The fiber of any one of items 33-40, wherein at least 90% (w/w) of the fiber is Compound 6 or the compound of formula (I).
42. The fiber of any one of items 33-41, wherein the compound or dexamethasone is released from the fiber through surface erosion.
43. The fiber of item 42, wherein the surface erosion releases less than 10% of dexamethasone, as a percentage of the total drug, dexamethasone, present in the fiber in prodrug form, at 37° C. in 100% bovine serum over 5 days; or the surface erosion releases less than 2% of dexamethasone, as a percentage of the total drug, dexamethasone, present in the fiber in prodrug form, at 37° C. in PBS over 5 days; or the surface erosion releases greater than 20% of dexamethasone, as a percentage of the total dexamethasone present in the fiber in prodrug form, at 37° C. in 100% bovine serum over not fewer than 6 days; or the surface erosion releases greater than 5.0% of dexamethasone as a percentage of the total dexamethasone present in the fiber in prodrug form, at 37° C. in PBS over not fewer than 6 days; or dexamethasone is released from the fiber at a rate such that or $t_{10}$ is greater than or equal to $\frac{1}{10}$ of $t_{50}$.
44. The fiber of any one of items 33-43, wherein the fiber further comprises from 0.1% to 10% (w/w) of one or more additives, wherein the one or more additives are selected from plasticizers, antioxidants, binders, lubricants, radio-opaque agents, and mixtures thereof.
45. The fiber of any one of items 33-44, wherein the fiber is free of controlled release excipient, free of a crystallization inhibiting excipient, free of a mechanical integrity enhancing excipient, and/or free of a binding excipient; or the fiber optionally has a glassy state.
46. A fiber mesh or woven fabric formed from the fiber of any one of items 33-45.
47. A non-woven fabric formed from the fiber of any one of items 33-46.
48. A glassy state composition formed from the compound of any one of items 2-5 and 95.
49. A glassy state composition formed from Compound 6 or a compound of formula (I):

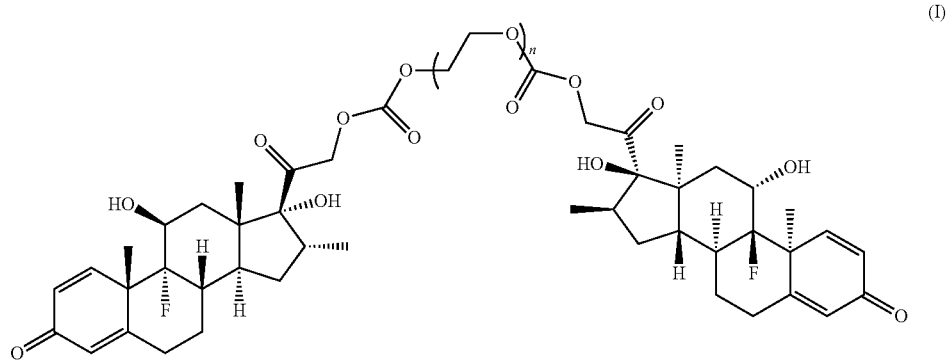

(I)

wherein the composition is prepared by a process comprising the steps of:
(a) heating the compound to form a melt; and
(b) cooling the melt to form the composition,
wherein n is an integer from 1 to 6.

50. The glassy state composition of item 48 or 49, wherein n is 3.

51. The glassy state composition of item 48 or 49, wherein n is 4.

52. The glassy state composition of item 48 or 49, wherein n is 5.

53. The glassy state composition of any one of items 48-52, wherein at least 70% (w/w) of the glassy state composition is Compound 6 or the compound of formula (I).

54. The glassy state composition of any one of items 48-53, wherein at least 90% (w/w) of the glassy state composition is Compound 6 or the compound of formula (I).

55. The glassy state composition of any one of items 48-54, wherein the compound or dexamethasone is released from the glassy state composition through surface erosion.

56. The glassy state composition of item 55, wherein the surface erosion releases less than 10% of dexamethasone, as a percentage of the total drug, dexamethasone, present in the glassy state composition in prodrug form, at 37° C. in 100% bovine serum over 5 days; or the surface erosion releases less than 2% of dexamethasone, as a percentage of the total drug, dexamethasone, present in the glassy state composition in prodrug form, at 37° C. in PBS over 5 days; or the surface erosion releases greater than 20% of dexamethasone, as a percentage of the total dexamethasone present in the glassy state composition in prodrug form, at 37° C. in 100% bovine serum over not fewer than 6 days; or the surface erosion releases greater than 5.0% of dexamethasone as a percentage of the total dexamethasone present in the glassy state composition in prodrug form, at 37° C. in PBS over not fewer than 6 days; or dexamethasone is released from the glassy state composition at a rate such that or $t_{10}$ is greater than or equal to $\frac{1}{10}$ of $t_{50}$.

57. The glassy state composition of any one of items 48-56, wherein the glassy state composition further comprises from 0.1% to 10% (w/w) of one or more additives, wherein the one or more additives are selected from plasticizers, antioxidants, binders, lubricants, radio-opaque agents, and mixtures thereof.

58. The glassy state composition of any one of items 48-57, wherein the glassy state composition is formed by machining, molding, electrospinning, electrospraying, blow molding, fiber spinning, or extruding.

59. The glassy state composition of any one of items 48-58, wherein the glassy state composition is a fiber, fiber mesh, woven fabric, non-woven fabric, pellet, cylinder, hollow tube, microparticle, nanoparticle, or shaped article in the shape of a cylinder, a cube, a sheet, a star, a toroid, a pyramid, a sphere, an irregular polygon, or a regular polygon.

60. The glassy state composition of item 59, wherein the glassy state composition is a shaped article in the form of:
(i) fibers having a mean diameter of from about 0.01 to 1 mm;
(ii) pellets having a mean diameter of from about 0.2 to 5 mm;
(iii) cylinders of from about 0.01 to 1 mm in diameter and 0.5 to 20 mm in length;
(iv) microparticles having a mean diameter of from about 1 to 1000 μm; or
(v) nanoparticles having a mean diameter of from about 0.01 to 1 μm.

61. The glassy state composition of any one of items 48-60, wherein the glassy state composition is free of controlled release excipient, free of a crystallization inhibiting excipient, free of a mechanical integrity enhancing excipient, and/or free of a binding excipient.

62. A substrate comprising a coating formed from the compound of any one of items 2-5 and 95.

63. A substrate comprising a coating formed from Compound 6 or a compound of formula (I):

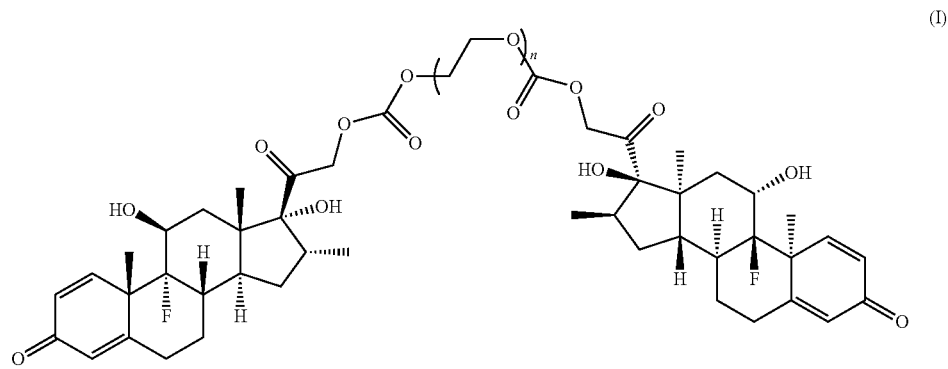

wherein n is an integer from 1 to 6.

64. The substrate of item 62 or 63, wherein n is 3.

65. The substrate of item 62 or 63, wherein n is 4.

66. The substrate of item 62 and 63, wherein n is 5.

67. The substrate of any one of items 62-66, wherein at least 70% (w/w) of the coating is Compound 6 or the compound of formula (I).

68. The substrate of item 62-67, wherein at least 90% (w/w) of the coating is Compound 6 or the compound of formula (I).

69. The substrate of any one of items 62-68, wherein the compound or dexamethasone is released from the coating through surface erosion.

70. The substrate of item 69, wherein the surface erosion releases less than 10% of dexamethasone, as a percentage of the total drug, dexamethasone, present in the coating in prodrug form, at 37° C. in 100% bovine serum over 5 days; or the surface erosion releases less than 2% of dexamethasone, as a percentage of the total drug, dexamethasone, present in the coating in prodrug form, at 37° C. in PBS over 5 days; or the surface erosion releases greater than 20% of dexamethasone, as a percentage of the total dexamethasone present in the coating in prodrug form, at 37° C. in 100% bovine serum over not fewer than 6 days; or the surface erosion releases greater than 5.0% of dexamethasone as a percentage of the total dexamethasone present in the coating in prodrug form, at 37° C. in PBS over not fewer than 6 days; or dexamethasone is released from the coating at a rate such that or $t_{10}$ is greater than or equal to $\frac{1}{10}$ of $t_{50}$.

71. The substrate of any one of items 62-70, wherein the coating further comprises from 0.1% to 10% (w/w) of one or more additives, wherein the one or more additives are selected from plasticizers, antioxidants, binders, lubricants, radio-opaque agents, and mixtures thereof.

72. The substrate of any one of items 62-71, wherein the coating is free of controlled release excipient, free of a crystallization inhibiting excipient, free of a mechanical integrity enhancing excipient, and/or free of a binding excipient; or the coating optionally has a glassy state.

73. The substrate of any one of items 62-72, wherein the coating has a glassy state and is formed from the compound of any one of items 1-4 and 87.

74. An implantable medical device comprising the substrate of any one of items 62-73, wherein the coating resides on the surface of the implantable medical device.

75. A coating having a glassy state formed from the compound of any one of items 2-5 and 95.

76. A method of forming an article comprising Compound 6 or a compound of formula (I):

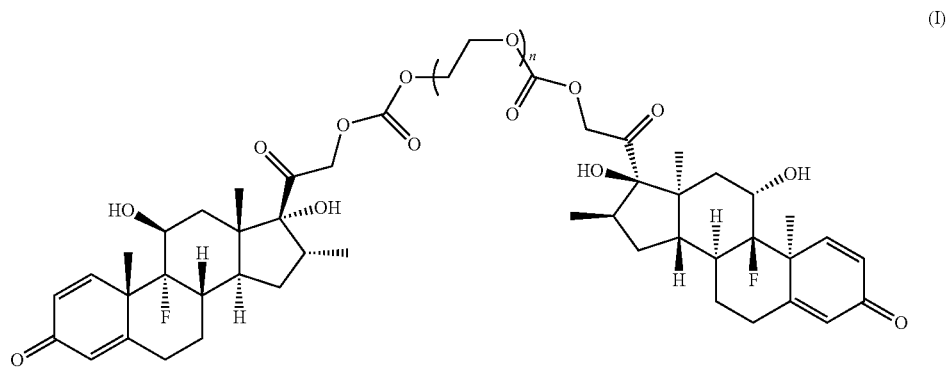

wherein the article is formed by a process comprising the steps of:
(a) heating the compound to form a melt;
(b) cooling the melt to form a glassy state composition; and
(c) heating the glassy state composition to a temperature above the glass transition temperature of the glassy state composition and shaping the glassy state composition to form a shaped article,
wherein n is an integer from 1 to 6.

77. A method of forming an article comprising Compound 6 or a compound of formula (I):

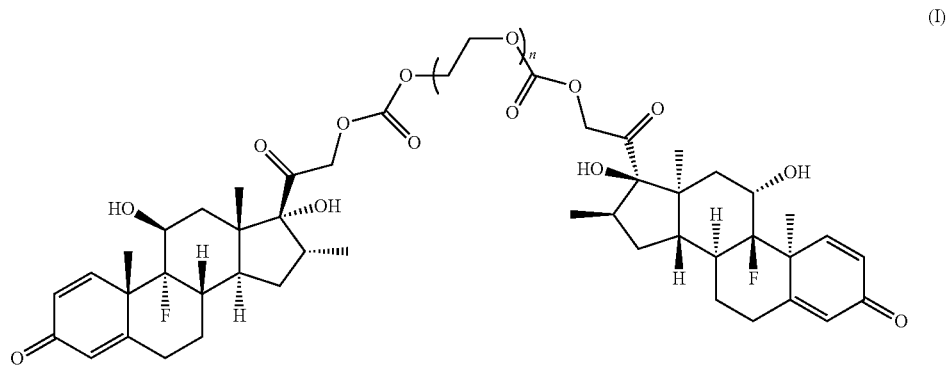

wherein the article is formed by a process comprising the steps of:
    (a) dissolving the compound in a solvent to form a solution;
    (b) evaporating the solvent to form a glassy state composition; and
    (c) heating the glassy state composition to a temperature above the glass transition temperature of the glassy state composition and shaping the glassy state composition to form a shaped article,
    wherein n is an integer from 1 to 6.

78. The method of item 76 or 77, wherein step (c) comprises extruding, molding, blow molding, heat spinning, melt spinning, electrospinning or electrospraying the glassy state composition to form the shaped article.

79. A method of forming an article comprising Compound 6 or a compound of formula (I):

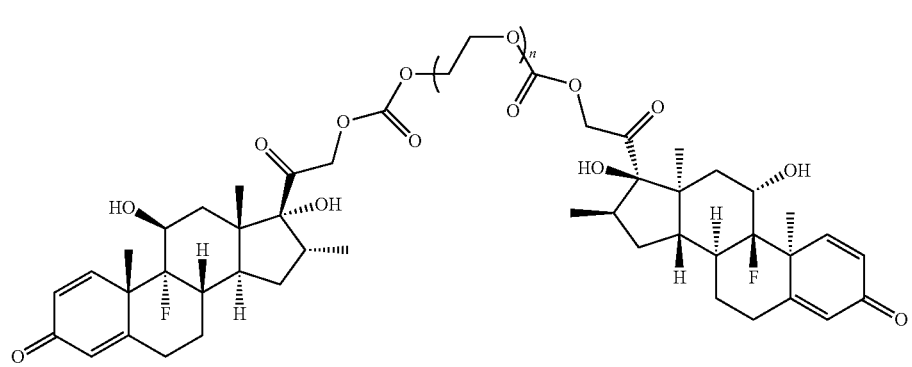

wherein the article is formed by a process comprising the steps of:
    (a) dissolving the compound in a solvent to form a solution;
    (b) electrospraying or electrospinning the solution to form a glassy state composition; and
    (c) heating the glassy state composition to a temperature above the glass transition temperature of the glassy state composition and shaping the glassy state composition to form a coating;
    wherein n is an integer from 1 to 6.

80. The method of any one of items 76-79, wherein the method produces an article free of controlled release excipient, free of a crystallization inhibiting excipient, free of a mechanical integrity enhancing excipient, and/or free of a binding excipient; or the method produces an article that optionally has a glassy state.

81. A solid crystalline form of Compound 1 having an X-ray powder diffraction (XRPD) pattern comprising angles 2θ (°) of 9.316°, 11.501°, 14.019°, 15.982°, 17.268°, 17.685°, 18.658°, 20.440°, 21.782°, 23.472°, 29.816°, and/or 33.150°.

82. The solid crystalline form of Compound 1 of item 81, wherein the solid crystalline form of Compound 1 has an XRPD pattern comprising at least one peak at diffraction angle 2θ (°) of 9.316°.

83. The solid crystalline form of Compound 1 of item 81 or 82, wherein the solid crystalline form of Compound 1 has an XRPD pattern comprising at least one peak at diffraction angle 2θ (°) of 11.501°.

84. The solid crystalline form of Compound 1 of any one of items 81-83, wherein the solid crystalline form of Compound 1 has an XRPD pattern comprising at least one peak at diffraction angle 2θ (°) of 14.019°.

85. The solid crystalline form of Compound 1 of any one of items 81-84, wherein the solid crystalline form of Compound 1 has an XRPD pattern comprising at least one peak at diffraction angle 2θ (°) of 15.982°.

86. The solid crystalline form of Compound 1 of any one of items 81-85, wherein the solid crystalline form of Compound 1 has an XRPD pattern comprising at least one peak at diffraction angle 2θ (°) of 17.268°.

87. The solid crystalline form of Compound 1 of any one of items 81-86, wherein the solid crystalline form of Compound 1 has an XRPD pattern comprising at least one peak at diffraction angle 2θ (°) of 17.685°.

88. The solid crystalline form of Compound 1 of any one of items 81-87, wherein the solid crystalline form of Compound 1 has an XRPD pattern comprising at least one peak at diffraction angle 2θ (°) of 18.658°.

89. The solid crystalline form of Compound 1 of any one of items 81-88, wherein the solid crystalline form of Compound 1 has an XRPD pattern comprising at least one peak at diffraction angle 2θ (°) of 20.440°.

90. The solid crystalline form of Compound 1 of any one of items 81-89, wherein the solid crystalline form of Compound 1 has an XRPD pattern comprising at least one peak at diffraction angle 2θ (°) of 21.782°.

91. The solid crystalline form of Compound 1 of any one of items 81-90, wherein the solid crystalline form of Compound 1 has an XRPD pattern comprising at least one peak at diffraction angle 2θ (°) of 23.472°.

92. The solid crystalline form of Compound 1 of any one of items 81-91, wherein the solid crystalline form of Compound 1 has an XRPD pattern comprising at least one peak at diffraction angle 2θ (°) of 29.816°.

93. The solid crystalline form of Compound 1 of any one of items 81-92, wherein the solid crystalline form of Compound 1 has an XRPD pattern comprising at least one peak at diffraction angle 2θ (°) of 33.150°.

94. The solid crystalline form of Compound 1 of any one of items 81-93, wherein the solid crystalline form of Compound 1 has an XRPD pattern comprising at least one peak diffraction angle 2θ (°) of 9.316°, 11.501°, 14.019°, 15.982°, 17.268°, 17.685°, 18.658°, 20.440°, 21.782°, 23.472°, 29.816°, and 33.150°.

95. Compound 6.

96. A pharmaceutical composition comprising Compound 6 and a pharmaceutically acceptable excipient.

Other Embodiments

Although the foregoing disclosure has been described in some detail by way of illustration and example for purposes of clarity of understanding, the descriptions and examples should not be construed as limiting the scope of the disclosure. The disclosures of all patent and scientific literature cited herein are expressly incorporated in their entirety by reference.

The invention claimed is:

1. A compound having the structure:

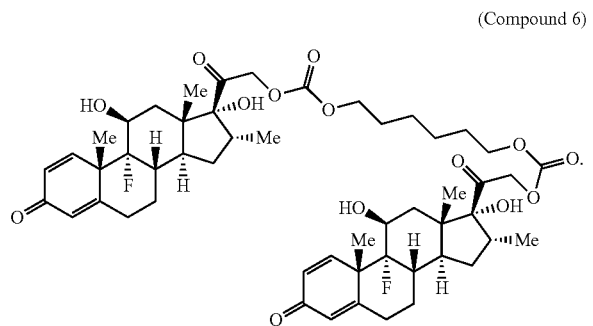

(Compound 6)

2. A method of treating an inflammatory disease or disorder in a subject in need thereof, the method comprising administering to the subject the compound of claim 1 in an amount sufficient to treat the inflammatory disease or disorder in the subject.

3. The method of claim 2, wherein the compound is administered locally.

4. The method of claim 3, wherein the compound is administered intraocularly.

5. The method of claim 3, wherein the compound is administered into a joint space.

6. The method of claim 2, wherein the inflammatory disease or disorder is osteoarthritis.

7. The method of claim 2, wherein the compound is administered to a location by coating a surface of an implantable medical device with the compound and implanting the medical device into the location.

8. An article comprising the compound of claim 1, wherein the article provides controlled release of dexamethasone at 37° C. in phosphate buffered saline.

9. The article of claim 8, wherein at least 70% (w/w) of the article is Compound 6.

10. The article of claim 9, wherein at least 90% (w/w) of the article is Compound 6.

11. The article of claim 8, wherein the article is a fiber, fiber mesh, woven fabric, non-woven fabric, pellet, cylinder, hollow tube, microparticle, nanoparticle, or shaped article.

12. A method of treating an inflammatory disease or disorder in a subject in need thereof, the method comprising administering to the subject the article of claim 8 in an amount sufficient to treat the inflammatory disease or disorder in the subject.

13. The method of claim 12, wherein the article is administered locally.

14. The method of claim 13, wherein the article is administered intraocularly.

15. The method of claim 13, wherein the article is administered into a joint space.

16. The method of claim 12, wherein the article is a fiber, fiber mesh, woven fabric, non-woven fabric, pellet, cylinder, hollow tube, microparticle, nanoparticle, or shaped article.

17. The method of claim 12, wherein at least 70% (w/w) of the article is Compound 6.

18. The method of claim 12, wherein at least 90% (w/w) of the article is Compound 6.

19. The method of claim 12, wherein the inflammatory disease or disorder is osteoarthritis.

* * * * *